US012004709B2

(12) United States Patent
Tezuka et al.

(10) Patent No.: US 12,004,709 B2
(45) Date of Patent: Jun. 11, 2024

(54) FLEXIBLE TUBE INSERTION APPARATUS, INSERTION CONTROL APPARATUS, AND FLEXIBLE TUBE INSERTION METHOD

(71) Applicant: OLYMPUS CORPORATION, Tokyo (JP)

(72) Inventors: Ryo Tezuka, Hachioji (JP); Ryo Tojo, Hachioji (JP); Takeshi Takahashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 934 days.

(21) Appl. No.: 17/027,224

(22) Filed: Sep. 21, 2020

(65) Prior Publication Data

US 2021/0000329 A1 Jan. 7, 2021

Related U.S. Application Data

(63) Continuation of application No. PCT/JP2018/012421, filed on Mar. 27, 2018.

(51) Int. Cl.
*A61B 1/00* (2006.01)
*A61B 1/005* (2006.01)
(Continued)

(52) U.S. Cl.
CPC ...... *A61B 1/00078* (2013.01); *A61B 1/00006* (2013.01); *A61B 1/00009* (2013.01); *A61B 1/0002* (2013.01); *A61B 1/0057* (2013.01); *A61B 5/065* (2013.01); *A61B 1/00045* (2013.01); *A61B 1/0058* (2013.01); *A61B 1/31* (2013.01); *A61B 2034/2061* (2016.02)

(58) Field of Classification Search
CPC . A61B 1/00006; A61B 1/0002; A61B 1/0057; A61B 5/065; A61B 2034/2061
See application file for complete search history.

(56) References Cited

U.S. PATENT DOCUMENTS 5,885,208 A 3/1999 Moriyama

FOREIGN PATENT DOCUMENTS

EP 1 795 115 A1 6/2007
JP S61-37931 8/1986
(Continued)

OTHER PUBLICATIONS

Japanese Office Action dated Jun. 15, 2021 received in 2020-510237.
(Continued)

*Primary Examiner* — Timothy J Neal
(74) *Attorney, Agent, or Firm* — Scully, Scott, Murphy & Presser, P.C.

(57) ABSTRACT

A flexible tube insertion apparatus includes: a flexible tube; a stiffness control system configured to control a stiffness of the tube; a buckling detection system configured to detect occurrence of a buckling in the tube; a pulling operation detection system configured to detect that a pulling operation of the tube is performed, after detection of the occurrence of the buckling; and a storage configured to store position information of a stiffness-to-be-enhanced portion of the tube neighboring a buckling portion of the tube and located on a distal side of the buckling portion. The stiffness control system is configured to enhance a stiffness of the stiffness-to-be-enhanced portion, based on the position information, at detection of the pulling operation.

33 Claims, 23 Drawing Sheets

(51) Int. Cl.
*A61B 5/06* (2006.01)
*A61B 1/31* (2006.01)
*A61B 34/20* (2016.01)

(56) References Cited

FOREIGN PATENT DOCUMENTS

| | | |
|---|---|---|
| JP | 5-176986 | 7/1993 |
| JP | 10-305005 | 11/1998 |
| JP | 4009519 | 11/2007 |
| JP | 2016-7434 A | 1/2018 |
| WO | 2017/109986 A1 | 6/2017 |
| WO | 2017/109988 A1 | 6/2017 |

OTHER PUBLICATIONS

English translation of International Preliminary Report on Patentability dated Oct. 8, 2020, together with the Written Opinion issued in International Application No. PCT/JP2018/012421.
International Search Report dated Jun. 19, 2018 received in International Application No. PCT/JP2018/012421, together with an English-language translation.

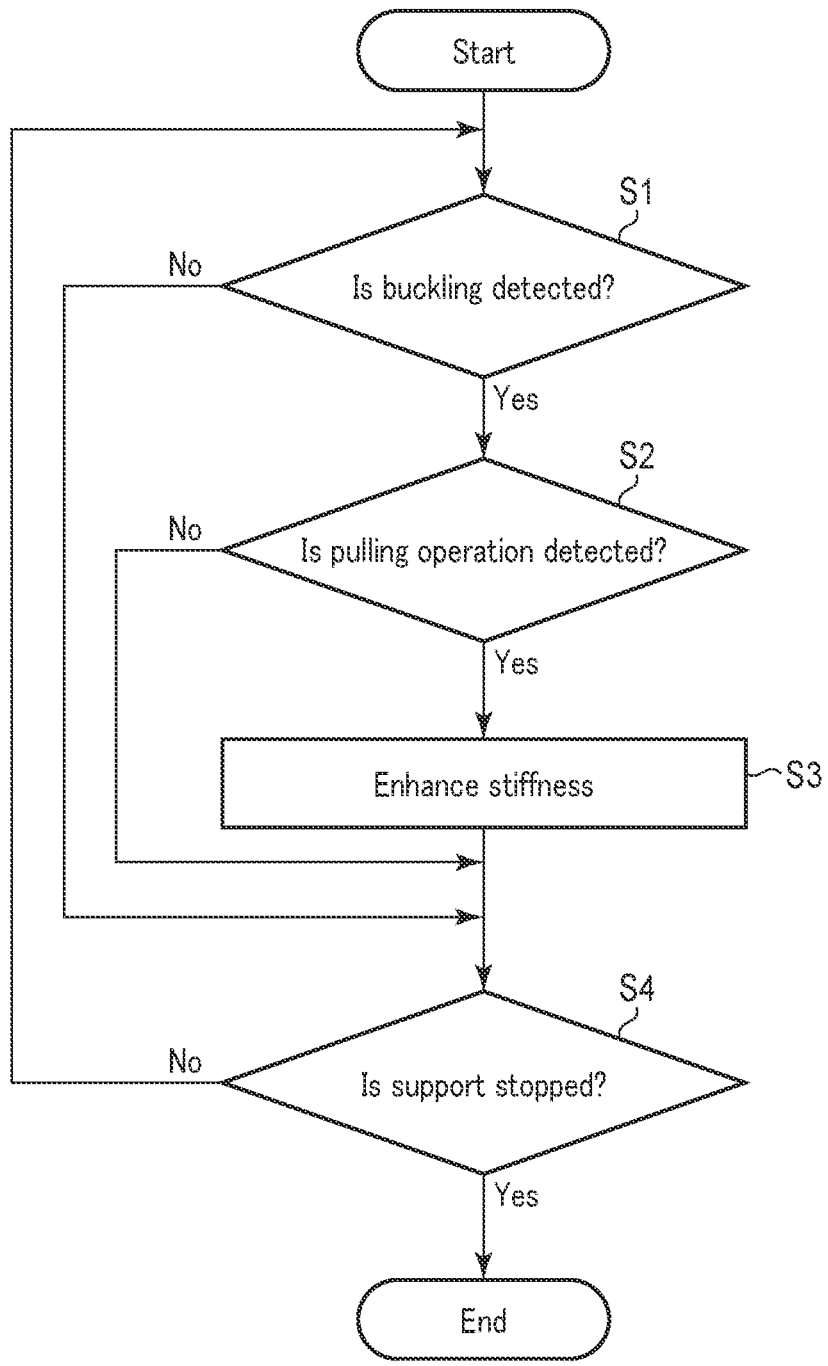
F I G. 12

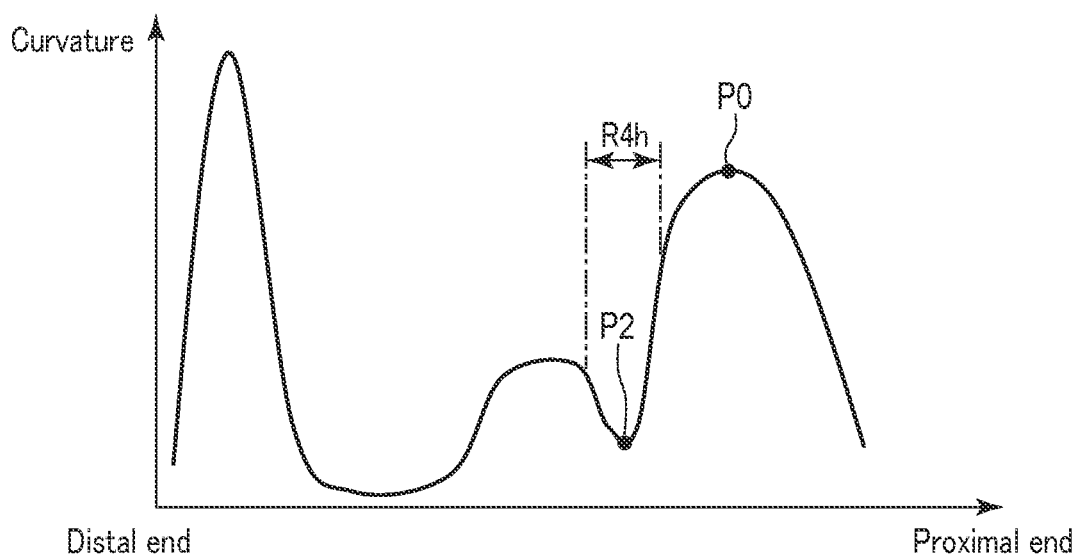
F I G. 21
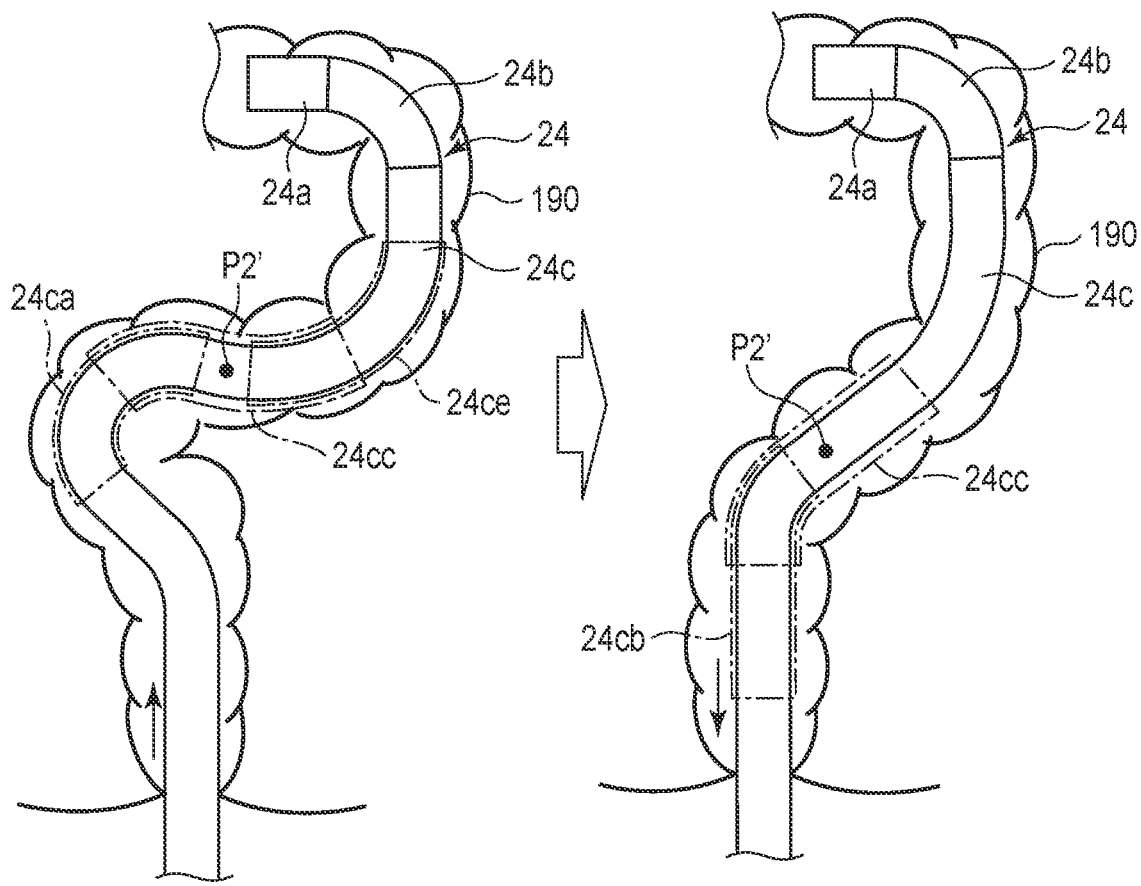
F I G. 22

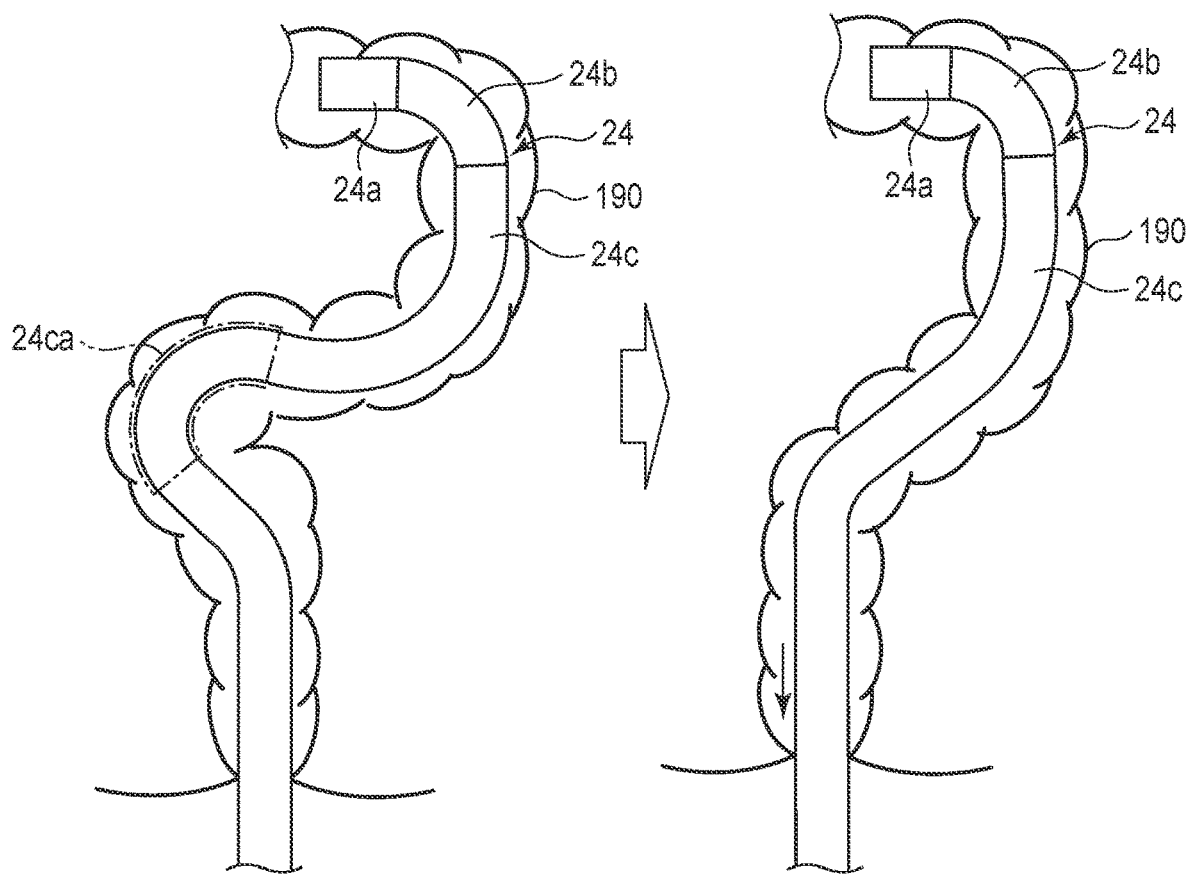
F I G. 31
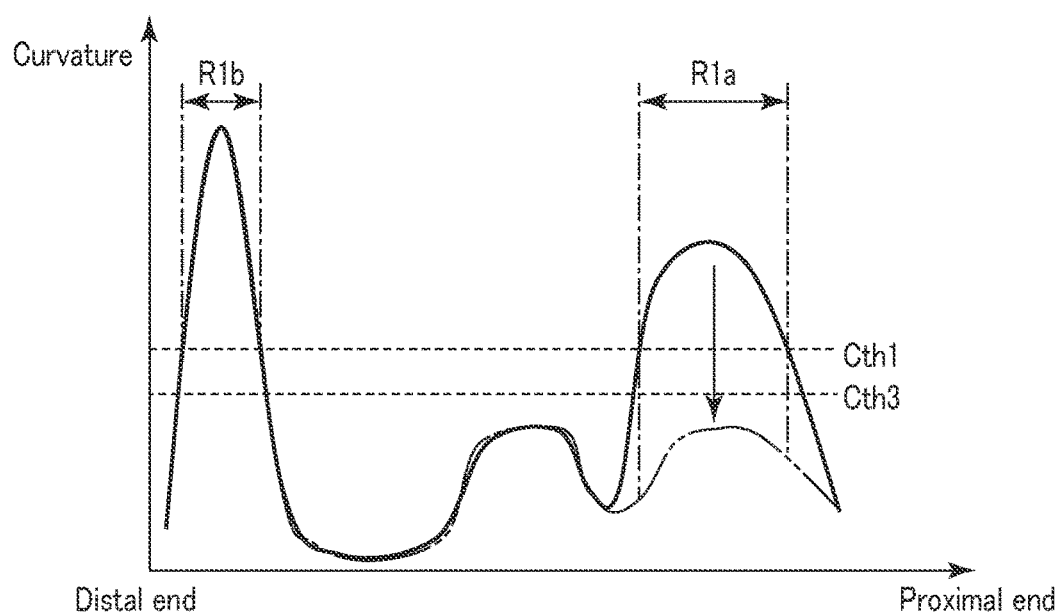
F I G. 32

FLEXIBLE TUBE INSERTION APPARATUS, INSERTION CONTROL APPARATUS, AND FLEXIBLE TUBE INSERTION METHOD

CROSS-REFERENCE TO RELATED APPLICATIONS

This application is a Continuation Application of PCT Application No. PCT/JP2018/012421, filed Mar. 27, 2018, the entire contents of which are incorporated herein by reference.

BACKGROUND OF THE INVENTION

1. Field of the Invention

The present invention relates to a flexible tube insertion apparatus including a flexible tube to be inserted into a tract of a target, an insertion control apparatus of the flexible tube, and an insertion control method of the flexible tube.

2. Description of the Related Art

As one of flexible tube insertion apparatuses, there is known an endoscope apparatus including an endoscope. The endoscope includes a soft, elongated insertion section to be inserted into a tract of a target. The insertion section includes an imaging element in a distal portion thereof. The insertion section also includes a soft tube composed of a flexible tube. Further, as one of endoscopes, there is known a colonoscope designed to be inserted into the large intestine.

The large intestine is generally classified into the rectum, colon, and cecum from the anus side, and the colon is further classified into the sigmoid colon, descending colon, transverse colon, and ascending colon from the rectum side. In general, the sigmoid colon and the transverse colon are not fixed in the abdominal part and easily move. If the insertion section of the endoscope is inserted into such an intestinal tract, the insertion section advances in the intestinal tract while bending along the intestinal wall. However, when the insertion section is further pushed in from the proximal side, there is a case in which the soft insertion section bends in a different direction from a direction in which force is applied in the intestine, and the distal end of the insertion section does not further advance.

As a solution to such a situation, there is known a technology in which the flexural stiffness of the insertion section itself is enhanced, or the flexural stiffness of the insertion section is enhanced by attaching an overtube having a different quality of material from the insertion section to the insertion section, thereby facilitating transmission of force in a direction in which the insertion section is to be inserted.

However, if the flexural stiffness of the entirety of the insertion section is uniformly changed, it is not possible to obtain a shape change of the insertion section in accordance with a bend state in the intestinal tract. Consequently, in some cases, the insertion section may come to a standstill, for example, in the sigmoid colon, and may excessively extend the sigmoid colon. Such an insertion section is disadvantageous in the insertion into a deeper part. Other technologies are known to improve the insertability of the insertion section into the large intestine.

Jpn. Pat. Appln. KOKOKU Publication No. S61-37931 discloses a technology in which an elongated soft tube of an endoscope is segmented into ranges in the longitudinal direction, and the degrees of softness in the ranges are changed to different stiffness.

Japanese Patent No. 4009519 discloses a technology in which a soft tube of an endoscope is provided with a small-diameter portion, a taper portion, and a large-diameter portion, thereby making the flexural stiffness different, and enhancing insertability.

Jpn. Pat. Appln. KOKAI Publication No. 2016-7434 discloses a technology in which, in an endoscope including an insertion section including segments coupled along the axis, when a segment receives a pushing pressure from the wall of a tract, the stiffness of two or more coupled segments is lowered and the bend amount of the two or more coupled segments is increased, thereby lowering the pressure received from the wall of the tract.

International Publication No. 2017/109988 discloses a technology in which the bending of an insertion section is judged from shape information (curvature, radius of curvature) of the insertion section, and the flexural stiffness of a stiffness changing part corresponding to a segment disposed in the bend portion is controlled and set to such a flexural stiffness that the bend portion becomes substantially straight.

International Publication No. 2017/109986 discloses a technology in which advancing of an insertion section is detected and the stiffness of the insertion section is lowered, or retreating of the insertion section is detected and the stiffness of a bend portion is increased to such a stiffness that the bend portion becomes substantially straight (a loop is made straight).

BRIEF SUMMARY OF THE INVENTION

A flexible tube insertion apparatus includes: a flexible tube to be inserted into a tract of a target; a stiffness control system configured to control a stiffness of each of various portions of the flexible tube; a buckling detection system configured to detect occurrence of a buckling in the flexible tube; a pulling operation detection system configured to detect that a pulling operation of the flexible tube is performed, after the buckling detection system detects the occurrence of the buckling; and a storage device configured to store position information of a stiffness-to-be-enhanced portion including a portion of the flexible tube neighboring a buckling portion of the flexible tube and located on a distal side of the buckling portion. The stiffness control system is configured to enhance a stiffness of the stiffness-to-be-enhanced portion, based on the position information stored in the storage device, when the pulling operation detection system detects the pulling operation.

An insertion control apparatus includes: a stiffness control system configured to control a stiffness of each of various portions of a flexible tube to be inserted into a tract of a target; a buckling detection system configured to detect occurrence of a buckling in the flexible tube; a pulling operation detection system configured to detect that a pulling operation of the flexible tube is performed, after the buckling detection system detects the occurrence of the buckling; and a storage device configured to store position information of a stiffness-to-be-enhanced portion including a portion of the flexible tube neighboring a buckling portion of the flexible tube and located on a distal side of the buckling portion. The stiffness control system is configured to enhance a stiffness of the stiffness-to-be-enhanced portion, based on the position information stored in the storage device, when the pulling operation detection system detects the pulling operation.

A flexible tube insertion method includes: controlling a stiffness of each of various portions of a flexible tube to be inserted into a tract of a target; detecting occurrence of a buckling in the flexible tube; detecting that a pulling operation of the flexible tube is performed, after detecting the occurrence of the buckling; storing position information of a stiffness-to-be-enhanced portion including a portion of the flexible tube neighboring a buckling portion of the flexible tube and located on a distal side of the buckling portion; and enhancing a stiffness of the stiffness-to-be-enhanced portion, based on the stored position information, when detecting the pulling operation.

A flexible tube insertion method includes: inserting a flexible tube into a tract of a target, the flexible tube including stiffness changing devices arranged along a longitudinal axis of the flexible tube; performing a pulling operation of the flexible tube after a buckling occurs in the flexible tube; and enhancing a stiffness of a stiffness changing device that is located at a stiffness-to-be-enhanced portion including a portion of the flexible tube neighboring a buckling portion of the flexible tube and located on a distal side of the buckling portion, after the pulling operation is performed.

Advantages of the invention will be set forth in the description that follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 12 shows a flowchart of a process in an insertion support operation of an insertion section in the flexible tube insertion apparatus shown in FIG. 2.

FIG. 21 is a graph showing curvatures of various portions of the insertion section in a state in which a buckling occurred, FIG. 21 being a graph for explaining still another example of the manner of determining a stiffness-to-be-enhanced portion in the buckling detection system shown in FIG. 14.

FIG. 22 is a view for explaining still another example of the manner of determining a stiffness-to-be-enhanced portion in the buckling detection system shown in FIG. 14, FIG. 22 showing the insertion section in a state in which a buckling occurs, and the insertion section in which the buckling is eliminated by a pulling operation.

FIG. 31 is a view for describing the pulling operation detection system shown in FIG. 30, FIG. 31 showing a state in which a buckling is eliminated by a pulling operation of the insertion section.

FIG. 32 is a view for describing the pulling operation detection system shown in FIG. 30, FIG. 32 showing a variation of a graph indicative of curvatures of various portions of the insertion section that transitions from a state in which a buckling occurs to a state in which the buckling is eliminated.

DETAILED DESCRIPTION OF THE INVENTION

Here, as regards a flexible tube insertion apparatus according to the present embodiment, an example in which the flexible tube insertion apparatus is applied to a medical endoscope will be described. The medical endoscope may be, for example, an upper gastrointestinal endoscope, a colonoscope, an ultrasonic endoscope, a cystoscope, or a pyeloscope. The flexible tube insertion apparatus according to the present embodiment is not limited to the medical endoscope, and is generally applicable to a device configured to operate a flexible tube and to perform operations such as insertion and treatment. Examples of this device include a catheter and a medical manipulator. Further, the flexible tube insertion apparatus according to the present embodiment may be an industrial endoscope.

[Flexible Tube Insertion Apparatus 10]

Figure 1:
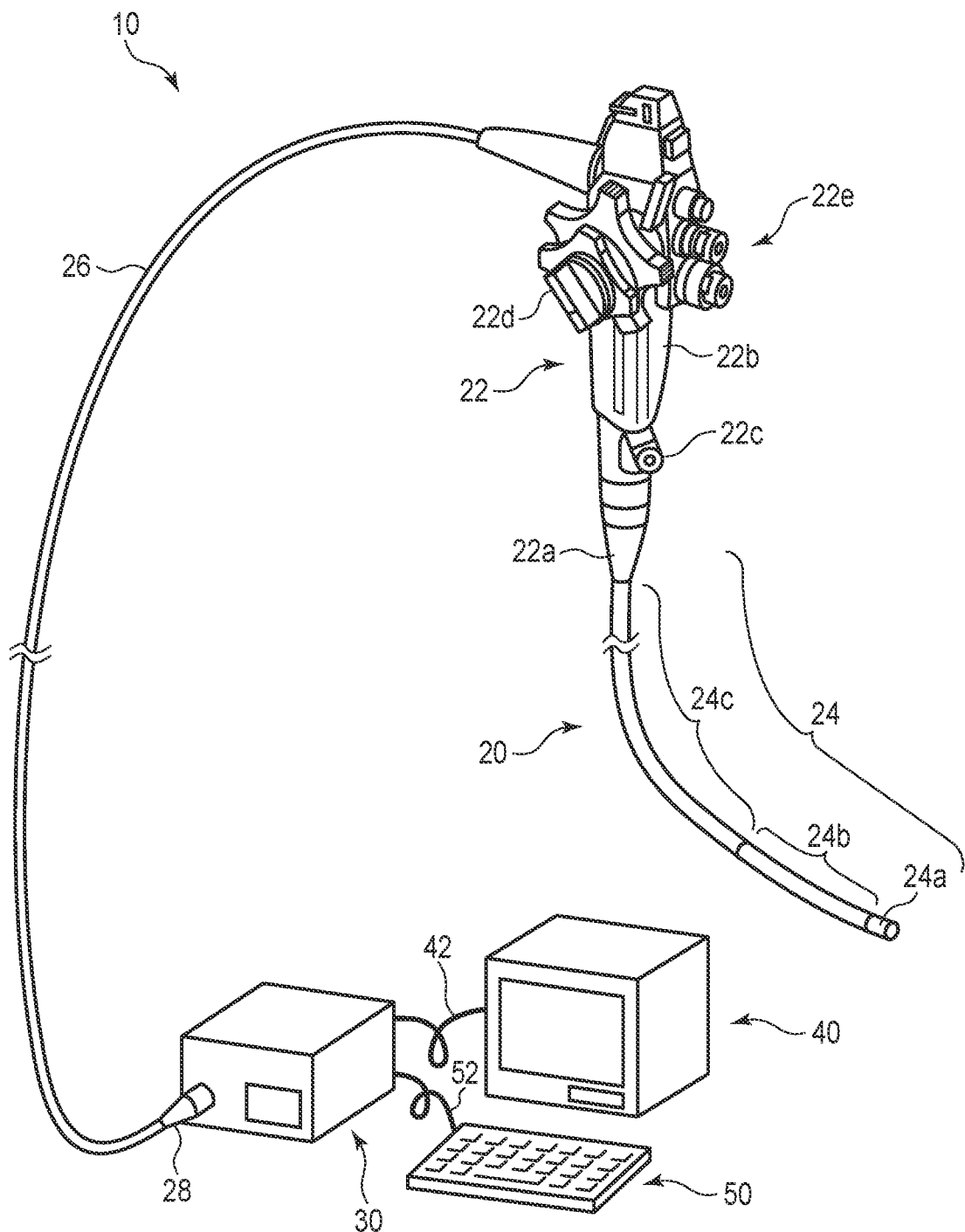
FIG. 1 shows a flexible tube insertion apparatus according to an embodiment.

FIG. 1 shows a flexible tube insertion apparatus 10 according to the present embodiment. The flexible tube insertion apparatus 10 includes an endoscope 20; an insertion control apparatus 30 to which the endoscope 20 is connected; a display 40 that is connected to the insertion control apparatus 30; and an input device 50 that is connected to the insertion control apparatus 30.

The endoscope 20 includes an elongated insertion section 24 to be inserted into a tract of an observation target; a control section 22 coupled to a proximal portion of the insertion section 24; and a universal cord 26 extending from the control section 22.

The insertion section 24 includes a hard distal section 24a that is composed to be hard; a bendable section 24b coupled to the proximal side of the hard distal section 24a; and a soft tube 24c that is a flexible tube coupled to the proximal side of the bendable section 24b. The hard distal section 24a includes, for example, an illumination light emission unit configured to emit illumination light that illuminates an observation target; and an imaging element configured to image the observation target. The bendable section 24b can be bent in a desired direction by operating the control section 22. Specifically, the bendable section 24b is configured to be actively bendable. The soft tube 24c is configured to be passively bendable. For example, the soft tube 24c, when inserted into a tract of the observation target, is bent in accordance with the shape of the tract.

The control section 22 includes a protection hood portion 22a coupled to the proximal side of the soft tube 24c; and a gripper 22b coupled to the proximal side of the protection hood portion 22a. The protection hood portion 22a is provided with a treatment instrument insertion hole 22c communicating with an insertion channel extending in the insertion section 24. The gripper 22b includes a bending operation dial 22d for bend-operating the bendable section 24b; and switches 22e for performing air feed, water feed, suction, imaging, etc.

The endoscope 20 is connected to the insertion control apparatus 30 by the universal cord 26. The universal cord 26 includes a connection portion 28 that is detachably attached to the insertion control apparatus 30. The connection portion 28 functions as an interface of data that is transmitted and received between the endoscope 20 and the insertion control apparatus 30.

The display 40 is a device configured to display various kinds of information, such as an observation image by the endoscope 20. The display 40 is connected to the insertion control apparatus 30 through a cable 42. The display 40 may be composed of, for example, a liquid crystal display, although the display 40 is not limited to this.

The input device 50 is a general device for input, such as a keyboard. The input device 50 is connected to the insertion control apparatus 30 through a cable 52. Various instructions and the like for operating the endoscope 20 are input to the input device 50. The input device 50 may be composed of an operation panel provided on the insertion control apparatus 30. Alternatively, the input device 50 may be composed of a touch panel constituting a display screen of the display 40.

The insertion control apparatus 30 has a function of controlling the endoscope 20; a function of acquiring various kinds of information through the input device 50; and a function of outputting various kinds of information to the display 40. The insertion control apparatus 30 includes, for example, a computer. Specifically, the insertion control apparatus 30 includes a processor configured to operate according to pre-programmed software, and a storage device configured to store software and necessary information. Various circuits to be described later (e.g. an image processing circuit 76, a stiffness control circuit 86, and a shape calculation circuit 96) in the insertion control apparatus 30 are constituted by combinations of processors and storage devices. Alternatively, various circuits in the insertion control apparatus 30 may be constituted by combining dedicated circuits and/or general-purpose circuits.

Figure 2:
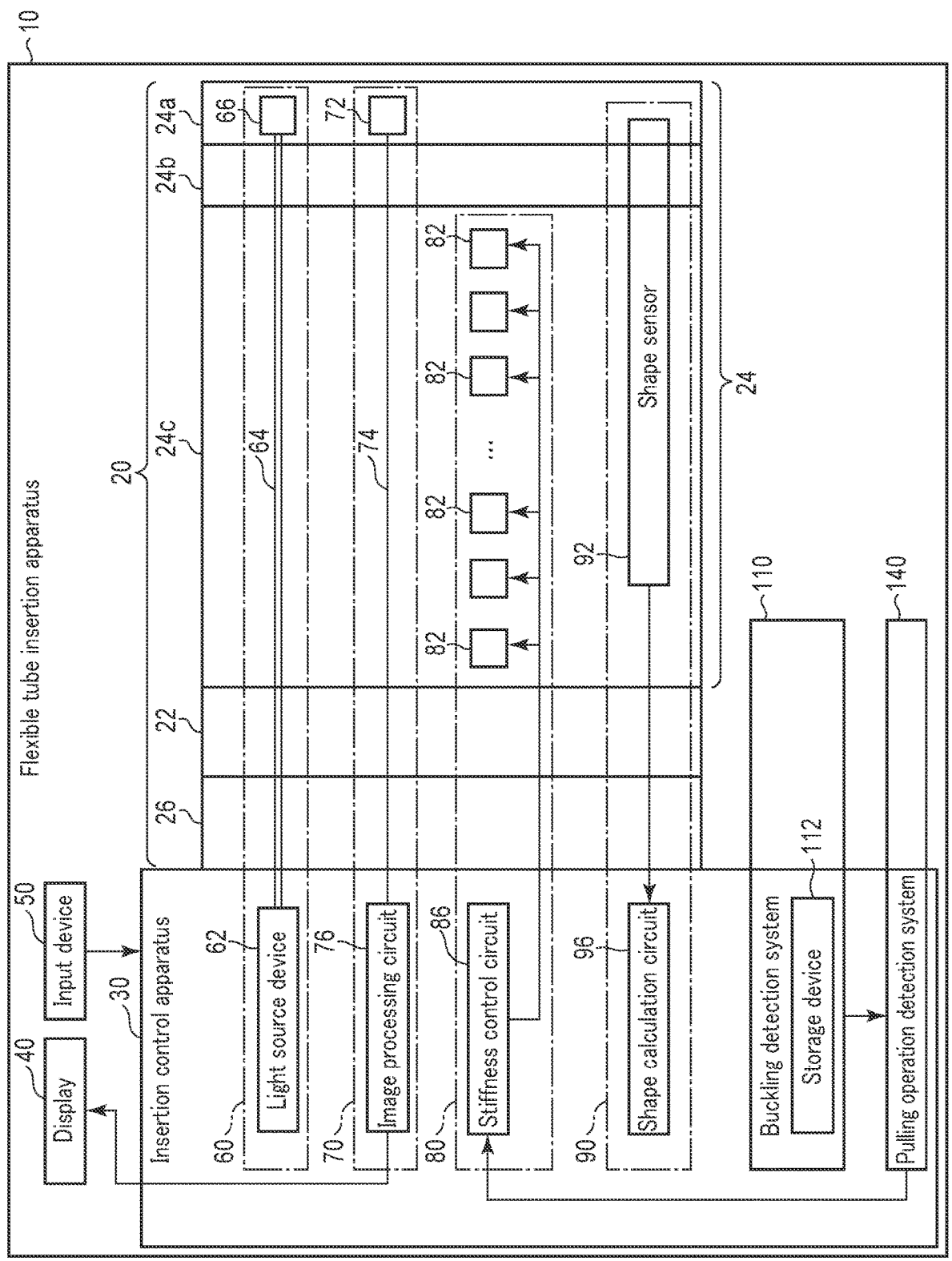
FIG. 2 shows functional blocks of the flexible tube insertion apparatus shown in FIG. 1.

FIG. 2 shows functional blocks of the flexible tube insertion apparatus 10 shown in FIG. 1. As shown in FIG. 2, the flexible tube insertion apparatus 10 includes an illumination system 60 for illuminating an observation target, and an imaging system 70 for imaging the observation target.

The illumination system 60 includes a light source device 62 configured to emit light for illuminating the observation target; a light guide member 64 configured to guide light emitted from the light source device 62; and a light emission unit 66 configured to emit light guided by the light guide member 64 to the outside of the endoscope 20.

The light source device 62 is disposed inside the insertion control apparatus 30. The light guide member 64 extends in the inside of the endoscope 20. To be more specific, the light guide member 64 extends from the connection portion 28 that is detachably attached to the insertion control apparatus 30, passes through the inside of the universal cord 26, control section 22, and insertion section 24, and extends up to the hard distal section 24a. The light guide member 64 may be composed of, for example, a single optical fiber, or a bundle fiber in which optical fibers are bundled. The light emission unit 66 is disposed in the hard distal section 24a and is optically connected to the light guide member 64.

In other words, the light source device 62 cooperates with the endoscope 20, more specific, the light guide member 64 and light emission unit 66 in the endoscope 20, to constitute the illumination system 60.

Light emitted from the light source device 62 enters the light guide member 64. The light entering the light guide member 64 is guided by the light guide member 64, and enters the light emission unit 66. The light entering the light emission unit 66 is emitted to the outside of the endoscope 20 by the light emission unit 66. The light emitted to the outside of the endoscope 20 is, for example, applied to an observation target. The light applied to the observation target is, for example, reflected or scattered by the observation target.

The imaging system 70 includes an imaging element 72 configured to acquire an optical image of the observation target illuminated by the illumination system 60; and an image processing circuit 76 configured to process an image signal of the optical image of the observation target acquired by the imaging element 72. The imaging element 72 is disposed in the hard distal section 24a. The image processing circuit 76 is disposed inside the insertion control apparatus 30. The imaging element 72 is electrically connected to the image processing circuit 76, for example, by an imaging cable 74.

The image signal of the optical image of the observation target acquired by the imaging element 72 is supplied to the image processing circuit 76. The image processing circuit 76 executes a necessary image process on the supplied image signal, and supplies the image-processed image signal to the display 40. The display 40 displays an image in accordance with the supplied image signal.

The flexible tube insertion apparatus 10 further includes a stiffness control system 80 configured to control the stiffness of each of various portions of the soft tube 24c of the insertion section 24; and a shape calculation system 90 configured to calculate the shape of the insertion section 24.

The stiffness control system 80 includes stiffness changing devices 82, and a stiffness control circuit 86 configured to independently control the stiffness changing devices 82. The stiffness changing devices 82 are arranged on the soft tube 24c along the longitudinal axis of the insertion section 24. Each stiffness changing device 82 is configured to be able to change the stiffness of a portion of the soft tube 24c on which the stiffness changing device 82 is provided. The details of the stiffness control system 80 will be described later.

The shape calculation system 90 includes a shape sensor 92 configured to acquire shape information of each of various portions of the insertion section 24; and a shape calculation circuit 96 configured to calculate the shape of the entirety of the insertion section 24, based on the shape information of each of various portions of the insertion section 24 acquired by the shape sensor 92. The details of the shape calculation system 90 will be described later.

The flexible tube insertion apparatus 10 further includes a buckling detection system 110 configured to detect occurrence of a buckling in the flexible tube, and a pulling operation detection system 140 configured to detect that a pulling operation of the insertion section 24 is performed, after the buckling detection system 110 detects the occurrence of the buckling. The buckling detection system 110 includes a storage device configured to store information relating to the buckling. The details of the buckling detection system 110 and the pulling operation detection system 140 will be described later.

[Configuration Example 1 of Stiffness Control System]

Figure 3:
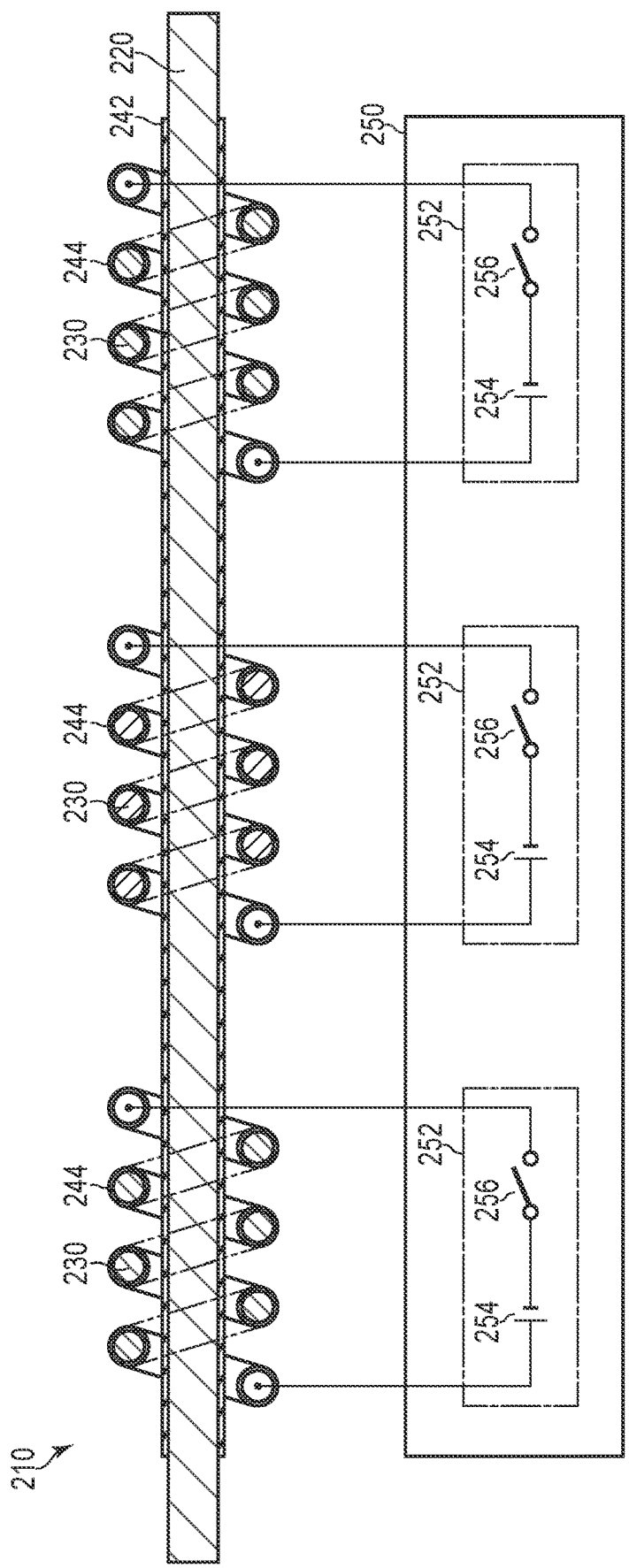
FIG. 3 shows a stiffness changing device and a stiffness control circuit in a configuration example of a stiffness control system shown in FIG. 2.

FIG. 3 shows a stiffness changing device 210 and a stiffness control circuit 250 in a configuration example of the stiffness control system 80. As illustrated in FIG. 3, the stiffness changing device 210 has a function of providing different stiffness to the soft tube 24c by taking different stiffness states. The stiffness changing device 210 includes a shape memory member 220 capable of transitioning in phase between a first phase and a second phase, and inducing members 230 that are configured to induce the shape memory member 220 to transition in phase between the first phase and second phase.

When the shape memory member 220 is in the first phase, the shape memory member 220 takes a soft state in which the shape memory member 220 can easily deform in accordance with external force, i.e. the shape memory member 220 exhibits a low elastic coefficient, so as to provide a relatively low stiffness to the soft tube 24c. When the shape memory member 220 is in the second phase, the shape memory member 220 takes a hard state in which the shape memory member 220 tends to take a memorized shape that is memorized in advance against external force, i.e. the shape memory member 220 exhibits a high elastic coefficient, so as to provide a relatively high stiffness to the soft tube 24c.

Each inducing member 230 has a capability of generating heat. The shape memory member 220 has a characteristic of transitioning in phase from the first phase to the second phase on heating the inducing member 230.

The shape memory member 220 is elongated, and the inducing members 230 are arranged at intervals along the longitudinal axis of the shape memory member 220.

The shape memory member 220 may be composed of, for example, a shape memory alloy. The shape memory member 220 may be, for example, an alloy including NiTi, although the shape memory member 220 is not limited to this. Besides, the shape memory member 220 may be composed of some other material, such as a shape memory polymer, a shape memory gel, or a shape memory ceramic.

The inducing member 230 may be composed of, for example, a heater. Specifically, the inducing member 230 may have a characteristic of generating heat by the supply of current flowing in the inducing member 230. The inducing member 230 may be, for example, a heating wire, i.e. an electrically conductive member with a high electrical resistance. The inducing member 230 only needs to have a capability of generating heat, and may be composed of, aside from a heater, an imaging element, a light guide, or some other element or member. Furthermore, the inducing member 230 may be composed of a structure configured to generate heat by a chemical reaction.

The shape memory member 220 may be composed of an electrically conductive material. For example, an insulating film 242 is provided around the shape memory member 220. The insulating film 242 functions to prevent short-circuit between the shape memory member 220 and the inducing member 230.

The inducing member 230 may be composed of an electrically conductive material. For example, an insulating film 244 is provided around the inducing member 230. The insulating film 244 functions to prevent short-circuit between the shape memory member 220 and the inducing member 230 and short-circuit between neighboring portions of the inducing member 230.

The stiffness control circuit 250 includes driving circuits 252 that are configured to respectively drive the inducing members 230. Each driving circuit 252 includes a power source 254 and a switch 256. Each driving circuit 252 is electrically connected across the corresponding inducing member 230. Each driving circuit 252 supplies current to the corresponding inducing member 230 in accordance with ON of the switch 256, i.e. a closing operation of the switch 256, and stops the supply of current to the corresponding inducing member 230 in accordance with OFF of the switch 256, i.e. an opening operation of the switch 256. The inducing member 230 generates heat in accordance with the supply of current. The shape memory member 220 may have a wire shape.

The inducing member 230 is disposed near the shape memory member 220. The inducing member 230 may have a coil shape, and the shape memory member 220 may extend through the inside of the coil-shaped inducing member 230.

When the switch 256 of the driving circuit 252 is in the OFF state, the shape memory member 220 is in the first phase, which corresponds to the soft state in which the elastic coefficient is low. In the first phase, the shape memory member 220 is in the state in which the shape memory member 220 easily deforms in accordance with external force.

If the switch 256 of the driving circuit 252 is changed over into the ON state, current flows in the inducing member 230, and the inducing member 230 generates heat. As a result, the shape memory member 220 transitions in phase into the second phase, which corresponds to the hard state in which the elastic coefficient is high. In the second phase, the shape memory member 220 exhibits a tendency to take a memorized shape.

When the shape memory member 220 is in the first phase, the stiffness changing device 210 provides a relatively low stiffness to the soft tube 24c, and the shape memory member 220 easily deforms in accordance with external force acting on the soft tube 24c, i.e. the force that can deform the shape memory member 220.

When the shape memory member 220 is in the second phase, the stiffness changing device 210 provides a relatively high stiffness to the soft tube 24c, and the shape memory member 220 exhibits a tendency to return to the memorized shape against the external force acting on the soft tube 24c, i.e. the force that can deform the shape memory member 220.

For example, the phase of a part of the shape memory member 220, which is located near each inducing member 230, is switched between the first phase and the second phase by the stiffness control circuit 250, so that the stiffness of the soft tube 24c is switched. The supply of current to the inducing members 230 is independently switched by the stiffness control circuit 250, so shat the phases of parts of the shape memory member 220 are independently switched. Accordingly, the stiffness of parts of the soft tube 24c is independently switched. Thereby, the stiffness changing device 210 can provide a desired complex stiffness distribution to the soft tube 24c.

[Configuration Example 2 of Stiffness Control System]

Figure 4:
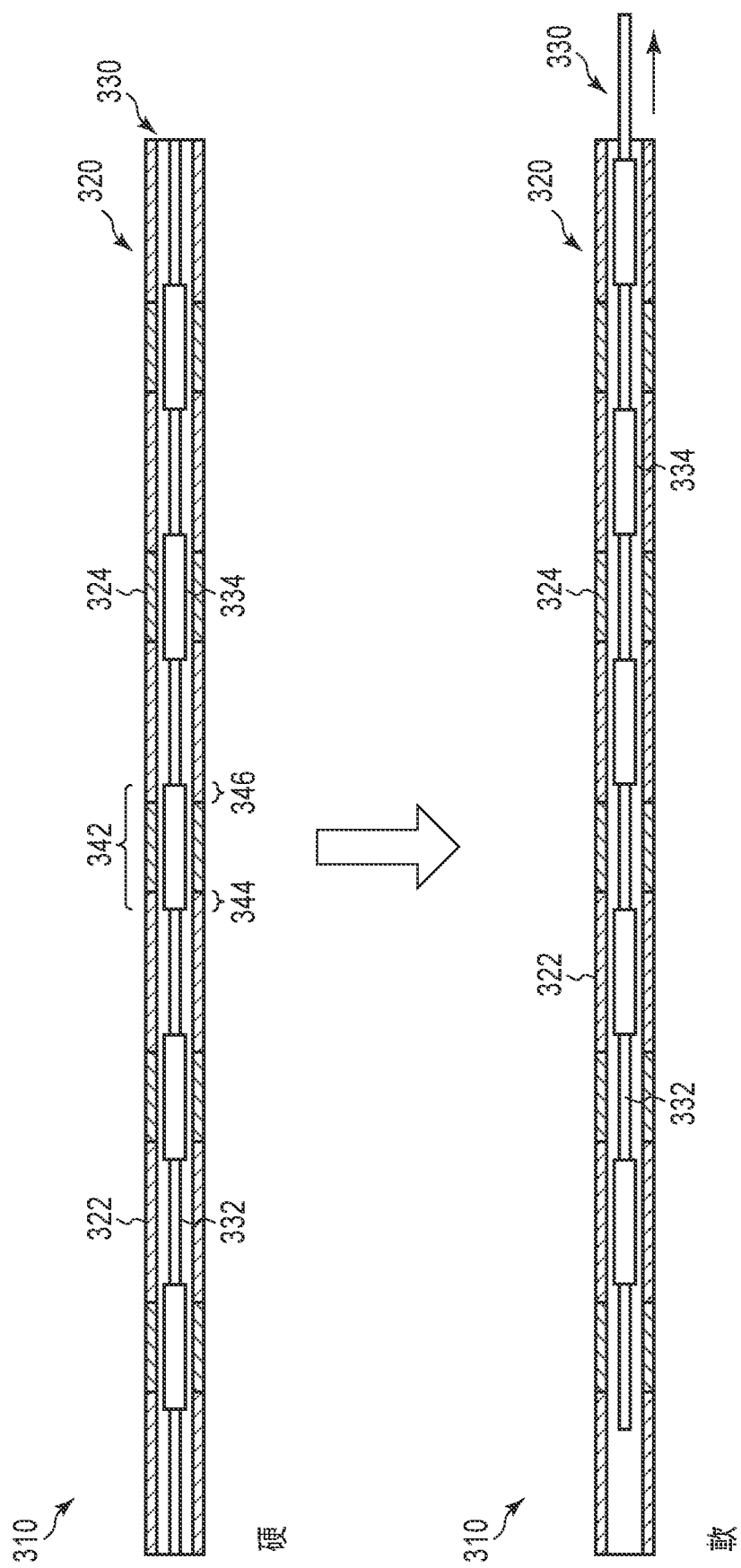
FIG. 4 shows a stiffness changing device in another configuration example of the stiffness control system shown in FIG. 2.

FIG. 4 shows a stiffness changing device 310 in another configuration example of the stiffness control system 80. FIG. 4 shows the state of switching of stiffness of the stiffness changing device 310 from a high stiffness state to a low stiffness state. In FIG. 4, the stiffness changing device 310 in the high stiffness state is depicted in an upper part of FIG. 4, and the stiffness changing device 310 in the low stiffness state is depicted in a lower part of FIG. 4.

The stiffness changing device 310 is a device for providing different stiffness to the soft tube 24c, which is the object of attachment. The stiffness changing device 310 includes a first longitudinal member 320 and a second longitudinal member 330. The second longitudinal member 330 is disposed adjacently along the first longitudinal member 320. For example, the first longitudinal member 320 is composed of an outer tube, and the second longitudinal member 330 is composed of a core member disposed inside the outer tube. For example, the outer tube has an annular cross-sectional shape perpendicular to the axis, and the core member has a circular outer peripheral shape in cross section perpendicular to the axis. In this case, stable flexural stiffness is provided with respect to bending in all directions.

The first longitudinal member 320 includes high flexural stiffness portions 322 and low flexural stiffness portions 324. For example, the first longitudinal member 320 includes six high flexural stiffness portions 322 and five low flexural stiffness portions 324. The high flexural stiffness portions 322 and low flexural stiffness portions 324 are successively and alternately arranged along the axis of the first longitudinal member 320. The high flexural stiffness portion 322 has a flexural stiffness higher than a flexural stiffness of the low flexural stiffness portion 324. Thus, the first longitudinal member 320 is relatively easily bendable at the low flexural stiffness portion 324, and is relatively less easily bendable at the high flexural stiffness portion 322.

The second longitudinal member 330 includes non-bend-restriction portions 332 and bend-restriction portions 334. For example, the second longitudinal member 330 includes six non-bend-restriction portions 332 and five bend-restriction portions 334. The non-bend-restriction portions 332 and bend-restriction portions 334 are successively and alternately arranged along the axis of the second longitudinal member 330. The bend-restriction portion 334 has a flexural stiffness higher than a flexural stiffness of the non-bend-restriction portion 332. Thus, the second longitudinal member 330 is relatively easily bendable at the non-bend-restriction portion 332, and is relatively less easily bendable at the bend-restriction portion 334. For example, the non-bend-restriction portion 332 is composed of a small-diameter portion having a relatively small diameter, and the bend-restriction portion 334 is composed of a large-diameter portion having a relatively large diameter. The bend-restriction portion 334 has, for example, a uniform thickness from an end portion to the other end portion thereof.

In the stiffness changing device 310, the relative position of the second longitudinal member 330 to the first longitudinal member 320 is changed, which allows the flexural stiffness of the stiffness changing device in the low flexural stiffness portion 324 to be switched between a high stiffness state in which the flexural stiffness is relatively high and a low stiffness state in which the flexural stiffness is relatively low.

The switching from the high stiffness state to the low stiffness state is effected by relative movement of the second longitudinal member 330 to the first longitudinal member 320 along the axis of the first longitudinal member 320.

In the high stiffness state, the bend-restriction portion 334 of the second longitudinal member 330 is disposed in a range including the low flexural stiffness portion 324 of the first longitudinal member 320. The bend-restriction portion 334 restricts the bend of the low flexural stiffness portion 324 of the first longitudinal member 320. In this manner, as a result of that the second longitudinal member 330 restricts the bend of the first longitudinal member 320, the stiffness changing device 310 is in the high stiffness state, i.e. the hard state.

In the low stiffness state, the non-bend-restriction portion 332 of the second longitudinal member 330 is disposed in the range including the low flexural stiffness portion 324 of the first longitudinal member 320. Compared to the bend-restriction portion 334, the non-bend-restriction portion 332 has a lower degree by which the non-bend-restriction portion 332 restricts the bend of the low flexural stiffness portion 324 of the first longitudinal member 320. Thus, the stiffness changing device 310 is in the low stiffness state, i.e. the soft state, in which the stiffness changing device 310 is easily bendable at the low flexural stiffness portion 324.

According to another point of view, the first longitudinal member 320 includes a restricted portion 342 in which bending is restricted by the bend-restriction portion 334 in the high stiffness state. The restricted portion 342 includes a portion 344 of a first high flexural stiffness portion 322 of the first longitudinal member 320, the low flexural stiffness portion 324 neighboring the first high flexural stiffness portion 322, and a portion 346 of a second high flexural stiffness portion 322 that, together with the first high flexural stiffness portion 322, sandwiches the low flexural stiffness portion 324. In other words, the restricted portion 342 includes a low flexural stiffness portion 324, a portion 344 of a high flexural stiffness portion 322 located on one side of the low flexural stiffness portion 324, e.g. on the left side in FIG. 4, and a portion 346 of a high flexural stiffness portion 322 located on the other side of the low flexural stiffness portion 324, e.g. on the right side in FIG. 4. The length of the restricted portion 342, i.e. the dimension of the restricted portion 342 along the axis of the first longitudinal member 320, is equal to the length of the bend-restriction portion 334, i.e. the dimension of the bend-restriction portion 334 along the axis of the second longitudinal member 330.

When the bend-restriction portion 334 is located at a position corresponding to the restricted portion 342, the bend-restriction portion 334 restricts the bend of the low flexural stiffness portion 324. On the other hand, when the non-bend-restriction portion 332 is located at a position corresponding to the restricted portion 342, the non-bend-restriction portion 332 less restricts the bend of the low flexural stiffness portion 324 than when the bend-restriction portion 334 is located at the position corresponding to the restricted portion 342. Accordingly, when the bend-restriction portion 334 is located at the position corresponding to the restricted portion 342, the flexural stiffness of the stiffness changing device 310 in the region of the restricted portion 342 is higher than when the non-bend-restriction portion 332 is located at the position corresponding to the restricted portion 342.

A gap is provided between the first longitudinal member 320 and the bend-restriction portion 334 of the second longitudinal member 330. In this case, in the high stiffness state, when the magnitude of bend of the restricted portion 342 becomes equal to or higher than a restriction occurrence point that is a specific magnitude of bend, the bend-restriction portion 334 restricts an increase of bend of the restricted portion 342, and enhances the flexural stiffness of the stiffness changing device 310 at the restricted portion 342. As a result, although the flexural stiffness of the stiffness changing device 310 remains low at the beginning of bending, the flexural stiffness sharply increases when the bend increases by a predetermined magnitude or more and thereby the gap no longer exists.

In this manner, the relative movement between the first longitudinal member 320 and second longitudinal member 330 allows the stiffness of the stiffness changing device 310 to be switched between the high stiffness state, i.e. the hard state, and the low stiffness state, i.e. the soft state.

In the low stiffness state, the first longitudinal member 320 is easily bendable in the low flexural stiffness portion 324. By contrast, in the high stiffness state, the first longitudinal member 320 is less easily bendable even in the low flexural stiffness portion 324. Accordingly, it can be said that the switching between the low stiffness state and the high stiffness state in the stiffness changing device 310 is a movement of locking or unlocking a joint.

[Configuration Example 3 of Stiffness Control System]

Figure 5:
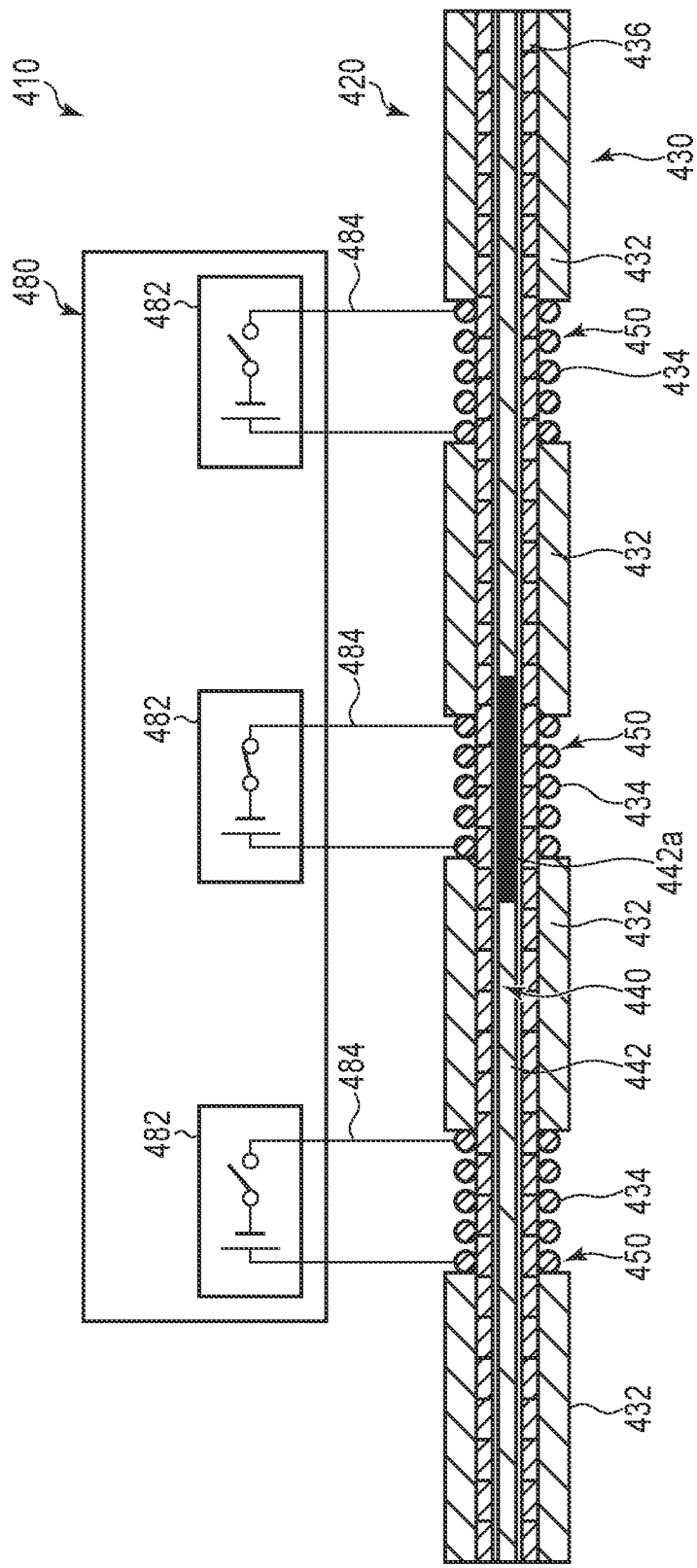
FIG. 5 shows a stiffness control system according to another configuration example of the stiffness control system shown in FIG. 2.

FIG. 5 shows a stiffness control system 410 according to another configuration example of the stiffness control system 80. As illustrated in FIG. 5, the stiffness control system 410 includes a stiffness changing device 420 that is to be attached to the soft tube 24c, and a control device 480 configured to control the stiffness changing device 420. In a shape memory member 442, a part (to-be-heated portion 442a) that is in the high stiffness state (hard state) is indicated by solid paint in black.

The stiffness changing device 420 provides different stiffness to the soft tube 24c to change the stiffness of the soft tube 24c. The stiffness changing device 420 includes a first-longitudinal member 430, a second longitudinal member 440 disposed along the first longitudinal member 430, and inducers 450. For example, the first longitudinal member 430 is an outer cylinder, and the second longitudinal member 440 is a core member disposed inside the first longitudinal member 430. For example, the cross-sectional shape of the outer cylinder perpendicular to the longitudinal axis of outer cylinder is an annular shape, and the outer periphery in cross section of the core member perpendicular to the longitudinal axis of the core member is a circular shape. In this case, the stiffness changing device 420 provides a stable flexural stiffness with respect to bending in all directions.

The first longitudinal member 430 includes at least one high flexural stiffness portion 432 with a relatively high flexural stiffness, and at least one low flexural stiffness portion 434 with a relatively low flexural stiffness. Specifically, the flexural stiffness of the high flexural stiffness portion 432 is high, and the flexural stiffness of the low flexural stiffness portion 434 is lower than the flexural stiffness of the high flexural stiffness portion 432. The first longitudinal member 430 further includes a cylindrical outer support member 436 supporting the high flexural stiffness portion 432 and low flexural stiffness portion 434. The flexural stiffness of the outer support member 436 is lower than the flexural stiffness of the high flexural stiffness portion 432. Thus, the first longitudinal member 430 is relatively easily bendable at the low flexural stiffness portion 434, and is relatively less easily bendable at the high flexural stiffness portion 432.

The high flexural stiffness portion 432, low flexural stiffness portion 434, and outer support member 436 are separate from each other. The high flexural stiffness portion 432 is composed of, for example, a cylindrical member such as a metallic pipe. The low flexural stiffness portion 434 is composed of, for example, a coil member such as a non-densely wound coil. The outer support member 436 is composed of, for example, a coil member such as a densely wound coil. The high flexural stiffness portion 432 is a cylindrical hard portion having a high flexural stiffness, and the low flexural stiffness portion 434 and outer support member 436 are cylindrical soft portions with low flexural stiffness.

The outer support member 436 is disposed inside the high flexural stiffness portion 432 and low flexural stiffness portion 434. An outer peripheral surface of the outer support member 436 is fixed by adhesion to an inner peripheral surface of the high flexural stiffness portion 432. The high flexural stiffness portions 432 are arranged at intervals in the longitudinal axis direction of the first longitudinal member 430. The low flexural stiffness portions 434 are arranged in spaces between the high flexural stiffness portions 432 in the longitudinal axis direction of the first longitudinal member 430. Accordingly, the high flexural stiffness portions 432 and the low flexural stiffness portion 434 are alternately arranged in the longitudinal axis direction of the first longitudinal member 430. An end portion of the low flexural stiffness portion 434 is fixed to an end portion of the high flexural stiffness portions 432 that neighbors the end portion of the low flexural stiffness portion 434. The low flexural stiffness portion 434 is wound around the outer support member 436 in the space between the high flexural stiffness portions 432.

The outer support member 436 extends over the entire length of the stiffness changing device 420. The outer support member 436 is helically disposed. For example, the outer support member 436 functions as a core member for the high flexural stiffness portions 432 and low flexural stiffness portion 434.

The second longitudinal member 440 extends over the entire length of the stiffness changing device 420. The second longitudinal member 440 is disposed inside the outer support member 436. An outer peripheral surface of the second longitudinal member 440 is not in contact with an inner peripheral surface of the outer support member 436, and a space is formed between the outer support member 436 and the second longitudinal member 440.

The second longitudinal member 440 includes at least a shape memory member 442 capable of transitioning in phase by heat between a first phase and a second phase. When the phase of the shape memory member 442 is the first phase, the shape memory member 442 takes a low stiffness state in which the shape memory member 442 can easily deform in accordance with external force, and exhibits a low elastic coefficient. Accordingly, when the phase of the shape memory member 442 is the first phase, the shape memory member 442 provides a relatively low stiffness to the soft tube 24c. In the first phase, the stiffness changing device 420 and the soft tube 24c can easily bend, for example, by external force.

When the phase of the shape memory member 442 is the second phase, the shape memory member 442 takes a high stiffness state having a higher stiffness than the low stiffness state, and exhibits a high elastic coefficient. Accordingly, when the phase of the shape memory member 442 is the second phase, the shape memory member 442 takes a high stiffness state indicative of a tendency that the shape memory member 442 takes a memorized shape that is memorized in advance against external force, and provides a relatively high stiffness to the soft tube 24c. The memorized shape may be, for example, a linear shape. In the second phase, the stiffness changing device 420 and the soft tube 24c can maintain, for example, a substantially linear state, or can be bent more gently by external force than in the first phase.

When the phase of the shape memory member 442 is the first phase, the flexural stiffness of the shape memory member 442 is lower than the flexural stiffness of the high flexural stiffness portion 432 and is equal to or lower than the flexural stiffness of the low flexural stiffness portion 434. When the phase of the shape memory member 442 is the second phase, the flexural stiffness of the shape memory member 442 is equal to or lower than the flexural stiffness of the high flexural stiffness portion 432 and is higher than the flexural stiffness of the low flexural stiffness portion 434.

The low flexural stiffness portion 434 is composed of an electrically conductive material. The low flexural stiffness portion 434 may be, for example, a heating wire, i.e. an electrically conductive member with a high electrical resistance. For example, an insulating film (not shown) is provided around the low flexural stiffness portion 434. The insulating film prevents short-circuit between the low flexural stiffness portion 434 and the outer support member 436, and short-circuit between the high flexural stiffness portion 432 and the low flexural stiffness portion 434.

For example, an insulating film (not shown) is provided around the outer support member 436. The insulating film prevents short-circuit between the low flexural stiffness portion 434 and the outer support member 436, short-circuit between the high flexural stiffness portion 432 and the outer support member 436, and short-circuit between the outer support member 436 and the shape memory member 442.

The inducer 450 has a capability of generating heat by receiving the supply of current from the control device 480. The inducer 450 transmits the heat to a part of the shape memory member 442, the part being located near the inducer 450. In addition, in this part, the inducer 450 induces the shape memory member 442 to transition in phase between the first phase and the second phase. The inducer 450 changes the stiffness of a part of the second longitudinal member 440 in the longitudinal axis direction of the second longitudinal member 440.

The control device 480 includes driving units 482 configured to independently drive the low flexural stiffness portions 434. The driving unit 482 includes a power source and a switch. The driving unit 482 is electrically connected across the low flexural stiffness portion 434 through wirings 484. The driving unit 482 supplies current to the low flexural stiffness portion 434 through the wirings 484 in accordance with an ON operation of the switch, and stops the supply of current to the low flexural stiffness portion 434 in accordance with an OFF operation of the switch.

The low flexural stiffness portion 434 has a capability of generating heat in accordance with the supply of current from the control device 480. The heat generation quantity of the low flexural stiffness portion 434 depends on the supply quantity of current. The low flexural stiffness portion 434 functions as the inducer 450 configured to induce the shape memory member 442 by heat to transition in phase between the first phase and the second phase. To be more specific, the low flexural stiffness portion 434 functions as a coil heater that is a heating unit that is configured to heat the shape memory member 442 through the outer support member 436. The shape memory member 442 has a characteristic of transitioning in phase from the first phase to the second phase by the heat generated from the low flexural stiffness portion 434 functioning as the inducer 450.

In the stiffness control system 410, in the initial state, the driving unit 482 does not supply current to the low flexural stiffness portion 434, so that the low flexural stiffness portion 434 generates no heat, and the shape memory member 442 and the soft tube 24c are in the low stiffness state over the entire length.

The driving unit 482 supplies current to the low flexural stiffness portion 434 through the wirings 484 in accordance with the ON operation of the switch. The low flexural stiffness portion 434 generates heat in accordance with the supply of current. The heat is indirectly transmitted from the low flexural stiffness portion 434 to the shape memory member 442. The transmission of heat raises the temperature of the to-be-heated portion 442a of the shape memory member 442. The phase of the to-be-heated portion 442a changes from the first phase to second phase by the heating, and the to-be-heated portion 442a is switched from the low stiffness state to the high stiffness state. Thereby, the soft tube 24c is partly switched from the low stiffness state to the high stiffness state. The part of the soft tube 24c that is in the high stiffness state maintains a substantially linear state against the external force acting on the soft tube 24c, i.e. the force that can deform the shape memory member 442.

The driving unit 482 stops the supply of current to the low flexural stiffness portion 434 in accordance with the OFF operation of the switch. Then, the temperature of the to-be-heated portion 442a lowers by natural cooling, the phase of the to-be-heated portion 442a changes from the second phase to the first phase, and the stiffness of the to-be-heated portion 442a lowers. Further, the stiffness of the part of the soft tube 24c at which the to-be-heated portion 442a is located also lowers. Accordingly, the soft tube 24c can easily be bent by external force.

In this manner, the phase of a part of the shape memory member 442 is switched between the first phase and the second phase by, for example, the low flexural stiffness portion 434, so that the stiffness of a part of the soft tube 24c is switched.

[Configuration Example 4 of Stiffness Control System]

Figure 6:
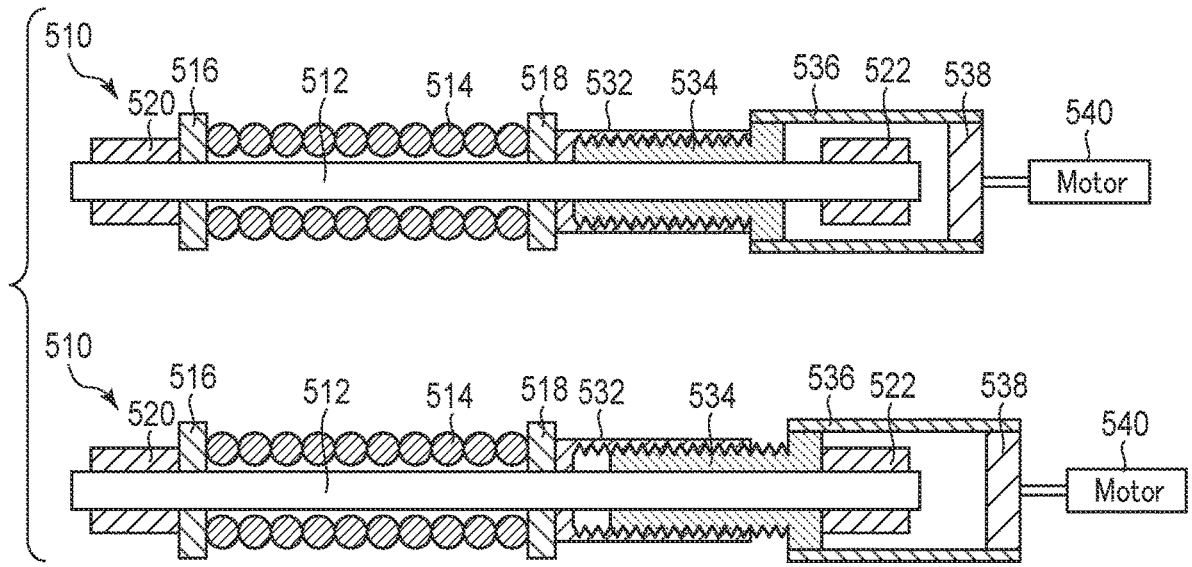
FIG. 6 shows a basic configuration of a stiffness changing device in another configuration example of the stiffness control system shown in FIG. 2.

FIG. 6 shows a basic configuration of a stiffness changing device 510 according to another configuration example of the stiffness control system 80. An upper part of FIG. 6 shows the stiffness changing device 510 in a low flexural stiffness state, and a lower part of FIG. 6 shows the stiffness changing device 510 in a high flexural stiffness state.

The stiffness changing device 510 includes a coil pipe 514 with flexibility, for example, a densely wound coil; a core 512 extending in the inside of the coil pipe 514; and a pair of stationary members 520 and 522 that are disposed on both sides of the coil pipe 514 and are fixed to the core 512.

A washer 516 is disposed between the coil pipe 514 and the stationary member 520. A washer 518 is disposed between the coil pipe 514 and the stationary member 522. The washers 516 and 518 function to restrict the movement of the coil pipe 514 along the core 512. The washers 516 and 518 prevent the coil pipe 514 from dropping off the core 512, and prevent the stationary members 520 and 522 from biting into the coil pipe 514.

The stiffness changing device 510 also includes an adjusting mechanism configured to adjust gaps between the coil pipe 514 and the stationary members 520 and 522. The adjusting mechanism is composed of a pulling mechanism configured to pull at least one of the paired stationary members 520 and 522 in a direction in which the paired stationary members 520 and 522 move away from each other. The pulling mechanism includes a nut 532, a lead screw 534 that is screwed with the nut 532, a cylindrical body 536 fixed to the lead screw 534, a cover 538 fixed to the cylindrical body 536, and a motor 540 configured to rotate the lead screw 534.

The core 512 extends through the nut 532 and lead screw 534. The stationary member 522 is contained in the cylindrical body 536. The motor 540 is supported so that the motor 540 itself does not rotate and is movable in the axial direction. Rotating the lead screw 534 relative to the nut 532 by the motor 540 causes the lead screw 534 to move along the axis of the core 512.

In the state shown in the upper part of FIG. 6, there is a gap between the lead screw 534 and the stationary member 522. In this state, the core 512 is movable along the coil pipe 514. This state is a state with low flexural stiffness because no tensile stress acts on the core 512 when the coil pipe 514 is bent. The stiffness changing device 510 that is in the low flexural stiffness provides a low stiffness to the soft tube 24c on which the stiffness changing device 510 is attached.

On the other hand, in the state shown in the lower part of FIG. 6, there is no gap between the lead screw 534 and the stationary member 522. In this state, the core 512 is immovable relative to the coil pipe 514. In addition, the lead screw 534 pushes the stationary member 522, so that tensile stress acts on the core 512. This state is a state with high flexural stiffness because tensile stress acts on the core 512 when the coil pipe 514 is bent. The stiffness changing device 510 that is in the high flexural stiffness provides a high stiffness to the soft tube 24c on which the stiffness changing device 510 is attached.

[Configuration Example 5 of Stiffness Control System]

Figure 7:
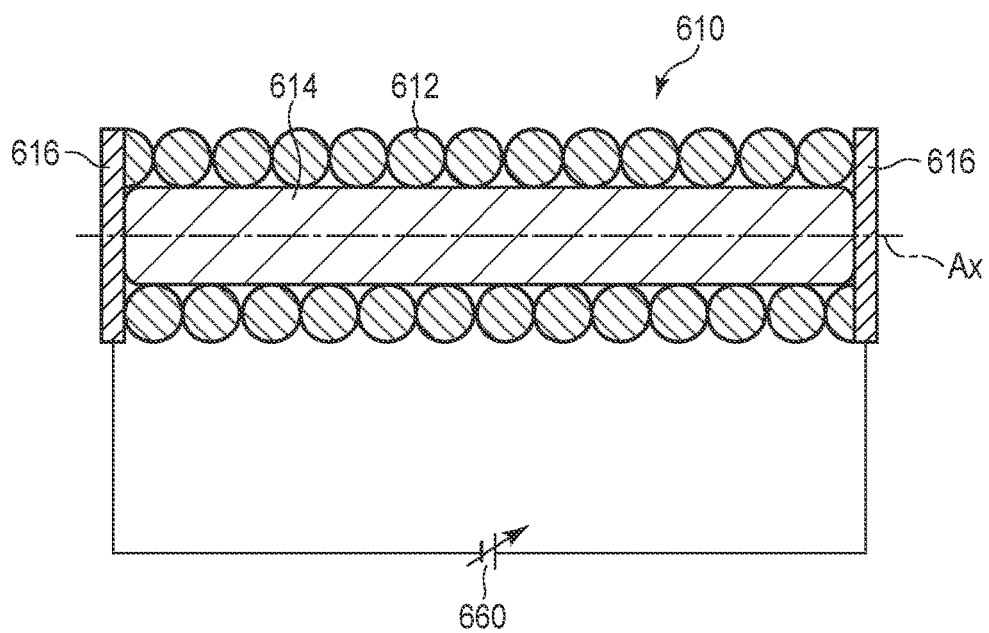
FIG. 7 schematically shows a stiffness changing device and a stiffness control circuit in another configuration example of the stiffness control system shown in FIG. 2.

FIG. 7 schematically shows a stiffness changing device 610 and a stiffness control circuit 660 according to another configuration example of the stiffness control system 80. As shown in FIG. 7, the stiffness changing device 610 includes a coil pipe 612, a conducting-polymer artificial muscle 614 located in the coil pipe 612, and a pair of electrodes 616 provided on both ends of the coil pipe 612. The stiffness changing device 610 is built in the soft tube 24c so that a center axis Ax of the coil pipe 612 coincides with, or is parallel to, a center axis of the soft tube 24c.

The electrodes 616 of the stiffness changing device 610 are electrically connected across the stiffness control circuit 660. The stiffness control circuit 660 applies voltage to the conducting-polymer artificial muscle 614 through the electrodes 616. The application of voltage causes the conducting-polymer artificial muscle 614 to try to expand its diameter about the center axis Ax of the coil pipe 612, but the expansion of the diameter of the conducting-polymer artificial muscle 614 is restricted by the coil pipe 612. Thus, as the value of applied voltage becomes higher, the flexural stiffness of the stiffness changing device 610 increases. Specifically, changing the stiffness of the stiffness changing device 610 also changes the flexural stiffness of the soft tube 24c, in which the stiffness changing device 610 is built.

[Configuration Example 1 of Shape Calculation System]

Figure 8:
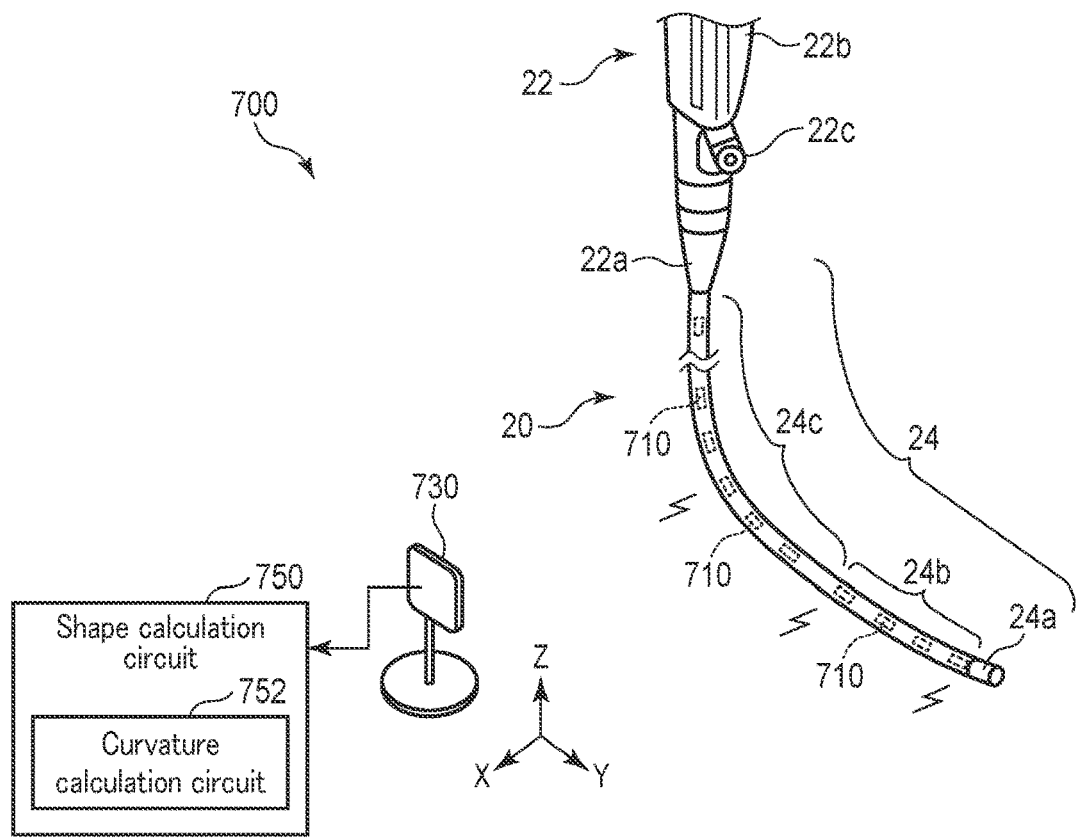
FIG. 8 schematically shows a shape calculation system according to a configuration example of a shape calculation system shown in FIG. 2.

A configuration example of the shape calculation system 90 will be described. FIG. 8 schematically shows a shape calculation system 700 according to the present configuration example. The shape calculation system 700 includes a large number of position sensors 710 that are built in at intervals along the longitudinal axis of the insertion section 24. The position sensors 710 constitute the shape sensor 92 in the shape calculation system 90. As the position sensors 710, there are known magnetic-type, ultrasonic-type, and optical-type position sensors. For example, the position sensor 710 is composed of a magnetic coil. The magnetic coil is a magnetic field generating element configured to generate a magnetic field.

FIG. 8 schematically shows an example in which the position sensors 710 are composed of magnetic coils. The shape calculation system 90 includes an antenna 730 configured to receive signals from the position sensors 710, i.e. magnetic fields generated by the magnetic field generating elements. The antenna 730 is separate from the endoscope 20, and is fixed to a vicinity of an observation target into which the insertion section 24 of the endoscope 20 is inserted. The antenna 730 is connected to a shape calculation circuit 750.

Based on signals, i.e. information of magnetic fields, received by the antenna 730, the shape calculation circuit 750 calculates positions of the position sensors 710 in a coordinate space determined based on the antenna 730. Further, based on the information of positions of the position sensors 710, the shape calculation circuit 750 calculates a bend shape of the insertion section 24, for example, by interpolating coordinates of the positions of the position sensors 710. The shape calculation circuit 750 includes, if necessary, a curvature calculation circuit 752 configured to calculate the curvature of each of various portions of the insertion section 24 at which many position sensors 710 are built.

Accordingly, the shape calculation system 700 can recognize a spatial position, i.e. a three-dimensional position, of each of various portions of the insertion section 24 relative to a predetermined reference point.

[Configuration Example 2 of Shape Calculation System]

Figure 9:
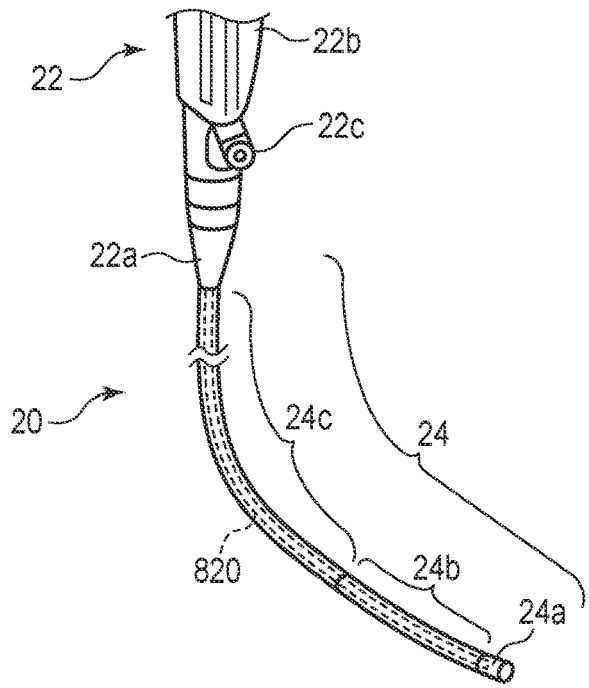
FIG. 9 shows another configuration example of a shape sensor of the shape calculation system shown in FIG. 2.

FIG. 9 shows another configuration example of the shape sensor 92 of the shape calculation system 90. In this configuration example, the shape sensor 92 includes a fiber sensor 820 provided along the longitudinal direction of the insertion section 24.

Figure 10:
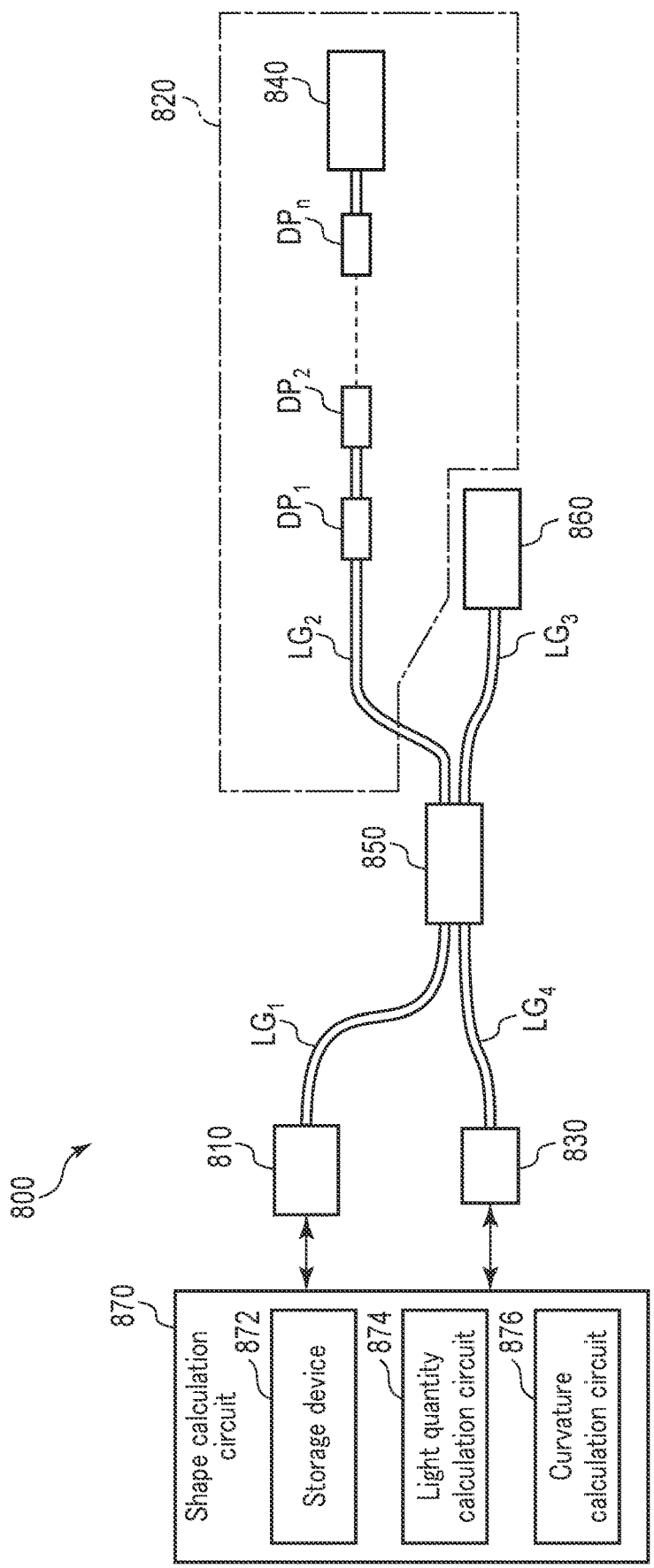
FIG. 10 shows a configuration of the shape calculation system including a fiber sensor shown in FIG. 9.

FIG. 10 shows a configuration of a shape calculation system 800 including the fiber sensor 820. The shape calculation system 800 includes the fiber sensor 820 assembled in the insertion section 24; a light source 810 configured to supply light to the fiber sensor 820; a light detector 830 configured to detect light that has passed through the fiber sensor 820; a light branching element 850 configured to guide light from the light source 810 to the fiber sensor 820 and to guide light from the fiber sensor 820 to the light detector 830; an antireflection member 860 connected to the light branching element 850; and a shape calculation circuit 870 configured to calculate the shape of the fiber sensor 820.

The fiber sensor 820 includes a light guide member $GL_2$ connected to the light branching element 850; bend sensors $DP_i$ (i=1, 2, ..., n) provided on the light guide member $GL_2$; and a reflection member 840 provided on an end portion of the light guide member $GL_2$.

Each bend sensor $DP_i$ is composed of a material configured to reduce the quantity of light guided by the light guide member $GL_2$. The bend sensors $DP_i$ have functions of reducing the quantity of light of different wavelengths. Specifically, different bend sensors $DP_i$ have mutually different light absorption characteristics. Each bend sensor $DP_i$ is composed of, for example, a light absorber whose light absorptivity for light passing through each bend sensor $DP_i$ varies in accordance with a direction of bend and a curvature of bend. The light guide member $GL_2$ is composed of an optical fiber and has flexibility. The fiber sensor 820 is composed of a fiber sensor including an optical fiber on which the bend sensors $DP_i$ are provided.

The reflection member 840 has a function of reflecting light guided by the light guide member $GL_2$ from the light branching element 850 so as to return the light toward the light branching element 850.

The light source 810 is optically connected to the light branching element 850 through a light guide member $GL_1$. The light detector 830 is optically connected to the light branching element 850 through a light guide member $GL_4$. The antireflection member 860 is optically connected to the light branching element 850 through a light guide member $GL_3$. The light guide members $GL_1$, $GL_3$, and $GL_4$ are composed of, for example, optical fibers, and have flexibility.

The light source 810 has a function of supplying light to the fiber sensor 820. The light source 810 includes, for example, a generally known light emitting element such as a lamp, an LED, a laser diode, or the like.

The light branching element 850 guides light from the light source 810 to the fiber sensor 820 and guides light from the fiber sensor 820 to the light detector 830. The light branching element 850 includes an optical coupler, a halfmirror, etc. For example, the light branching element 850 divides the light emitted from the light source 810 and input through the light guide member $LG_1$, and guides the divided light to two light guide members $LG_2$ and $LG_3$. In addition, the light branching element 850 guides reflected light from the reflection member 840, which is input through the light guide member $LG_2$, to the light detector 830 through the light guide member $LG_4$.

The light detector 830 has a function of detecting light that has passed through the fiber sensor 820. The light detector 830 has a function of detecting the quantity of received light for each wavelength, i.e. a function of spectrally separating and detecting light. The light detector 830 detects the quantity of light in a predetermined wavelength range to output detection information. Here, the detection information is information representative of a relationship between a specific wavelength in the predetermined wavelength range and the quantity of light of the specific wavelength.

Detection light guided by the light guide member $LG_2$ is lost at the bend sensor $DP_i$. The loss quantity of the guided light varies in accordance with the direction of bend of the light guide member $LG_2$ and the quantity of the bend, as shown in FIG. 11A to FIG. 11C.

Figure 11A:
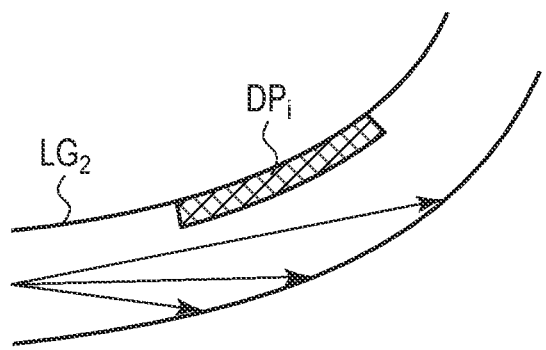
FIG. 11A is a view for describing the shape calculation system shown in FIG. 10, and schematically shows transmission of light when a light guide member is bent so that a bend sensor is located in the inside of bend of the light guide member.
Figure 11B:
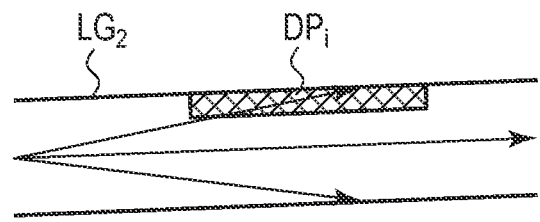
FIG. 11B is a view for describing the shape calculation system shown in FIG. 10, and schematically shows transmission of light when the light guide member is not bent.

For example, when the light guide member $LG_2$ is bent so that the bend sensor $DP_i$ is at the inside of the bend of the light guide member $LG_2$, as shown in FIG. 11A, the guided light loss quantity is less than when the light guide member $LG_2$ is not bent as shown in FIG. 11B. In addition, the guided light loss quantity becomes smaller in accordance with a bend quantity, i.e. a curvature, of the light guide member $LG_2$.

Figure 11C:
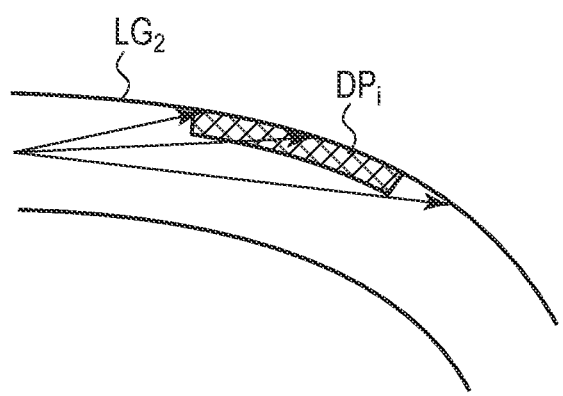
FIG. 11C is a view for describing the shape calculation system shown in FIG. 10, and schematically shows transmission of light when the light guide member is bent so that the bend sensor is located on the outside of bend of the light guide member.

Conversely, when the light guide member $LG_2$ is bent so that the bend sensor $DP_i$ is at the outside of the bend of the light guide member $LG_2$, as shown in FIG. 11C, the guided light loss quantity is greater than when the light guide member $LG_2$ is not bent as shown in FIG. 11B. In addition, the guided light loss quantity becomes greater in accordance with a bend quantity, i.e. a curvature, of the light guide member $LG_2$.

The variation of the guided light loss quantity is reflected on the quantity of detection light received by the light detector 830. Specifically, the variation of the guided light loss quantity is reflected on detection information from the light detector 830. Accordingly, monitoring the detection information from the light detector 830 allows recognizing the direction and quantity of the bend of the light guide member $LG_2$.

In FIG. 10, the light emitted from the light source 810 is guided by the light guide member $LG_1$ and enters the light branching element 850. The light branching element 850 divides the input light and outputs the divided light to two light guide members $LG_2$ and $LG_3$.

The light guided by the light guide member $LG_3$ is, for example, absorbed by the antireflection member 860 provided on an end portion of the light guide member $LG_3$.

The light guided by the light guide member $LG_2$ is reflected by the reflection member 840 provided on an end portion of the light guide member $LG_2$, and is then guided by the light guide member $LG_2$ and returned to the light branching element 850. While light is being guided by the light guide member $LG_2$, a wavelength component of the light, which corresponds to the bend sensor $DP_i$, is lost by the bend sensor $DP_i$.

The light branching element 850 divides the returned light, and outputs part of the light to the light guide member $LG_4$. The light output to the light guide member $LG_4$ is guided by the light guide member $LG_4$ and enters the light detector 830. The light received by the light detector 830 is light that has passed through the bend sensor $DP_i$, and the quantity of light varies depending on the curvature of the bend sensor $DP_i$.

Based on the detection information from the light detector 830, the shape calculation circuit 870 calculates the shape of the light guide member $LG_2$ of the fiber sensor 820.

The shape calculation circuit 870 includes a storage device 872, a light quantity calculation circuit 874, and a curvature calculation circuit 876.

The storage device 872 stores a light quantity calculation relationship representative of a relationship among the shape, wavelength, and light quantity for the bend sensors $DP_i$. The storage device 872 also stores various kinds of information necessary for calculation performed by the shape calculation circuit 870, such as information of positions of the bend sensors $DP_i$.

The light quantity calculation circuit 874 calculates light quantity information from the detection information from the light detector 830, and transmits the calculated light quantity information to the curvature calculation circuit 876.

The curvature calculation circuit 876 reads out the light quantity calculation relationship from the storage device 872, and calculates, based on the read-out light quantity calculation relationship, a light quantity calculation value representative of the relationship between a wavelength and a light quantity corresponding to each bend sensor $DP_i$. The curvature calculation circuit 876 further calculates the curvature of each of the bend sensors $DP_i$, based on the calculated light quantity calculation value, and the light quantity information supplied from the light quantity calculation circuit 874.

The shape calculation circuit 870 reads out the information of the position of each bend sensor $DP_i$ from the storage device 872, and calculates shape information of the light guide member $LG_2$, in which the bend sensors $DP_i$ are provided, based on the read-out information of the position, and the curvature of each bend sensor $DP_i$ calculated by the curvature calculation circuit 876. The shape calculation circuit 870 outputs the calculated shape information of the light guide member $LG_2$ as the information of the bend shape of the insertion section 24, in which the fiber sensor 820 including the light guide member $LG_2$ is assembled.

Accordingly, the shape calculation system 800 can recognize a three-dimensional position of each of various portions of the insertion section 24, with the three-dimensional position and direction of a specific location of the insertion section 24 being set as a reference. Specifically, the shape calculation system 800 can recognize the three-dimensional position of each of various portions of the insertion section 24, relative to a predetermined reference position, by detecting the three-dimensional position and direction of a specific location of the insertion section 24 relative to the predetermined reference position.

[Insertion Support Operation]

Next, an insertion support operation of the insertion section 24 in the flexible tube insertion apparatus 10 will be described. Hereinafter, the description will be given on the assumption that the endoscope 20 is a colonoscope and the tract of the observation target is the large intestine of a patient. In the stiffness control system 80, in the initial state, all stiffness changing devices 82 are controlled to be in the soft state. Thus, the soft tube 24c is in a state in which the soft tube 24c is most easily bent.

The insertion section 24 of the endoscope 20 is inserted from the anus into the large intestine. The insertion section 24 inserted in the large intestine is advanced, by the operator's pushing operation, from the anus to the rectum and further to the colon. The insertion section 24 advanced in the large intestine moves into the large intestine while the soft tube 24c is bending in accordance with the bend shape of the large intestine.

The image processing circuit of the imaging system 70 processes an image signal acquired by the imaging element 72 provided in the hard distal section 24a of the insertion section 24 of the endoscope 20, and causes the display 40 to display an optical image of the inner wall of the large intestine.

There is a case in which the insertion section 24 advanced in the large intestine receives strong resistance from the large intestine. In this case, if the pushing operation is further continued, there is a possibility that a buckling occurs in the insertion section 24 in a part in rear of the part that receives the strong resistance. The buckling is a phenomenon in which, despite the insertion section 24 being pushed into the large intestine, the hard distal section 24a does not advance and a portion of the soft tube 24c is considerably bent.

Normally, in this case, in order to eliminate the buckling, an operation is performed to pull back the insertion section 24 inserted in the large intestine. Subsequently, after the buckling is assumed to have been eliminated, the pushing operation is performed once again, and an operation is attempted to push and advance the insertion section 24 into the large intestine.

By a single pulling operation and a subsequent further pushing operation, the insertion section 24 may be advanced deeper into the large intestine, but a buckling may occur once again at the time of the subsequent pushing operation. In this case, by repeating the series of the pulling operation and pushing operation, the insertion section 24 is advanced deeper into the large intestine.

The flexible tube insertion apparatus 10 according to the present embodiment performs the insertion support operation that supports the insertion of the insertion section 24 by reducing the occurrence of a buckling at the time of the further pushing operation after the occurrence of the buckling.

FIG. 12 shows a flowchart of a process in the insertion support operation of the insertion section 24 in the flexible tube insertion apparatus 10. The process of FIG. 12 is mainly executed by the stiffness control system 80, the buckling detection system 110 and the pulling operation detection system 140. The flowchart of FIG. 12 shows a process from immediately after an insertion support operation function of the flexible tube insertion apparatus 10 is started, until the insertion support operation function of the flexible tube insertion apparatus 10 is stopped. The start and stop of the insertion support operation function is performed by, for example, the switch 22e of the operation unit 22.

Figure 13:
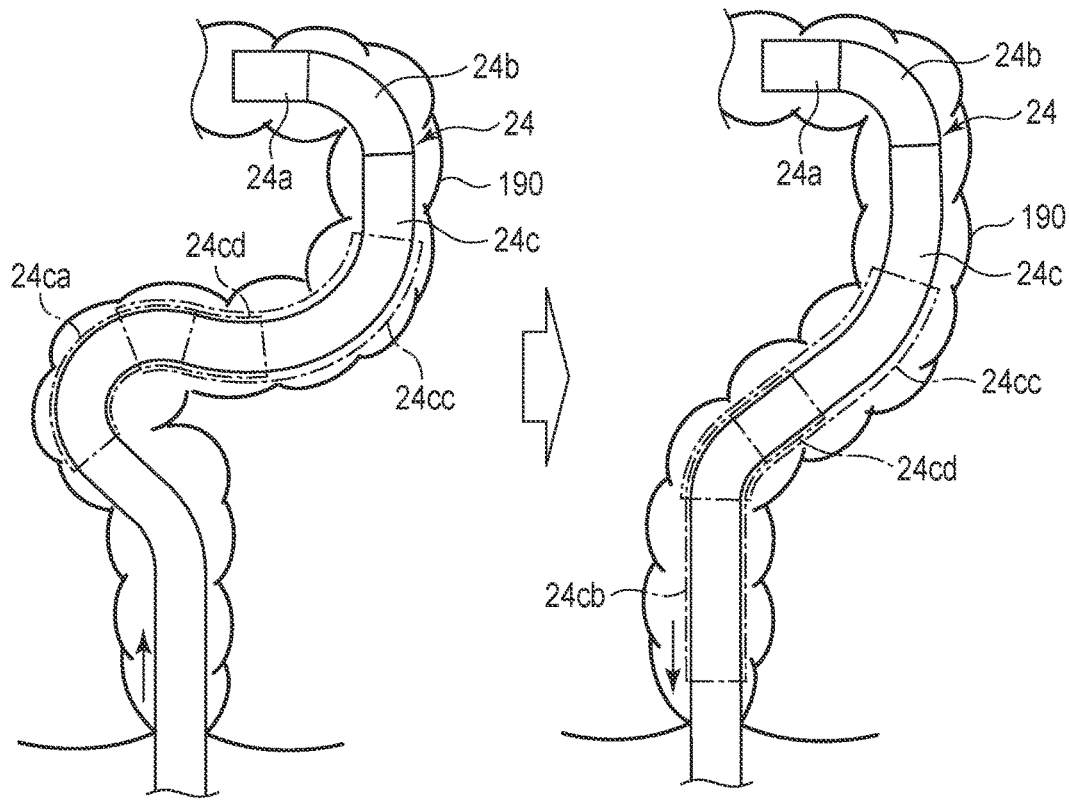
FIG. 13 shows the insertion section inserted in the large intestine.

In addition, FIG. 13 shows the insertion section 24 inserted in the large intestine 190. A left part of FIG. 13 shows the state in which a buckling occurs by a pushing operation, and a right part of FIG. 13 shows the state in which the buckling is eliminated by a pulling operation.

After the insertion support operation function of the flexible tube insertion apparatus 10 is started, the buckling detection system 110 starts monitoring of the occurrence of a buckling in the soft tube 24c of the insertion section 24. The monitoring of the generation of the buckling is performed by detecting whether or not a buckling occurs, for example, at predetermined time intervals. In step S1, the buckling detection system 110 detects whether or not a buckling occurs in the soft tube 24c. When it is not detected that a buckling occurs in the soft tube 24c, the process goes to step S4 of determining whether or not to stop the insertion support operation function.

When it is detected in step S1 that a buckling occurs in the soft tube 24c, the pulling operation detection system 140 detects in step S2 whether or not a sufficient pulling operation of the insertion section 24 is performed. The sufficient pulling operation means such a pulling operation of the insertion section 24 as to eliminate the buckling. In other words, the sufficient pulling operation means an operation of pulling the insertion section 24 with a pulling amount that is equal to or greater than such a pulling amount as to eliminate the buckling. The pulling operation detection system 140 may further detect whether or not the sufficient pulling operation is completed. When it is not detected that the sufficient pulling operation of the insertion section 24 is performed, the process goes to step S4 of determining whether or not to stop the insertion support operation function.

Further, if necessary, the buckling detection system 110 determines a portion of the soft tube 24c at which the stiffness is to be enhanced after the sufficient pulling operation. Hereinafter, for the purpose of convenience, the portion of the soft tube 24c at which the stiffness is to be enhanced after the sufficient pulling operation is simply referred to as "stiffness-to-be-enhanced portion 24cc". For example, as shown in FIG. 13, the stiffness-to-be-enhanced portion 24cc is a portion of the soft tube 24c that includes a portion on the distal side of a buckling portion 24ca. However, it is not always necessary that the stiffness-to-be-enhanced portion 24cc includes the portion on the distal side of the buckling portion 24ca. It suffices that the stiffness-to-be-enhanced portion 24cc includes at least a portion 24cd that neighbors the buckling portion 24ca of the soft tube 24c and is located on the distal side of the buckling portion 24ca. Furthermore, the stiffness-to-be-enhanced portion 24cc may include not a part of the buckling portion 24ca, but the entirety of the buckling portion 24ca. The buckling detection system 110 stores information of the stiffness-to-be-enhanced portion 24cc in a storage device 112. The information of the stiffness-to-be-enhanced portion 24cc is, for example, information indicative of a portion that the stiffness-to-be-enhanced portion 24cc occupies in the insertion section 24.

In step S2, when it is detected that a sufficient pulling operation of the insertion section 24 is performed, the stiffness control system 80 enhances, in step S3, the stiffness of the stiffness-to-be-enhanced portion 24cc. Hereinafter, for the purpose of convenience, to enhance the stiffness of the stiffness-to-be-enhanced portion 24cc is simply referred to as "stiffness enhancement". The stiffness enhancement of the soft tube 24c is performed by changing the state of the stiffness changing device 82 assembled in the soft tube 24c from the soft state to the hard state.

The stiffness-to-be-enhanced portion 24cc is, for example, a portion that is determined by the buckling detection system 110 as described above. In this case, the stiffness control system 80 enhances the stiffness of the stiffness-to-be-enhanced portion 24cc, based on the information stored in the storage device 112 in the buckling detection system 110. Specifically, the stiffness control circuit 86 reads out the information of the stiffness-to-be-enhanced portion 24cc from the storage device 112 in the buckling detection system 110, and changes the state of the stiffness changing device 82 corresponding to the stiffness-to-be-enhanced portion 24cc from the soft state to the hard state, based on the read-out information of the stiffness-to-be-enhanced portion 24cc.

Note that, as will be described later, when a portion where a second buckling will occur is predicted based on the position of the buckling portion, the stiffness-to-be-enhanced portion 24cc may be a portion determined based on the prediction. In this case, for example, the buckling detection system 110 determines that the stiffness-to-be-enhanced portion 24cc is a portion of the soft tube 24c that is located in an area where the occurrence of a second buckling is expected based on the position of the buckling portion, and supplies the position information of this portion to the stiffness control system 80. Based on the position information supplied from the buckling detection system 110, the stiffness control system 80 enhances the stiffness of the stiffness-to-be-enhanced portion 24cc.

The right part of FIG. 13 shows the insertion section 24 in the state in which the buckling is eliminated by a pulling operation. In the insertion section 24 in this state, the stiffness of a portion of the soft tube 24c that includes a distal-side portion of a buckling correspondence portion 24cb that corresponds to the buckling portion 24ca by the previous pushing operation is enhanced. It is thus possible to prevent the occurrence of a buckling in the soft tube 24c in a pushing operation that follows the pulling operation.

When it is not detected in step S1 that a buckling occurs in the soft tube 24c, or when it is not detected in step S2 that a sufficient pulling operation of the insertion section 24 is performed, it is determined in step S4 whether or not the stop of the insertion support operation function of the flexible tube insertion apparatus 10 is instructed. For example, the insertion control apparatus 30 performs this determination. Alternatively, one of the stiffness control system 80, buckling detection system 110, and pulling operation detection system 140 may perform this determination. In step S4, when it is determined that the stop of the insertion support operation function of the flexible tube insertion apparatus 10 is not instructed, the process returns to step S1. Conversely, in step S4, when it is determined that the stop of the insertion support operation function of the flexible tube insertion apparatus 10 is instructed, the insertion control apparatus 30 stops the insertion support operation function of the flexible tube insertion apparatus 10.

As is understood from the above description, in the flexible tube insertion apparatus 10, in the case where the occurrence of a buckling in the soft tube 24c is detected by the buckling detection system 10 and then it is detected by the pulling operation detection system 140 that a sufficient pulling operation is performed, the stiffness control system 80 enhances the stiffness of the stiffness-to-be-enhanced portion 24cc, which is a portion of the soft tube 24c that includes a distal-side portion of the buckling correspondence portion 24cb.

It is thus possible to prevent the occurrence of a buckling in the insertion section 24 in the next pushing operation following the pulling operation. In addition, the stiffness of a portion of the soft tube 24c that does not relate to the occurrence of the buckling is kept low as before. Therefore, the insertability of the insertion section 24 is improved. Besides, the pain of the patient is reduced.

Additionally, the stiffness enhancement of the soft tube 24c is performed after a buckling is eliminated by a sufficient pulling operation and the soft tube 24c is restored to the substantially straight state. Thus, there is hardly any change in shape of the insertion section 24 by the stiffness enhancement of the soft tube 24c. Therefore, the occurrence of an excessive load on the intestinal wall by a shape change due to the stiffness enhancement of the insertion section 24, which may otherwise occur, can be avoided.

[Configuration Example 1 of the Buckling Detection System]

Figure 14:
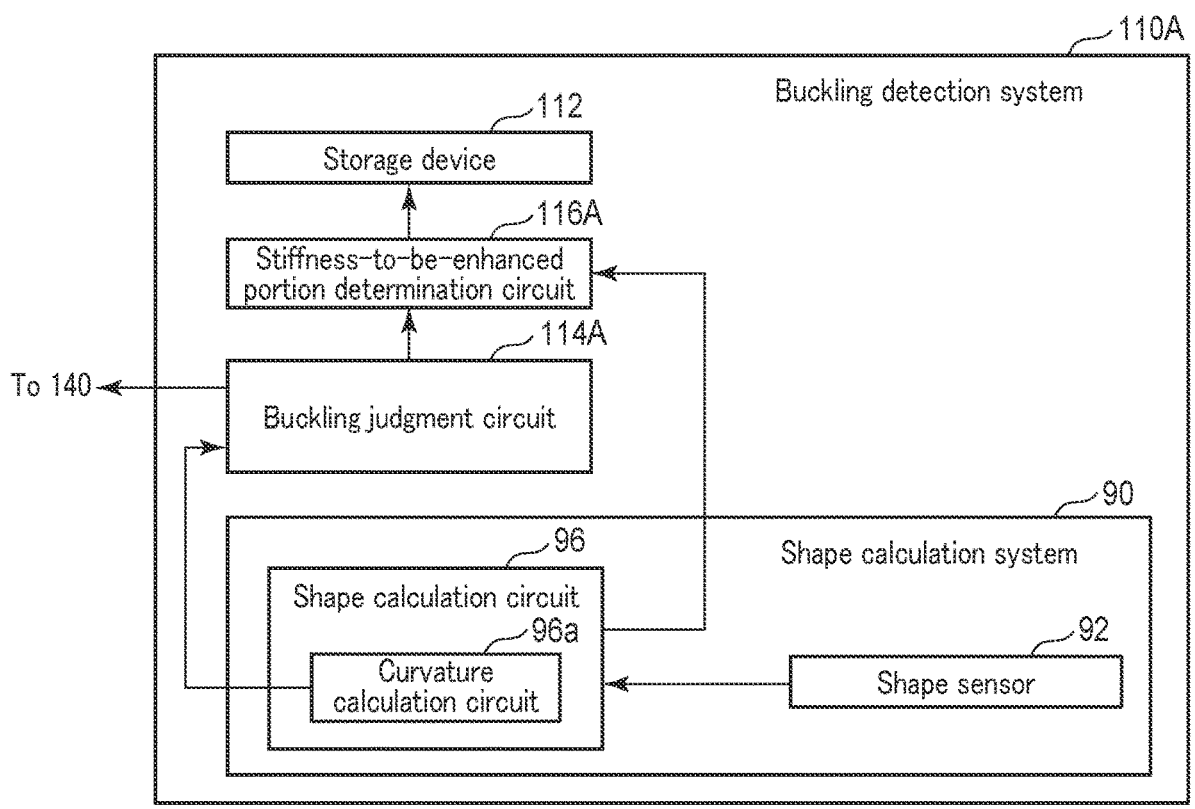
FIG. 14 schematically shows a buckling detection system according to a configuration example of a buckling detection system shown in FIG. 2.
Figure 15:
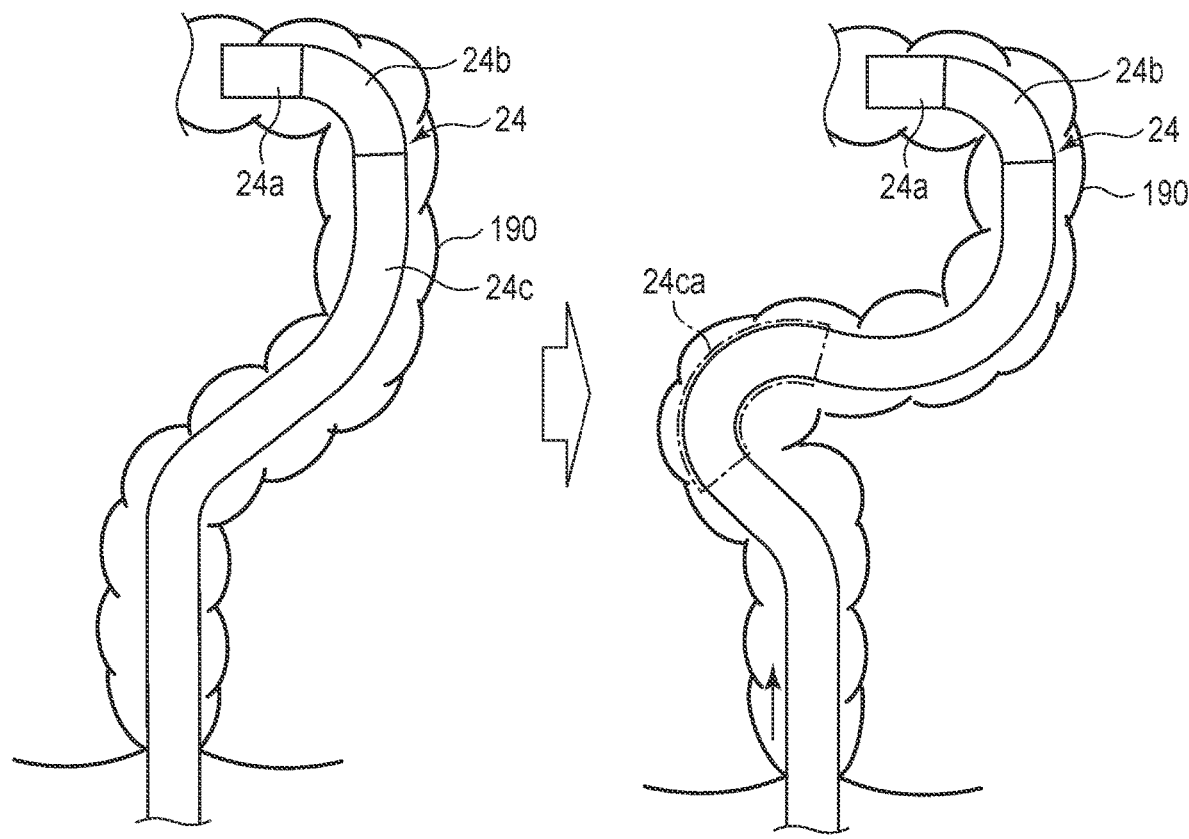
FIG. 15 shows a state in which a buckling occurs by a pushing operation of the insertion section.
Figure 16:
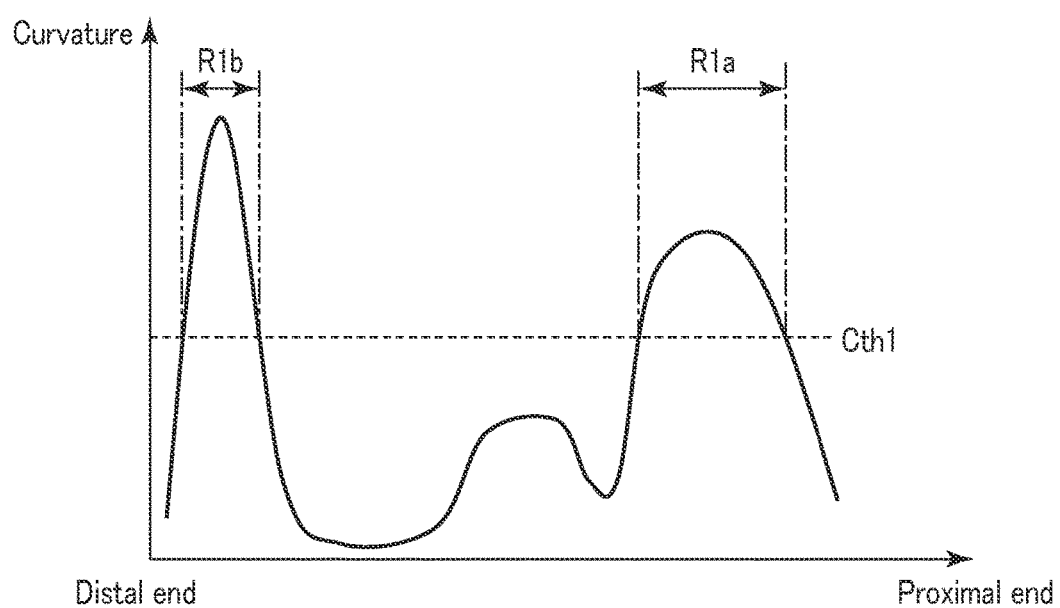
FIG. 16 is a graph showing curvatures of various portions of the insertion section in a state in which a buckling occurred, FIG. 16 being a graph for explaining the detection of buckling occurrence in the buckling detection system shown in FIG. 14.

A configuration example of the buckling detection system 110 will be described with reference to FIG. 14 to FIG. 16. FIG. 14 schematically shows a buckling detection system 110A according to the configuration example. The buckling detection system 110A is configured to detect the occurrence of a buckling in the soft tube 24c, based on the curvature of each of various portions of the soft tube 24c. FIG. 15 shows a state in which a buckling occurs by a pushing operation of the insertion section 24. A left part of FIG. 15 shows a state before the occurrence of a buckling, and a right part of FIG. 15 shows a state in which a buckling occurs by a pushing operation. FIG. 16 is a graph showing curvatures of various portions of the insertion section 24 inserted in the large intestine 190 in a state in which a buckling occurred. In FIG. 16, an ordinate axis indicates curvature, and an abscissa axis indicates a length from the distal end of the insertion section 24. In other graphs showing curvatures, which will be described below, the ordinate axis and abscissa axis indicate the same as in FIG. 16.

The buckling detection system 110A includes the shape calculation system 90. The shape calculation system 90 includes a curvature calculation circuit 96a configured to calculate the curvature of each of various portions of the insertion section 24. The curvature calculation circuit 96a corresponds to the curvature calculation circuit 752 of the shape calculation system 700 described with reference to FIG. 8, or the curvature calculation circuit 876 of the shape calculation system 800 described with reference to FIG. 10. The curvature calculation circuit 96a calculates the curvature of each of various portions of the insertion section 24, and outputs the information of the curvature of each of various portions of the insertion section 24.

The buckling detection system 110A includes a buckling judgment circuit 114A and a stiffness-to-be-enhanced portion determination circuit 116A, in addition to the storage device 112. The buckling judgment circuit 114A and stiffness-to-be-enhanced portion determination circuit 116A are included, for example, in the insertion control apparatus 30 together with the storage device 112. The buckling judgment circuit 114A and stiffness-to-be-enhanced portion determination circuit 116A are each composed of, for example, a combination of a processor and a storage device. Alternatively, the buckling judgment circuit 114A and stiffness-to-be-enhanced portion determination circuit 116A may each be composed of an exclusive circuit or a combination of general-purpose circuits.

The buckling judgment circuit 114A acquires the information of the curvature of each of various portions of the insertion section 24 from the curvature calculation circuit 96a, and compares the acquired curvature of each of various portions with a threshold Cth1 for buckling occurrence detection. As a result of the comparison, if the curvature of any one of the various portions of the insertion section 24 is greater than the threshold Cth1, the buckling judgment circuit 114A judges that a buckling occurs in the soft tube 24c. Conversely, if the curvature of each of the various portions of the insertion section 24 is not greater than the threshold Cth1, the buckling judgment circuit 114A judges that no buckling occurs in the soft tube 24c. The buckling judgment circuit 114A supplies the information of the judgment result to the stiffness-to-be-enhanced portion determination circuit 116A and the pulling operation detection system 140.

In FIG. 16, in a range R1a, the curvature is greater than the threshold Cth1, and a portion of the soft tube 24c that corresponds to the range R1a is the buckling portion 24ca. Note that although the curvature is also greater than the threshold Cth1 in a range R1b, the range R1b corresponds to the bendable section 24b and is thus excluded from the target of buckling occurrence detection. That the range R1b corresponds to the bendable section 24b is understood from the length from the distal end of the insertion section 24.

The stiffness-to-be-enhanced portion determination circuit 116A receives the information of the judgment result to the effect that the buckling occurs in the soft tube 24c, and determines the stiffness-to-be-enhanced portion 24cc. The stiffness-to-be-enhanced portion determination circuit 116A stores, in the storage device 112, information, e.g. position information, relating to the determined stiffness-to-be-enhanced portion 24cc.

(Example 1 of the Manner of Determining the Stiffness-to-be-Enhanced Portion 24cc)

Figure 17:
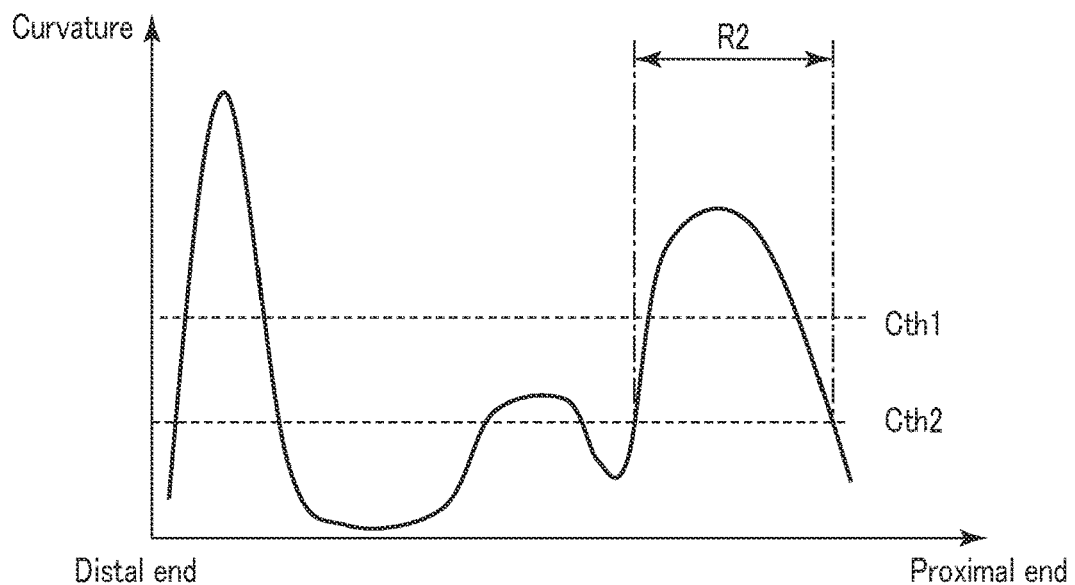
FIG. 17 is a graph showing curvatures of various portions of the insertion section in a state in which a buckling occurred, FIG. 17 being a graph for explaining an example of a manner of determining a stiffness-to-be-enhanced portion in the buckling detection system shown in FIG. 14.

Next, referring to FIG. 17 and FIG. 18, a description will be given of an example of the manner of determining the stiffness-to-be-enhanced portion 24cc. FIG. 17 is a graph showing curvatures of various portions of the insertion section 24 inserted in the large intestine 190 in a state in which a buckling occurs. The stiffness-to-be-enhanced portion determination circuit 116A acquires the information of the curvature of each of various portions of the insertion section 24 from the curvature calculation circuit 96a, and compares the acquired curvature of each of various portions with a threshold Cth2 for stiffness-to-be-enhanced portion determination. The threshold Cth2 for stiffness-to-be-enhanced portion determination is lower than the threshold Cth1 for buckling occurrence detection. As a result of the comparison, the stiffness-to-be-enhanced portion determination circuit 116A determines that the stiffness-to-be-enhanced portion 24cc is a portion of the insertion section 24 that corresponds to a range R2 in which the curvature exceeds the threshold Cth2.

Figure 18:
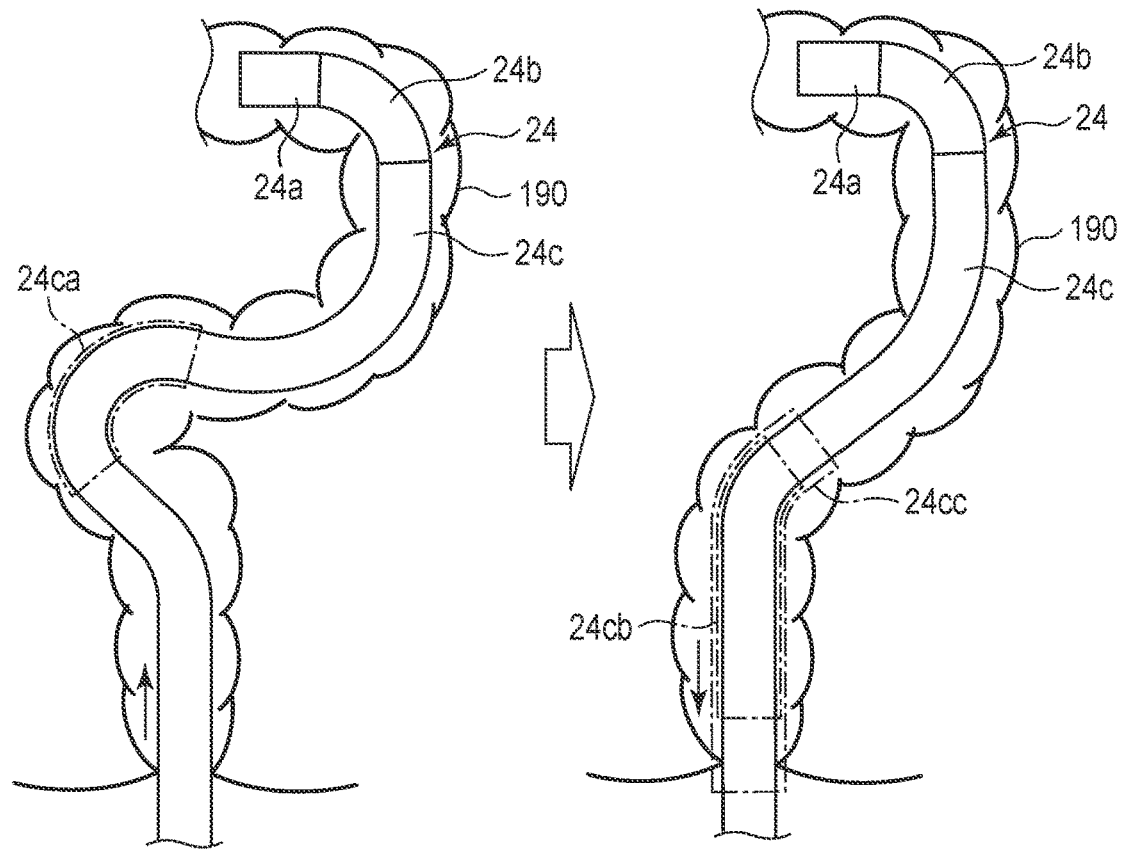
FIG. 18 is a view for explaining an example of the manner of determining a stiffness-to-be-enhanced portion in the buckling detection system shown in FIG. 14, FIG. 18 showing the insertion section in a state in which a buckling occurs, and the insertion section in which the buckling is eliminated by a pulling operation.

FIG. 18 shows the insertion section 24 in a state in which a buckling occurs, and the insertion section 24 in which the buckling is eliminated by a pulling operation. FIG. 18 also shows a buckling portion 24ca and a stiffness-to-be-enhanced portion 24cc. As shown in FIG. 18, the stiffness-to-be-enhanced portion 24cc includes the entirety of the buckling portion 24ca or the buckling correspondence portion 24cb.

Here, the stiffness-to-be-enhanced portion determination circuit 116A determines the stiffness-to-be-enhanced portion 24cc, based on the threshold Cth2 for stiffness-to-be-enhanced portion determination. However, it may be configured that the stiffness-to-be-enhanced portion determination circuit 116A first specifies the buckling portion 24ca, and then determines the stiffness-to-be-enhanced portion 24cc, based on the position information of the buckling portion 24ca. For example, the stiffness-to-be-enhanced portion determination circuit 116A may compare the curvature of each of various portions of the insertion section 24 with the threshold Cth1 for buckling occurrence detection, may specify the buckling portion 24ca as a portion of the insertion section 24 that has a curvature exceeding the threshold Cth1, and may determine the stiffness-to-be-enhanced portion 24cc, based on the position information of the buckling portion 24ca.

(Example 2 of the Manner of Determining the Stiffness-to-be-Enhanced Portion 24cc)

Figure 19:
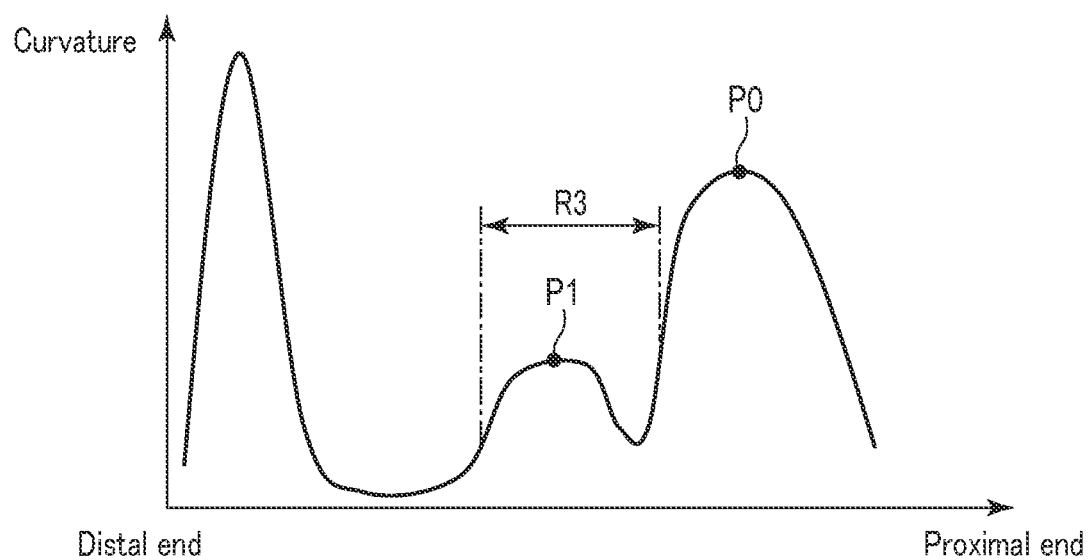
FIG. 19 is a graph showing curvatures of various portions of the insertion section in a state in which a buckling occurred, FIG. 19 being a graph for explaining another example of the manner of determining a stiffness-to-be-enhanced portion in the buckling detection system shown in FIG. 14.

Next, referring to FIG. 19 and FIG. 20, a description will be given of another example of the manner of determining the stiffness-to-be-enhanced portion 24cc. FIG. 19 is a graph showing curvatures of various portions of the insertion section 24 inserted in the large intestine 190 in a state in which a buckling occurred. The stiffness-to-be-enhanced portion determination circuit 116A acquires the information of the curvature of each of various portions of the insertion section 24 from the curvature calculation circuit 96a, and calculates a maximum point P0 of the curvature of the buckling portion 24ca and a maximum point P1 of the curvature of a distal-side bend portion 24ce, based on the acquired information of the curvature of each of various portions. Here, the distal-side bend portion 24ce is a bend portion that is located on the distal side of the buckling portion 24ca and is closest to the buckling portion 24ca. The stiffness-to-be-enhanced portion determination circuit 116A determines the stiffness-to-be-enhanced portion 24cc, based on the maximum point P1. For example, the stiffness-to-be-enhanced portion determination circuit 116A determines that the stiffness-to-be-enhanced portion 24cc is a portion of the insertion section 24 that includes the maximum point P1 and corresponds to a range R3 including at least a part of the buckling portion 24ca.

Figure 20:
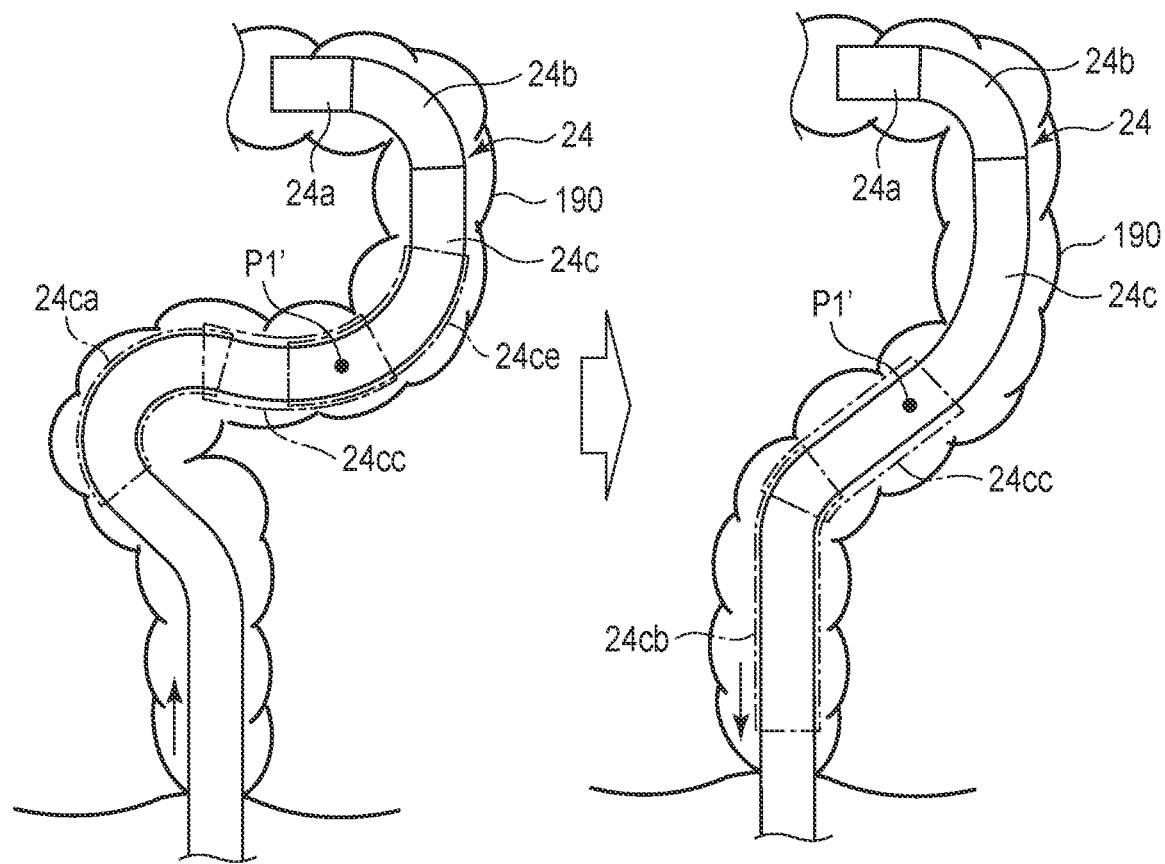
FIG. 20 is a view for explaining another example of the manner of determining a stiffness-to-be-enhanced portion in the buckling detection system shown in FIG. 14, FIG. 20 showing the insertion section in a state in which a buckling occurs, and the insertion section in which the buckling is eliminated by a pulling operation.

FIG. 20 shows the insertion section 24 in a state in which a buckling occurs, and the insertion section 24 in which the buckling is eliminated by a pulling operation. FIG. 20 also shows a buckling portion 24ca, a point P1' corresponding to the maximum point P1, and a stiffness-to-be-enhanced portion 24cc. As shown in FIG. 20, the stiffness-to-be-enhanced portion 24cc includes the point P1' corresponding to the maximum point P1, and a distal-side portion of the buckling portion 24ca or the buckling correspondence portion 24cb.

(Example 3 of the Manner of Determining the Stiffness-to-be-Enhanced Portion 24cc)

Next, referring to FIG. 21 and FIG. 22, a description will be given of still another example of the manner of determining the stiffness-to-be-enhanced portion 24cc. FIG. 21 is a graph showing curvatures of various portions of the insertion section 24 inserted in the large intestine 190 in a state in which a buckling occurred. The stiffness-to-be-enhanced portion determination circuit 116A acquires the information of the curvature of each of various portions of the insertion section 24 from the curvature calculation circuit 96a, and calculates a maximum point P0 of the curvature of the buckling portion 24ca and an inflection point P2 between the buckling portion 24ca and a distal-side bend portion 24ce, based on the acquired information of the curvature of each of various portions. Here, the distal-side bend portion 24ce is a bend portion that is located on the distal side of the buckling portion 24ca and is closest to the buckling portion 24ca. The stiffness-to-be-enhanced portion determination circuit 116A determines the stiffness-to-be-enhanced portion 24cc, based on the inflection point P2. For example, the stiffness-to-be-enhanced portion determination circuit 116A determines that the stiffness-to-be-enhanced portion 24cc is a portion of the insertion section 24 that includes the inflection point P2 and corresponds to a range R4 including at least a part of the buckling portion 24ca.

FIG. 22 shows the insertion section 24 in a state in which a buckling occurs, and the insertion section 24 in which the buckling is eliminated by a pulling operation. FIG. 22 also shows a buckling portion 24ca, a point P2' corresponding to the inflection point P2, and a stiffness-to-be-enhanced portion 24cc. As shown in FIG. 22, the stiffness-to-be-enhanced portion 24cc includes the point P2' corresponding to the inflection point P2, and a distal-side portion of the buckling portion 24ca or the buckling correspondence portion 24cb.

[Configuration Example 2 of the Buckling Detection System]

Figure 23:
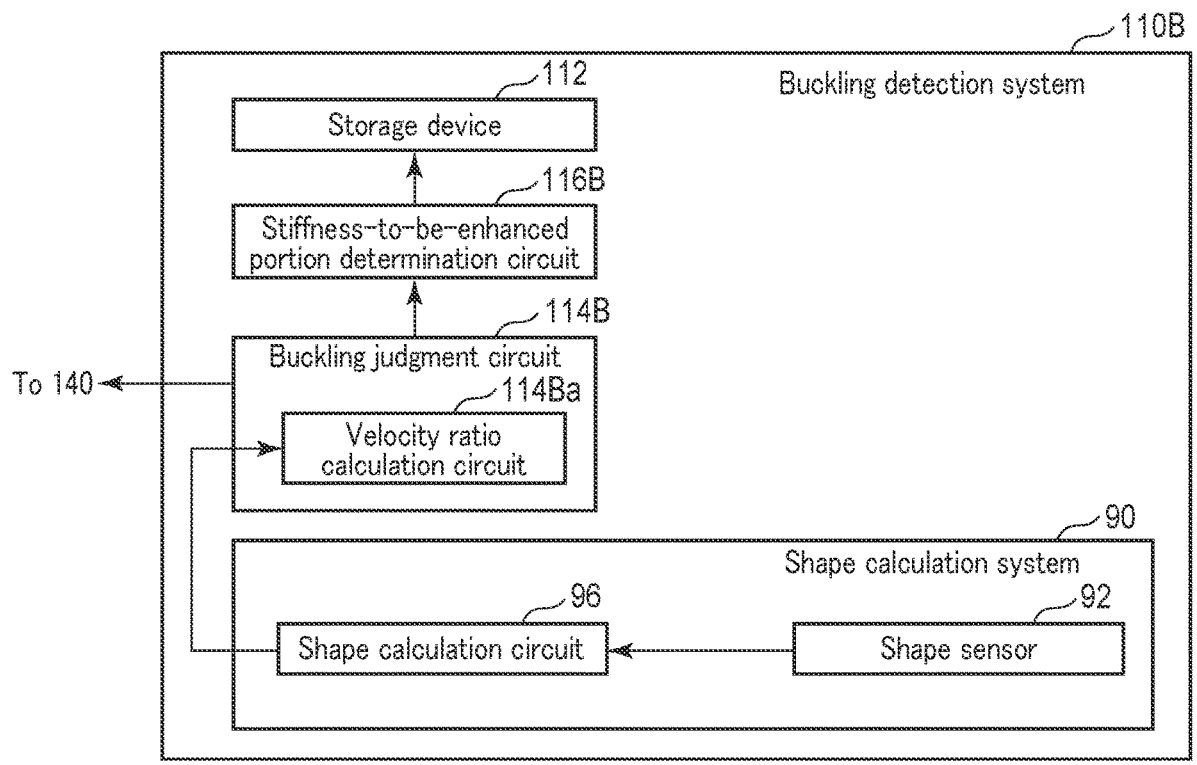
FIG. 23 schematically shows a buckling detection system according to another configuration example of the buckling detection system shown in FIG. 2.
Figure 24:
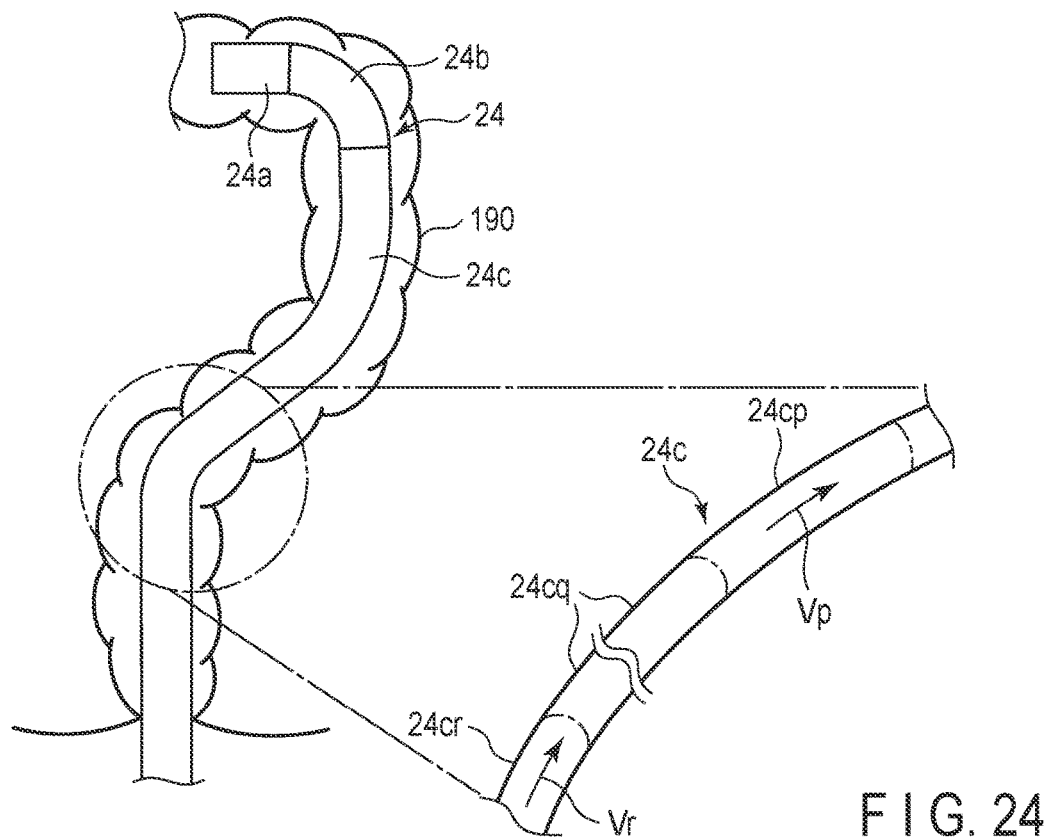
FIG. 24 is a view for describing the buckling detection system shown in FIG. 23, FIG. 24 showing an insertion section inserted in the large intestine, and segments that are set in a soft tube.

Another configuration example of the buckling detection system 110 will be described with reference to FIG. 23 and FIG. 24. FIG. 23 schematically shows a buckling detection system 110B according to the present configuration example. The buckling detection system 110B is configured to detect the occurrence of a buckling in the soft tube 24c, based on a velocity ratio of two mutually distanced portions of the soft tube 24c. FIG. 24 shows the insertion section inserted in the large intestine, and segments 24cn (n: a natural number) that are set in the soft tube 24c as various portions of the soft tube 24c.

The buckling detection system 110B includes the shape calculation system 90. The shape calculation system 90 may be, for example, the shape calculation system 700 described with reference to FIG. 8 or the shape calculation system 800 described with reference to FIG. 10. The shape calculation system 90 calculates a bend shape of the insertion section 24, and outputs the information of the bend shape of the insertion section 24. The information of the bend shape of the insertion section 24 includes three-dimensional position information of each of various portions of the soft tube 24c.

The buckling detection system 110B includes a buckling judgment circuit 114B and a stiffness-to-be-enhanced portion determination circuit 116B, in addition to the storage device 112. The buckling judgment circuit 114B and stiffness-to-be-enhanced portion determination circuit 116B are included, for example, in the insertion control apparatus 30 together with the storage device 112. The buckling judgment circuit 114B and stiffness-to-be-enhanced portion determination circuit 116B are each composed of, for example, a combination of a processor and a storage device. Alternatively, the buckling judgment circuit 114B and stiffness-to-be-enhanced portion determination circuit 116B may each be composed of an exclusive circuit or a combination of general-purpose circuits.

The buckling judgment circuit 114B includes a velocity ratio calculation circuit 114Ba configured to calculate a velocity ratio of two mutually distanced portions of the soft tube 24c. The velocity ratio calculation circuit 114Ba is composed of, for example, a combination of a processor and a storage device. The velocity ratio calculation circuit 114Ba successively acquires three-dimensional position information of each of various portions of the soft tube 24c from the shape calculation circuit 96. The velocity ratio calculation circuit 114Ba stores, in the internal storage device, the acquired three-dimensional position information of each of various portions of the soft tube 24c. In addition, the velocity ratio calculation circuit 114Ba calculates the velocity of each of various portions of the soft tube 24c, based on a variation with time of the acquired three-dimensional position information. The velocity has a magnitude and a direction. The direction is set as a positive direction in a case of advancing toward the distal side, and is set as a negative direction in a case of advancing toward the proximal side.

As shown in FIG. 24, a large number of segments 24cn (n: a natural number) neighboring each other along the center axis are set as the portions of the soft tube 24c. Further, segments 24cp, 24cq, and 24cr are set. Each of characters p, q, and r is a natural number, and a relationship of p<q<r is satisfied. At least one segment 24cq is interposed between the segment 24cp and segment 24cr. The segment 24cp is located on the distal side of the segment 24cr.

The velocity ratio calculation circuit 114Ba calculates velocities Vp and Vr of the segments 24cp and 24cr. Since various portions of the insertion section 24 move in an identical direction, the velocities Vp and Vr have an identical sign. In a pushing operation, the velocities Vp and Vr have a positive sign. The velocity ratio calculation circuit 114Ba further calculates a velocity ratio Vp/Vr of the segments 24cp and 24cr. Here, the velocity ratio is, exactly, a ratio of magnitudes of velocities, but, for the purpose of convenience, the velocity ratio is expressed as Vp/Vr. If a buckling occurs, the distal side does not advance and thus the velocity ratio Vp/Vr decreases.

The number of sets of segments 24cp and 24cr is not limited to one. Actually, the number of sets of segments 24cp and 24cr is plural. For example, the sets of segments 24cp and 24cr include a set including a most distally located segment of the portions of the soft tube 24c inserted in the large intestine 190, a set including a most proximally located segment of the portions of the soft tube 24c inserted in the large intestine 190, and a set including a segment therebetween. The description below will be given on the assumption that the number of sets of segments 24cp and 24cr is plural.

The buckling judgment circuit 114B compares the velocity ratios Vp/Vr of all sets of segments 24cp and 24cr with a threshold Vth1 for buckling occurrence detection. As a result of the comparison, if the velocity ratio Vp/Vr is lower than the threshold Vth1 in any one of the sets of segments 24cp and 24cr, the buckling judgment circuit 114B judges that a buckling occurs in the soft tube 24c. Conversely, if the velocity ratio Vp/Vr is not lower than the threshold Vth1 in each of the sets of segments 24cp and 24cr, the buckling judgment circuit 114B judges that no buckling occurs in the soft tube 24c. The buckling judgment circuit 114B supplies the information of the judgment result to the stiffness-to-be-enhanced portion determination circuit 116B and the pulling operation detection system 140.

The threshold is a numerical value that is 1 or less. As the threshold is closer to 1, the detection of buckling occurrence is more sensitive. In this case, very slight bend is judged to be a buckling. Conversely, as the threshold is farther from 1, the detection of buckling occurrence is less sensitive. In this case, a considerably large bend is not judged to be a buckling. In practice, a proper value is set for the threshold in consideration of actual conditions.

The stiffness-to-be-enhanced portion determination circuit 116B receives the information of the judgment result to the effect that the buckling occurs in the soft tube 24c, and calculates the stiffness-to-be-enhanced portion 24cc. The stiffness-to-be-enhanced portion determination circuit 116B stores, in the storage device 112, information, e.g. position information, relating to the determined stiffness-to-be-enhanced portion 24cc.

(Example of the Manner of Determining the Stiffness-to-be-Enhanced Portion 24cc)

Next, a description will be given of an example of the manner of determining the stiffness-to-be-enhanced portion 24cc. The stiffness-to-be-enhanced portion determination circuit 116A acquires the information of the velocity ratio Vp/Vr from the velocity ratio calculation circuit 114Ba, and compares the acquired velocity ratio Vp/Vr with a threshold Vth2 for stiffness-to-be-enhanced portion determination. The threshold Vth2 for stiffness-to-be-enhanced portion determination is greater than the threshold Vth1 for buckling occurrence detection. As a result of the comparison, the stiffness-to-be-enhanced portion determination circuit 116A determines that the stiffness-to-be-enhanced portion 24cc is a portion of the insertion section 24 that corresponds to a range in which the curvature is less than the threshold Vth2. Since the threshold Vth2 for stiffness-to-be-enhanced portion determination is greater than the threshold Vth1 for buckling occurrence detection, the stiffness-to-be-enhanced portion 24cc includes the entirety of the buckling portion 24ca.

[Configuration Example 3 of the Buckling Detection System]

Figure 25:
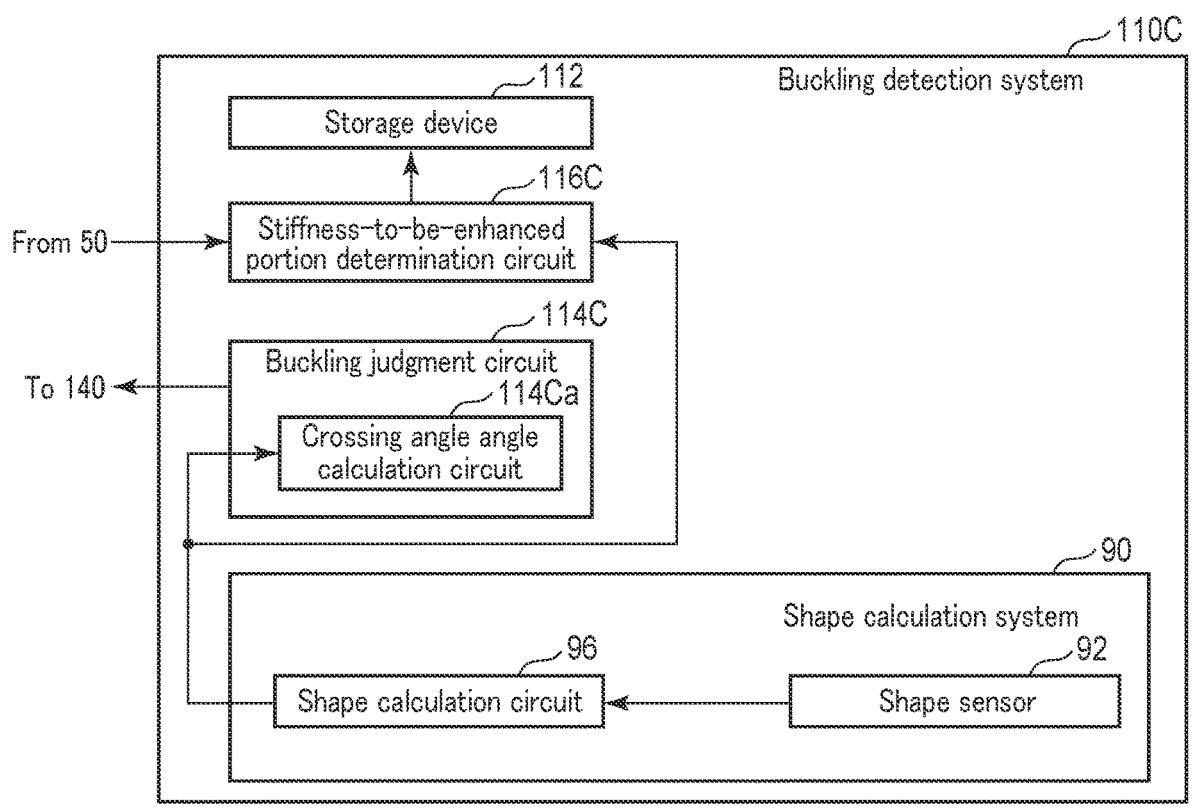
FIG. 25 schematically shows a buckling detection system according to another configuration example of the buckling detection system shown in FIG. 2.

A configuration example of the buckling detection system 110 will be described with reference to FIG. 25 to FIG. 27. FIG. 25 schematically shows a buckling detection system 110C according to the present configuration example. The buckling detection system 110C is configured to detect the occurrence of a buckling in the soft tube 24c, based on an angle of the soft tube 24c.

The buckling detection system 110C includes the shape calculation system 90. The shape calculation system 90 may be, for example, the shape calculation system 700 described with reference to FIG. 8 or the shape calculation system 800 described with reference to FIG. 10. The shape calculation system 90 calculates a bend shape of the insertion section 24, and outputs the information of the bend shape of the insertion section 24. The information of the bend shape of the insertion section 24 includes three-dimensional position information of each of various portions of the soft tube 24c.

The buckling detection system 110C includes a buckling judgment circuit 114C and a stiffness-to-be-enhanced portion determination circuit 116C, in addition to the storage device 112. The buckling judgment circuit 114C and stiffness-to-be-enhanced portion determination circuit 116C are included, for example, in the insertion control apparatus 30 together with the storage device 112. The buckling judgment circuit 114C and stiffness-to-be-enhanced portion determination circuit 116C are each composed of, for example, a combination of a processor and a storage device. Alternatively, the buckling judgment circuit 114C and stiffness-to-be-enhanced portion determination circuit 116C may each be composed of an exclusive circuit or a combination of general-purpose circuits.

The buckling judgment circuit 114C includes a crossing angle calculation circuit 114Ca. The crossing angle calculation circuit 114Ca is composed of, for example, a combination of a processor and a storage device. The crossing angle calculation circuit 114Ca successively acquires three-dimensional position information of each of various portions of the soft tube 24c from the shape calculation circuit 96. The crossing angle calculation circuit 114Ca stores, in the internal storage device, the acquired three-dimensional position information of each of various portions of the soft tube 24c. In addition, the crossing angle calculation circuit 114Ca calculates a crossing angle θ that is an index of buckling occurrence detection, based on the acquired three-dimensional position information.

Figure 26:
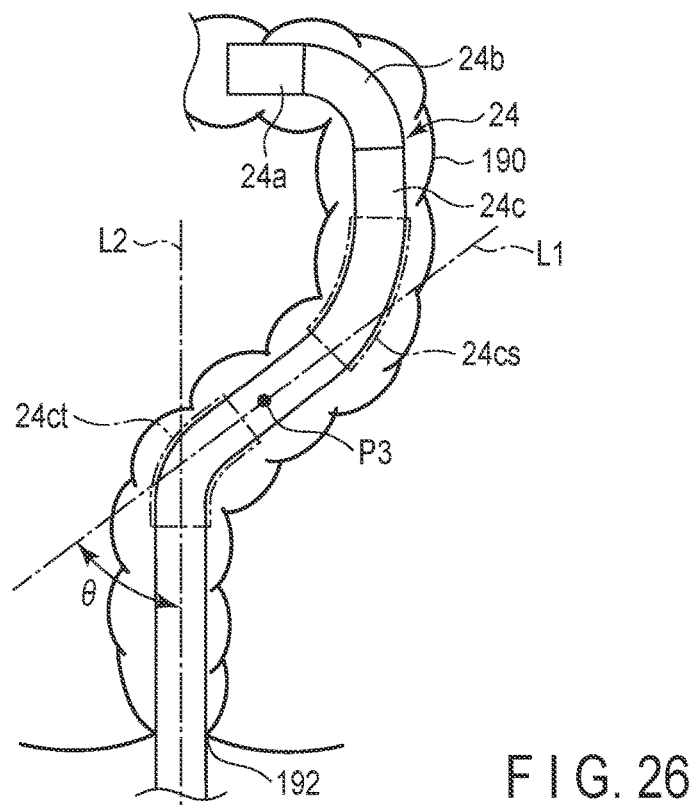
FIG. 26 is a view for describing the buckling detection system shown in FIG. 25, FIG. 26 showing an insertion section inserted in the large intestine, and a crossing angle that is an index of buckling occurrence detection.

FIG. 26 shows the insertion section 24 inserted in the large intestine 190. FIG. 26 also shows the crossing angle θ that is the index of buckling occurrence detection. Here, as shown in FIG. 26, the crossing angle θ is a crossing angle between a tangent line L1 at an inflection point P3 of two successive bend portions 24cs and 24ct formed in the soft tube 24c, and a straight line L2 passing through the axis of the soft tube 24c in the anus 192. The bend portion 24cs is located on the distal side of the bend portion 24ct. Here, although the straight line L2 is a straight line passing through the axis of the soft tube 24c in the anus 192, the straight line L2 may be changed to a straight line passing through the axis of the soft tube 24c in some other part.

When a variation with time of the crossing angle θ is positive, the buckling judgment circuit 114C judges that a buckling occurs in the soft tube 24c. Conversely, when the variation with time of the crossing angle θ is negative, the buckling judgment circuit 114C judges that no buckling occurs in the soft tube 24c. The buckling judgment circuit 114C supplies the information of the judgment result to the stiffness-to-be-enhanced portion determination circuit 116C and the pulling operation detection system 140.

Instead of judging the occurrence of a buckling, based on the variation with time of the crossing angle θ, the buckling judgment circuit 114C may judge the occurrence of a buckling, based on the magnitude of the crossing angle θ. In this case, the buckling judgment circuit 114C compares, for example, the crossing angle θ with a threshold θth1 for buckling occurrence detection. As a result of the comparison, if the crossing angle θ exceeds the threshold θth1, the buckling judgment circuit 114C judges that a buckling occurs in the soft tube 24c.

Instead of judging the occurrence of a buckling, based on the crossing angle θ, the buckling judgment circuit 114C may judge the occurrence of a buckling, based on a radius of curvature of the bend portion 24ct on the proximal side. In this case, the buckling judgment circuit 114C includes a radius-of-curvature calculation circuit configured to calculate the radius of curvature of the bend portion 24ct, in place of the crossing angle calculation circuit 114Ca. The radius-of-curvature calculation circuit is composed of, for example, a combination of a processor and a storage device.

When a variation with time of the radius of curvature of the bend portion 24ct is negative, the buckling judgment circuit 114C judges that a buckling occurs in the soft tube 24c. Conversely, when the variation with time of the radius of curvature of the bend portion 24ct is positive, the buckling judgment circuit 114C judges that no buckling occurs in the soft tube 24c.

The stiffness-to-be-enhanced portion determination circuit 116C receives the information of the judgment result to the effect that the buckling occurs in the soft tube 24c, and determines the stiffness-to-be-enhanced portion 24cc. The stiffness-to-be-enhanced portion determination circuit 116C stores, in the storage device 112, information, e.g. position information, relating to the determined stiffness-to-be-enhanced portion 24cc.

(Example of the Manner of Determining the Stiffness-to-be-Enhanced Portion 24cc)

Next, referring to FIG. 27, a description will be given of an example of the manner of determining the stiffness-to-be-enhanced portion 24cc. FIG. 27 shows the insertion section 24 in a state in which a buckling occurs, and the insertion section 24 in which the buckling is eliminated by a pulling operation. FIG. 27 also shows a buckling occurrence expectation area Rs where the occurrence of a buckling is expected.

The information of the buckling occurrence expectation area Rs where the occurrence of a buckling is expected is input from the input device 50 to the stiffness-to-be-enhanced portion determination circuit 116C. The stiffness-to-be-enhanced portion determination circuit 116C sets the buckling occurrence expectation area Rs where the occurrence of a buckling is expected. For example, as shown in FIG. 27, the stiffness-to-be-enhanced portion determination circuit 116C sets the buckling occurrence expectation area Rs in a coordinate space that expresses the bend shape of the insertion section 24. Although FIG. 27 shows a state in which one buckling occurrence expectation area Rs is set, the stiffness-to-be-enhanced portion determination circuit 116C may set buckling occurrence expectation areas Rs.

Figure 27:
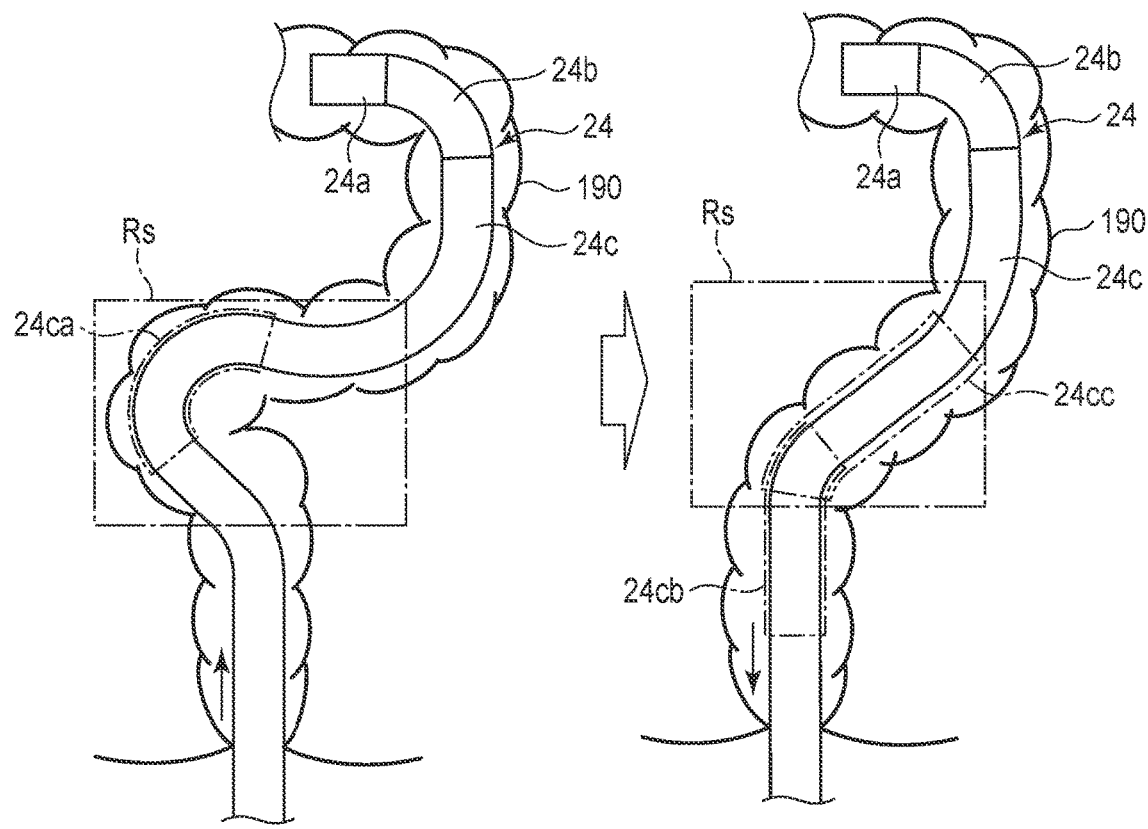
FIG. 27 is a view for explaining an example of the manner of determining a stiffness-to-be-enhanced portion in the buckling detection system shown in FIG. 25, FIG. 27 showing an insertion section in a state in which a buckling occurs, the insertion section in which the buckling is eliminated by a pulling operation, and a buckling occurrence expectation area.

As shown in a right part of FIG. 27, the stiffness-to-be-enhanced portion determination circuit 116C determines that the stiffness-to-be-enhanced portion 24cc is a portion of the soft tube 24c that is located in the buckling occurrence expectation area Rs in the insertion section 24 in which the buckling is eliminated. The stiffness-to-be-enhanced portion 24cc includes a portion of the soft tube 24c that is located on the distal side of the buckling correspondence portion 24cb, and a portion of the soft tube 24c that corresponds to a distal-side portion of the buckling correspondence portion 24cb. [Configuration Example 4 of the Buckling Detection System]

Figure 28:
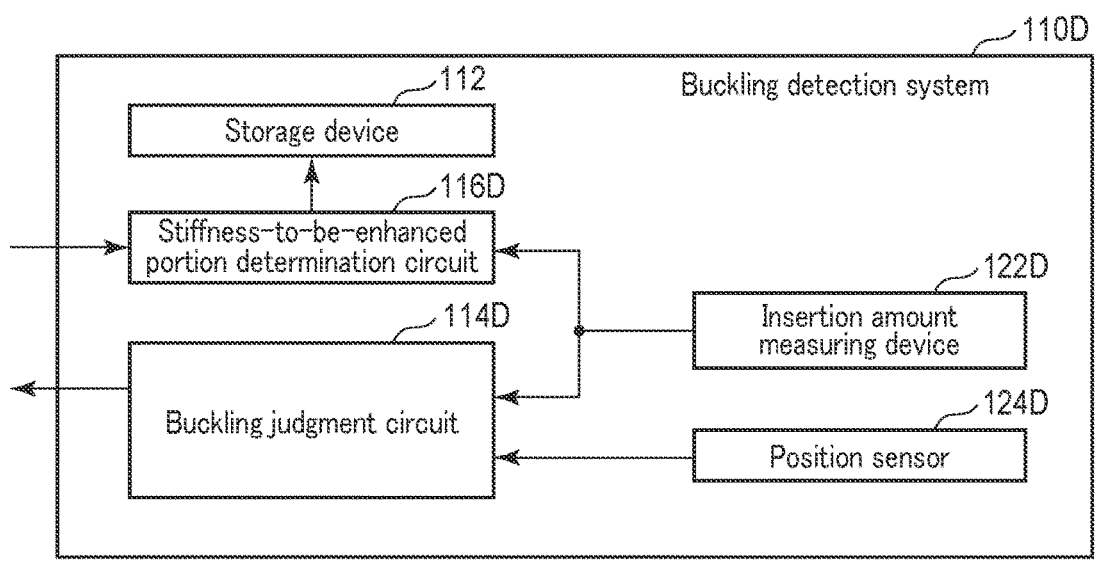
FIG. 28 schematically shows a buckling detection system according to another configuration example of the buckling detection system shown in FIG. 2.
Figure 29:
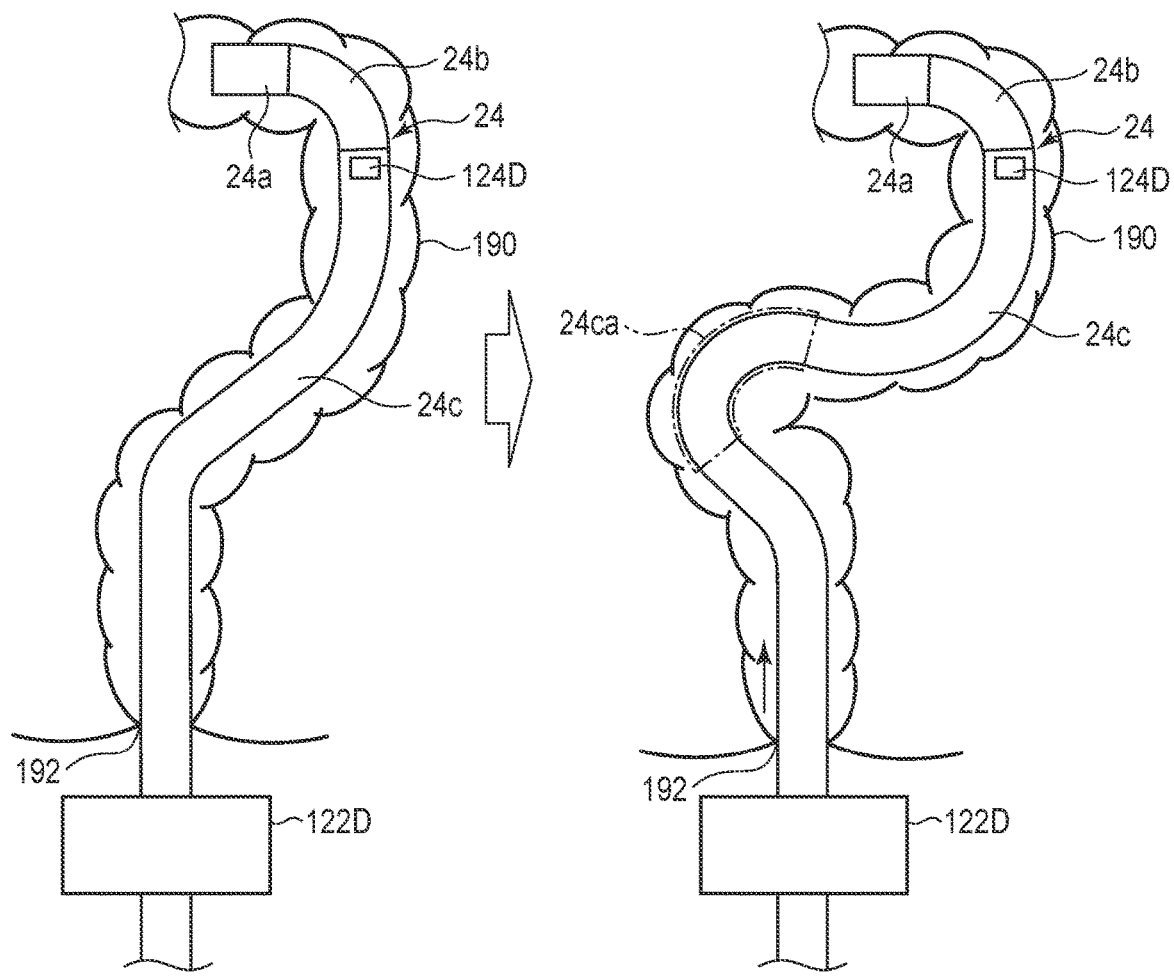
FIG. 29 is a view for describing the buckling detection system shown in FIG. 28, FIG. 29 showing a state in which a buckling occurs by a pushing operation of the insertion section.

A configuration example of the buckling detection system 110 will be described with reference to FIG. 28 and FIG. 29. FIG. 28 schematically shows a buckling detection system 110D according to the present configuration example. The buckling detection system 110D is configured to detect the occurrence of a buckling in the soft tube 24c, based on an insertion amount of the insertion section 24. FIG. 29 shows a state in which a buckling occurs by a pushing operation of the insertion section 24. A left part of FIG. 29 shows a state before the occurrence of a buckling, and a right part of FIG. 29 shows a state in which a buckling occurs by a pushing operation.

The buckling detection system 110D includes a buckling judgment circuit 114D, a stiffness-to-be-enhanced portion determination circuit 116D, an insertion amount measuring device 122D, and a position sensor 124D, in addition to the storage device 112. The buckling judgment circuit 114D and stiffness-to-be-enhanced portion determination circuit 116D are included, for example, in the insertion control apparatus 30. The buckling judgment circuit 114D and stiffness-to-be-enhanced portion determination circuit 116D are each composed of, for example, a combination of a processor and a storage device.

The insertion amount measuring device 122D is disposed near the anus 192. The insertion amount measuring device 122D measures an insertion amount of the insertion section 24. In other words, the insertion amount measuring device 122D measures a length of the insertion section 24 that has passed through the insertion amount measuring device 122D. The insertion amount measuring device 122D outputs insertion amount information of the measurement result to the buckling judgment circuit 114D.

The position sensor 124D is disposed in the insertion section 24, and outputs three-dimensional position information of the location of disposition to the buckling judgment circuit 114D. For example, the position sensor 124D is disposed in a distal portion of the soft tube 24c. The position of disposition of the position sensor 124D is not limited to this. The position sensor 124D may be disposed, for example, in a proximal portion of the bendable section 24b. Alternatively, when a portion in which a buckling will occur is predicted, it suffices that the position sensor 124D is disposed in a portion on the distal side of the portion where the occurrence of the buckling is expected.

The buckling judgment circuit 114D successively acquires the insertion amount information by the insertion amount measuring device 122D and the position information supplied from the position sensor 124D, and stores, in the internal storage device, the acquired insertion amount information and position information. Based on the insertion amount information and position information, the buckling judgment circuit 114D determines whether a buckling occurs in the soft tube 24c. For example, the buckling judgment circuit 114D calculates a variation amount of the insertion amount and a variation amount of the position, and further calculates the ratio of the variation amount of the position to the variation amount of the insertion amount. Hereinafter, for the purpose of convenience, the ratio of the variation amount of the position to the variation amount of the insertion amount is referred to as "position variation/insertion amount variation".

The buckling judgment circuit 114D compares the calculated position variation/insertion amount variation with a threshold for buckling occurrence detection. As a result of the comparison, if the position variation/insertion amount variation is less than the threshold, the buckling judgment circuit 114D judges that a buckling occurs in the soft tube 24c. Conversely, if the position variation/insertion amount variation is not less than the threshold, the buckling judgment circuit 114D judges that no buckling occurs in the soft tube 24c. The buckling judgment circuit 114D supplies the information of the judgment result to the stiffness-to-be-enhanced portion determination circuit 116D and the pulling operation detection system 140.

The threshold is a numerical value that is 1 or less. As the threshold is closer to 1, the detection of buckling occurrence is more sensitive. In this case, a very slight bend is judged to be a buckling. Conversely, as the threshold is farther from 1, the detection of buckling occurrence is less sensitive. In this case, a considerably large bend is not judged to be a buckling. In practice, a proper value is set for the threshold in consideration of actual conditions.

The stiffness-to-be-enhanced portion determination circuit 116D receives the information of the judgment result to the effect that the buckling occurs in the soft tube 24c, and determines the stiffness-to-be-enhanced portion 24cc. The stiffness-to-be-enhanced portion determination circuit 116D stores, in the storage device 112, information, e.g. position information, relating to the determined stiffness-to-be-enhanced portion 24cc.

(Example of the Manner of Determining the Stiffness-to-be-Enhanced Portion 24cc)

Next, a description will be given of an example of the manner of determining the stiffness-to-be-enhanced portion 24cc. Information of a portion of the soft tube 24c where the occurrence of a buckling is expected is input from the input device 50 to the stiffness-to-be-enhanced portion determination circuit 116D. Hereinafter, for the purpose of convenience, the information of the portion of the soft tube 24c where the occurrence of a buckling is expected is referred to as "buckling occurrence expectation information". The buckling occurrence expectation information is information of the length of a predetermined range that is set with reference to the anus 192.

The stiffness-to-be-enhanced portion determination circuit 116D determines the stiffness-to-be-enhanced portion 24cc, based on the buckling occurrence expectation information input from the input device 50 and the insertion amount information by the insertion amount measuring device 122D. The stiffness-to-be-enhanced portion 24cc includes at least a portion of the soft tube 24c that neighbors the portion of the soft tube 24c corresponding to the buckling occurrence expectation information, i.e., a buckling occurrence expectation portion, and that is located on the distal side of the buckling occurrence expectation portion.

[Configuration Example 1 of the Pulling Operation Detection System]

Figure 30:
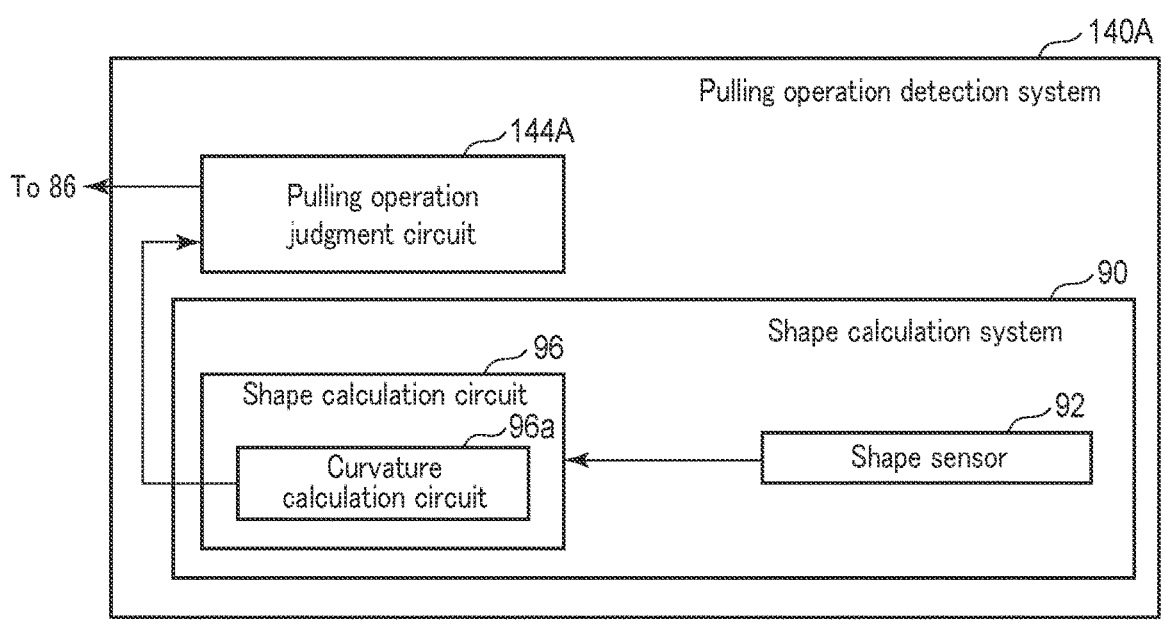
FIG. 30 schematically shows a pulling operation detection system according to a configuration example of a pulling operation detection system shown in FIG. 2.

A configuration example of the pulling operation detection system 140 will be described with reference to FIG. 30 to FIG. 32. FIG. 30 schematically shows a pulling operation detection system 140A according to the present configuration example. The pulling operation detection system 140A is configured to detect that a sufficient pulling operation of the insertion section 24 is performed, based on the curvature of each of various portions of the soft tube 24c. FIG. 31 shows a state in which a buckling is eliminated by a pulling operation of the insertion section 24. A left part of FIG. 31 shows a state in which a buckling occurs, and a right part of FIG. 31 shows a state in which the buckling is eliminated by a pulling operation.

The pulling operation detection system 140A includes the shape calculation system 90. The shape calculation system 90 includes a curvature calculation circuit 96a configured to calculate the curvature of each of various portions of the insertion section 24. The curvature calculation circuit 96a corresponds to the curvature calculation circuit 752 of the shape calculation system 700 described with reference to FIG. 8, or the curvature calculation circuit 876 of the shape calculation system 800 described with reference to FIG. 10. The curvature calculation circuit 96a calculates the curvature of each of various portions of the insertion section 24, and outputs the information of the curvature of each of various portions of the insertion section 24.

The pulling operation detection system 140A includes a pulling operation judgment circuit 144A. The pulling operation judgment circuit 144A is included, for example, in the insertion control apparatus 30. The pulling operation judgment circuit 144A is composed of, for example, a combination of a processor and a storage device. Alternatively, the pulling operation judgment circuit 144A may be composed of an exclusive circuit or a combination of general-purpose circuits.

The pulling operation judgment circuit 144A acquires the information of the curvature of each of various portions of the insertion section 24 from the curvature calculation circuit 96a, and compares the acquired curvature of each of various portions with a threshold Cth3 for buckling elimination detection. The threshold Cth3 for buckling elimination detection is less than the threshold Cth1 for buckling occurrence detection. For example, the threshold Cth3 for buckling elimination detection is less than the threshold Cth2 for stiffness-to-be-enhanced portion determination. As a result of the comparison, if the curvature of each of various portions of the insertion section 24 is less than the threshold Cth3, the pulling operation judgment circuit 144A judges that the buckling is eliminated and judges that a sufficient pulling operation is performed. The pulling operation judgment circuit 144A supplies the information of the judgment result to the stiffness control circuit 86. The stiffness control circuit 86 receives the information of the judgment result from the pulling operation judgment circuit 144A, and starts the control of the stiffness changing devices 82.

FIG. 32 shows a variation of a graph indicative of curvatures of various portions of the insertion section 24 inserted in the large intestine 190, the insertion section 24 transitioning from a state (solid line) in which a buckling occurs to a state (two-dot-and-dash line) in which the buckling is eliminated. In FIG. 32, in a range R1a, in the state in which a buckling occurs, the curvature exceeds the threshold Cth1, but, in the state in which the buckling is eliminated, the curvature Cth3 is lower than the threshold Cth3. Note that, in a range R1b, even in the state in which the buckling is eliminated, the curvature exceeds the threshold Cth1, but the range R1b corresponds to the bendable section 24b and is thus excluded from the target of the detection of the pulling operation. That the range R1b corresponds to the bendable section 24b is understood from the length from the distal end of the insertion section 24.

[Configuration Example 2 of the Pulling Operation Detection System]

Figure 33:
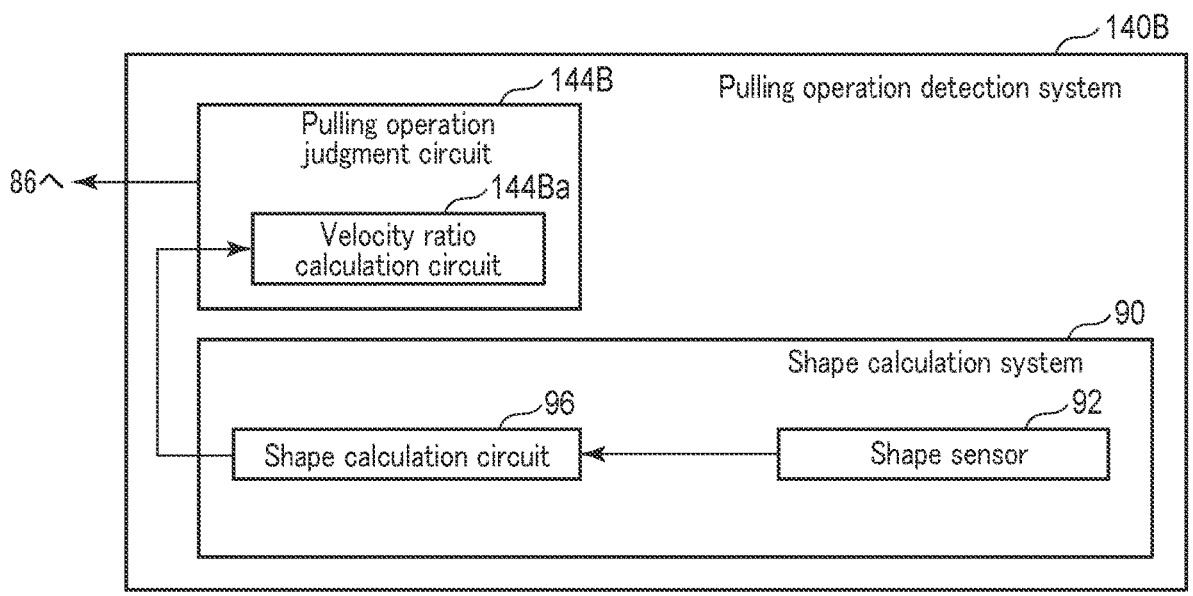
FIG. 33 schematically shows a pulling operation detection system according to another configuration example of the pulling operation detection system shown in FIG. 2.
Figure 34:
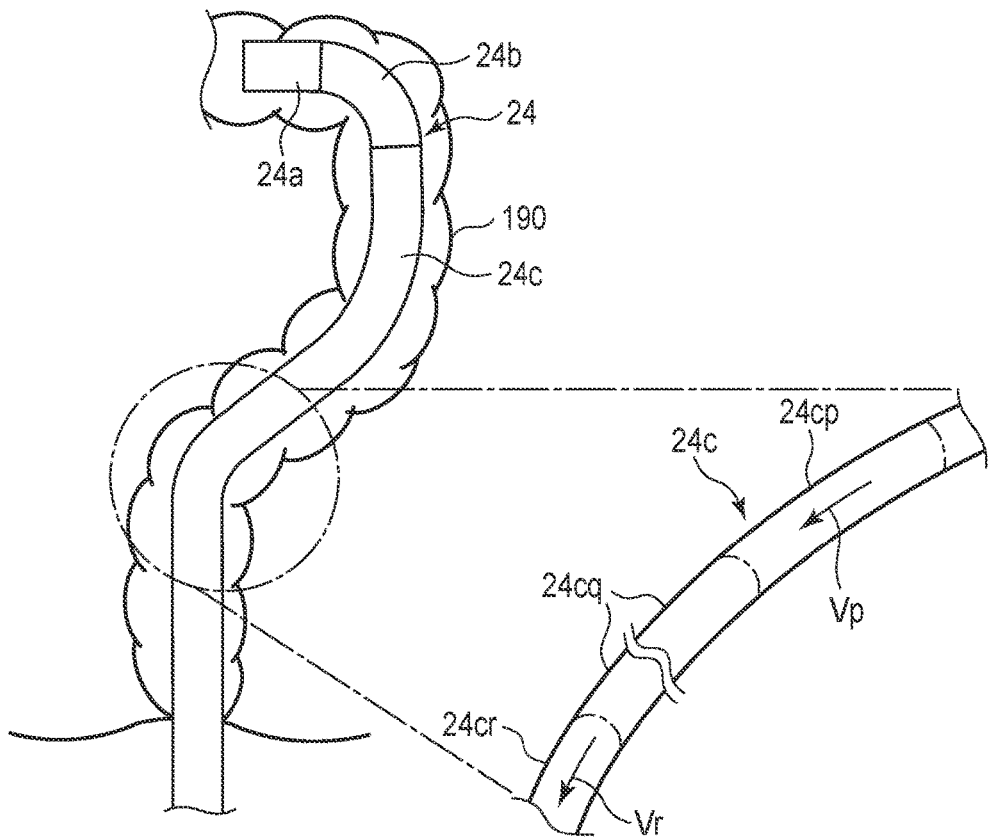
FIG. 34 is a view for describing the pulling operation detection system shown in FIG. 33, FIG. 34 showing an insertion section inserted in the large intestine, and segments that are set in a soft tube.

A configuration example of the pulling operation detection system 140 will be described with reference to FIG. 33 to FIG. 34. FIG. 30 schematically shows a pulling operation detection system 140B according to the present configuration example. The pulling operation detection system 140B is configured to detect that a sufficient pulling operation of the insertion section 24 is performed, based on a velocity ratio of two mutually distanced portions of the soft tube 24c. FIG. 34 shows the insertion section inserted in the large intestine, and segments 24cn (n: a natural number) that are set in the soft tube 24c as various portions of the soft tube 24c.

The pulling operation detection system 140B includes the shape calculation system 90. The shape calculation system 90 may be, for example, the shape calculation system 700 described with reference to FIG. 8 or the shape calculation system 800 described with reference to FIG. 10. The shape calculation system 90 calculates a bend shape of the insertion section 24, and outputs the information of the bend shape of the insertion section 24. The information of the bend shape of the insertion section 24 includes three-dimensional position information of each of various portions of the soft tube 24c.

The pulling operation detection system 140B includes a pulling operation judgment circuit 144B. The pulling operation judgment circuit 144B is included, for example, in the insertion control apparatus 30. The pulling operation judgment circuit 144B is composed of, for example, a combination of a processor and a storage device. Alternatively, the pulling operation judgment circuit 144B may be composed of an exclusive circuit or a combination of general-purpose circuits.

The pulling operation judgment circuit 144B includes a velocity ratio calculation circuit 144Ba configured to calculate a velocity ratio of two mutually distanced portions of the soft tube 24c. The velocity ratio calculation circuit 144Ba is composed of, for example, a combination of a processor and a storage device. The velocity ratio calculation circuit 144Ba successively acquires three-dimensional position information of each of various portions of the soft tube 24c from the shape calculation circuit 96. The velocity ratio calculation circuit 144Ba stores, in the internal storage device, the acquired three-dimensional position information of each of various portions of the soft tube 24c. In addition, the velocity ratio calculation circuit 144Ba calculates the velocity of each of various portions of the soft tube 24c, based on a variation with time of the acquired three-dimensional position information. The velocity has a magnitude and a direction. The direction is set as a positive direction in a case of advancing toward the distal side, and is set as a negative direction in a case of advancing toward the proximal side.

As shown in FIG. 34, a large number of segments 24cn (n: a natural number) neighboring each other along the center axis are set as the portions of the soft tube 24c. Further, segments 24cp, 24cq, and 24cr are set. Each of characters p, q, and r is a natural number, and a relationship of p<q<r is satisfied. At least one segment 24cq is interposed between the segment 24cp and segment 24cr. The segment 24cp is located on the distal side of the segment 24cr.

The velocity ratio calculation circuit 144Ba calculates velocities Vp and Vr of the segments 24cp and 24cr. Since various portions of the insertion section 24 move in an identical direction, the velocities Vp and Vr have an identical sign. In a pulling operation, the velocities Vp and Vr have a negative sign. The velocity ratio calculation circuit 144Ba further calculates a velocity ratio Vp/Vr of the segments 24cp and 24cr. Here, the velocity ratio is, exactly, a ratio of magnitudes of velocities, but, for the purpose of convenience, the velocity ratio is expressed as Vp/Vr.

The number of sets of segments 24cp and 24cr is not limited to one. Actually, the number of sets of segments 24cp and 24cr is plural. For example, the sets of segments 24cp and 24cr include a set including a most distally located segment of the portions of the soft tube 24c inserted in the large intestine 190, a set including a most proximally located segment of the portions of the soft tube 24c inserted in the large intestine 190, and a set including a segment therebetween. The description below will be given on the assumption that the number of sets of segments 24cp and 24cr is plural.

The pulling operation judgment circuit 144B compares the velocity ratios Vp/Vr of all sets of segments 24cp and 24cr with a threshold Vth3 for buckling elimination detection. The threshold Vth3 for buckling elimination detection is greater than the threshold Vth1 for buckling occurrence detection. For example, the threshold Vth3 for buckling elimination detection is greater than the threshold Vth2 for stiffness-to-be-enhanced portion determination. As a result of the comparison, if the sign of Vp or Vr is negative and the velocity ratio Vp/Vr exceeds the threshold Vth3 in all sets of segments 24cp and 24cr, the pulling operation judgment circuit 144B judges that the buckling of the soft tube 24c is eliminated and judges that a sufficient pulling operation is performed. The pulling operation judgment circuit 144B supplies the information of the judgment result to the stiffness control circuit 86. The stiffness control circuit 86 receives the information of the judgment result from the pulling operation judgment circuit 144B, and starts the control of the stiffness changing devices 82.

The threshold is a numerical value that is 1 or less. As the threshold is closer to 1, the detection of buckling occurrence is more sensitive. In this case, a very slight bend is judged to be a buckling. Conversely, as the threshold is farther from 1, the detection of buckling occurrence is less sensitive. In this case, a considerably large bend is not judged to be a buckling. In practice, a proper value is set for the threshold in consideration of actual conditions.

[Configuration Example 3 of the Pulling Operation Detection System]

Figure 35:
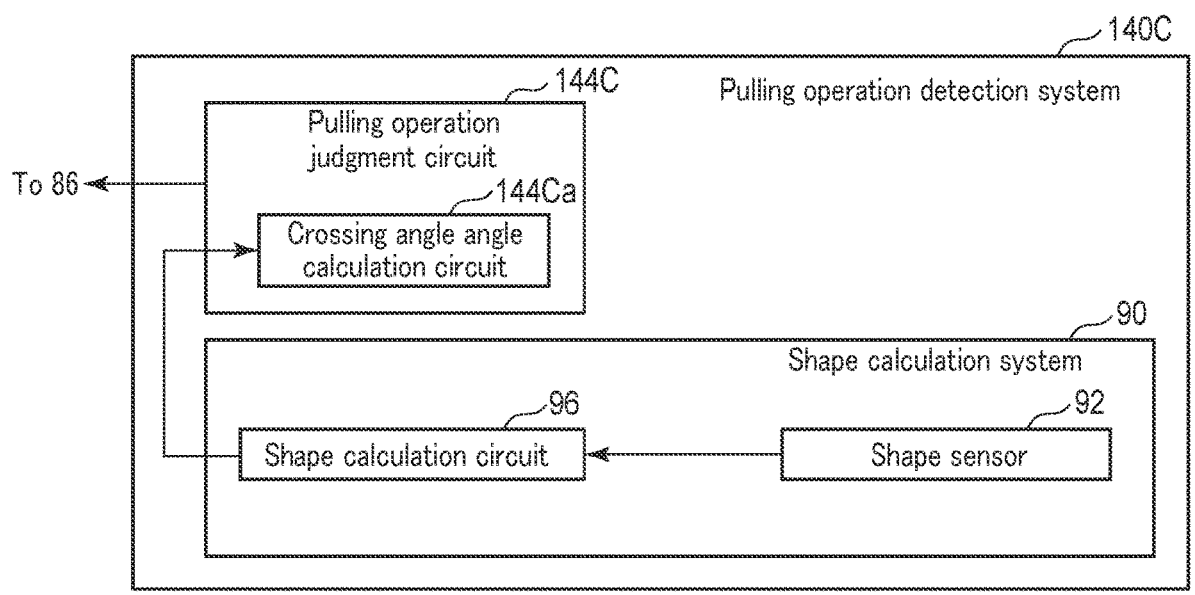
FIG. 35 schematically shows a pulling operation detection system according to another configuration example of the pulling operation detection system shown in FIG. 2.

A configuration example of the pulling operation detection system 140 will be described with reference to FIG. 35. FIG. 35 schematically shows a pulling operation detection system 140C according to the present configuration example. The pulling operation detection system 140C is configured to detect that a sufficient pulling operation of the insertion section 24 is performed, based on an angle of the soft tube 24c.

The pulling operation detection system 140C includes the shape calculation system 90. The shape calculation system 90 may be, for example, the shape calculation system 700 described with reference to FIG. 8 or the shape calculation system 800 described with reference to FIG. 10. The shape calculation system 90 calculates a bend shape of the insertion section 24, and outputs the information of the bend shape of the insertion section 24. The information of the bend shape of the insertion section 24 includes three-dimensional position information of each of various portions of the soft tube 24c.

The pulling operation detection system 140C includes a pulling operation judgment circuit 144C. The pulling operation judgment circuit 144C is included, for example, in the insertion control apparatus 30. The pulling operation judgment circuit 144C is composed of, for example, a combination of a processor and a storage device. Alternatively, the pulling operation judgment circuit 144C may be composed of an exclusive circuit or a combination of general-purpose circuits.

The pulling operation judgment circuit 144C includes a crossing angle calculation circuit 144Ca. The crossing angle calculation circuit 144Ca is composed of, for example, a combination of a processor and a storage device. The crossing angle calculation circuit 144Ca successively acquires three-dimensional position information of each of various portions of the soft tube 24c from the shape calculation circuit 96. The crossing angle calculation circuit 144Ca stores, in the internal storage device, the acquired three-dimensional position information of each of various portions of the soft tube 24c. In addition, the crossing angle calculation circuit 144Ca calculates a crossing angle θ that is an index of buckling elimination detection, based on the acquired three-dimensional position information. The crossing angle θ is as described with reference to FIG. 26.

The pulling operation judgment circuit 144C compares the crossing angle θ with a threshold θth2 for buckling elimination detection. The threshold θth2 for buckling elimination detection is lower than the threshold θth1 for buckling occurrence detection. As a result, if the crossing angle θ is less than the threshold θth2, the pulling operation judgment circuit 144C judges that the buckling is eliminated and judges that a sufficient pulling operation is performed. The pulling operation judgment circuit 144C supplies the information of the judgment result to the stiffness control circuit 86. The stiffness control circuit 86 receives the information of the judgment result from the pulling operation judgment circuit 144C, and starts the control of the stiffness changing devices 82.

[Configuration Example 4 of the Pulling Operation Detection System]

Figure 36:
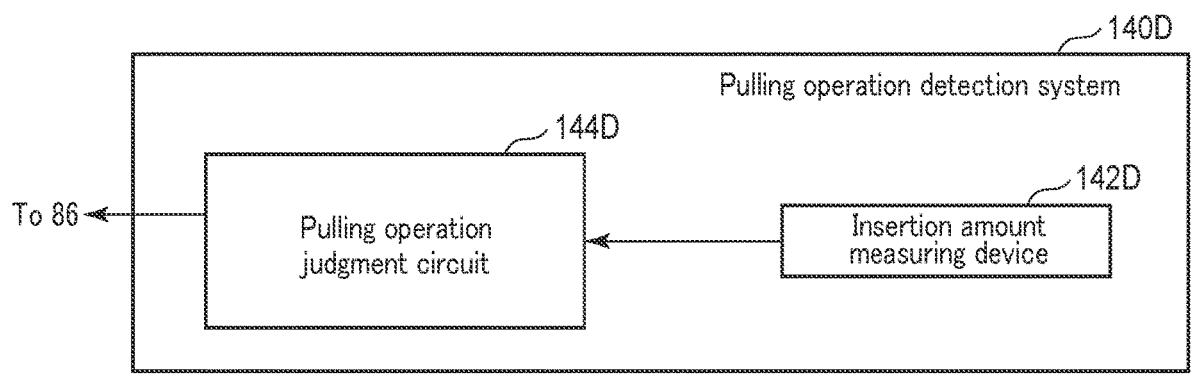
FIG. 36 schematically shows a pulling operation detection system according to another configuration example of the pulling operation detection system shown in FIG. 2.
Figure 37:
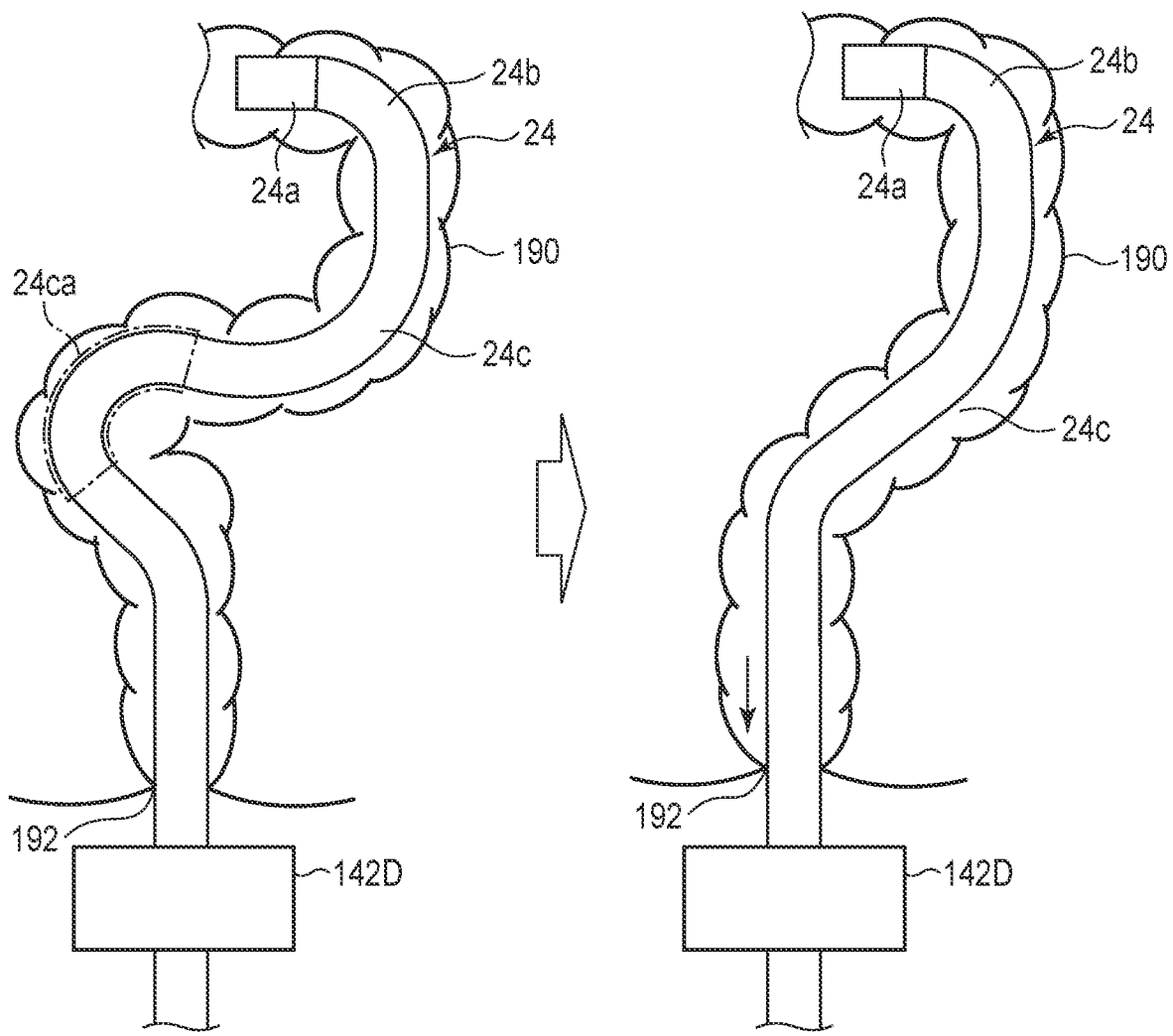
FIG. 37 is a view for describing the pulling operation detection system shown in FIG. 36, FIG. 37 showing a state in which a buckling is eliminated by a pulling operation of the insertion section.
Figure 38:
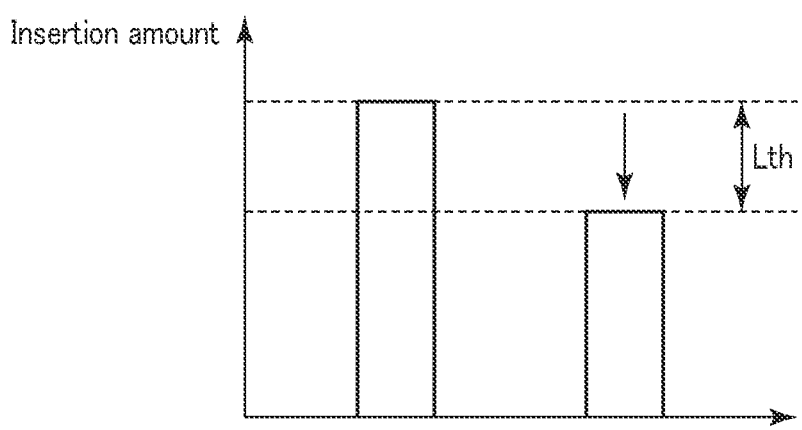
FIG. 38 shows a state of determination based on an insertion amount of the insertion section in the pulling operation detection system shown in FIG. 36.

A configuration example of the pulling operation detection system 140 will be described with reference to FIG. 36 to FIG. 38. FIG. 36 schematically shows a pulling operation detection system 140D according to the present configuration example. The pulling operation detection system 140D is configured to detect that a sufficient pulling operation is performed, based on an insertion amount of the insertion section 24. FIG. 37 shows a state in which a buckling is eliminated by a pulling operation of the insertion section 24. A left part of FIG. 37 shows a state in which a buckling occurs, and a right part of FIG. 37 shows a state in which the buckling is eliminated by a pulling operation.

The pulling operation detection system 140D includes a pulling operation judgment circuit 144D and an insertion amount measuring device 142D. The pulling operation judgment circuit 144D is included, for example, in the insertion control apparatus 30. The pulling operation judgment circuit 144D is composed of, for example, a combination of a processor and a storage device.

The insertion amount measuring device 142D is disposed near the anus 192. The insertion amount measuring device 142D measures an insertion amount of the insertion section 24. In other words, the insertion amount measuring device 142D measures a length of the insertion section 24 that has passed through the insertion amount measuring device 142D. The insertion amount measuring device 142D outputs insertion amount information of the measurement result to the pulling operation judgment circuit 144D.

The pulling operation judgment circuit 144D successively acquires the insertion amount information by the insertion amount measuring device 142D and stores, in the internal storage device, the acquired insertion amount information. Based on the insertion amount information, the pulling operation judgment circuit 144D determines whether a sufficient pulling operation is performed. FIG. 38 shows a state of determination based on the insertion amount of the insertion section 24. In FIG. 38, a left part shows the insertion amount of the insertion section 24 before a pulling operation, and a right part shows the insertion amount after the pulling operation. The pulling operation judgment circuit 144D determines that a sufficient pulling operation is performed, when the insertion amount of the insertion section 24 decreases by an amount greater than a threshold Lth. The pulling operation judgment circuit 144D supplies the information of the judgment result to the stiffness control circuit 86. The stiffness control circuit 86 receives the information of the judgment result from the pulling operation judgment circuit 144D, and starts the control of the stiffness changing devices 82.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A flexible tube insertion apparatus comprising:
a processor comprising hardware, the processor being configured to:
control a stiffness of each of various portions of a flexible tube configured to be inserted into a tract of a target;
detect occurrence of a buckling in the flexible tube;
detect that a pulling operation of the flexible tube is performed, after detecting the occurrence of the buckling;
store position information of a stiffness-to-be-enhanced portion including a portion of the flexible tube adjacent to a buckling portion of the flexible tube and located on a distal side of the buckling portion, and
increase a stiffness of the stiffness-to-be-enhanced portion, based on the position information stored in the storage device, when the pulling operation is detected.

2. The flexible tube insertion apparatus of claim 1, wherein the processor is configured to:
detect completion of the pulling operation, and
increase the stiffness of the stiffness-to-be-enhanced portion when the completion of the pulling operation is detected.

3. The flexible tube insertion apparatus of claim 1, wherein the processor is configured not to increase the stiffness of the flexible tube during a period from when the occurrence of the buckling is detected to when the pulling operation is detected.

4. The flexible tube insertion apparatus of claim 1, further comprising stiffness changing devices, and the processor is configured to independently control the stiffness changing devices, the stiffness changing devices being provided on the flexible tube and arranged along a longitudinal axis of the flexible tube, and each stiffness changing device being configured to change a stiffness of a portion of the flexible tube in which the stiffness changing device is provided.

5. The flexible tube insertion apparatus of claim 1, wherein the processor is further configured to calculate a shape of the flexible tube,
wherein the stiffness-to-be-enhanced portion is determined, based on information of the calculated shape of the flexible tube.

6. The flexible tube insertion apparatus of claim 5, further comprising a shape sensor configured to acquire shape information of each of various portions of the flexible tube, and the processor is configured to calculate a shape of an entirety of the flexible tube, based on the shape information of each of various portions of the flexible tube acquired by the shape sensor.

7. The flexible tube insertion apparatus of claim 6, wherein the shape sensor includes bend sensors arranged along a longitudinal axis of the flexible tube, each bend sensor being configured to detect a bend of a portion of the flexible tube on which the bend sensor is provided, and the processor is configured to calculate the shape of the flexible tube, based on information of a curvature of each of various portions of the flexible tube detected by the bend sensor.

8. The flexible tube insertion apparatus of claim 6, wherein the shape sensor includes position sensors arranged along a longitudinal axis of the flexible tube, each position sensor being configured to detect a bend of a portion of the flexible tube on which the position sensor is provided, and
the processor is configured to calculate the shape of the flexible tube, based on information of a position of each of various portions of the flexible tube detected by the position sensor.

9. The flexible tube insertion apparatus of claim 6, wherein the processor is configured to calculate a curvature of each of various portions of the flexible tube, based on the shape information of each of various portions of the flexible tube acquired by the shape sensor, and configured to detect the occurrence of the buckling, based on the curvature.

10. The flexible tube insertion apparatus of claim 9, wherein the processor is configured to judge that the buckling occurs in the flexible tube, if the curvature of any one of the various portions of the flexible tube exceeds a threshold for buckling occurrence detection.

11. The flexible tube insertion apparatus of claim 10, wherein the processor is configured to determine that the stiffness-to-be-enhanced portion is a portion of the flexible tube that corresponds to a range in which the curvature exceeds a threshold for stiffness-to-be-enhanced portion determination that is lower than the threshold for buckling occurrence detection.

12. The flexible tube insertion apparatus of claim 10, wherein the processor is configured to judge that the pulling operation is performed, when the curvature of the buckling portion decreases below a threshold for buckling elimination detection that is lower than the threshold for buckling occurrence detection.

13. The flexible tube insertion apparatus of claim 10, wherein the processor is configured to set a buckling occurrence expectation area where the occurrence of the buckling is expected, and configured to determine that the stiffness-to-be-enhanced portion is a portion of the flexible tube that is located in the buckling occurrence expectation area in the flexible tube in which the buckling is eliminated.

14. The flexible tube insertion apparatus of claim 9, wherein the processor is configured to calculate a maximum point of a curvature of a bend portion that is located on a distal side of the buckling portion and is closest to the buckling portion, and configured to determine the stiffness-to-be-enhanced portion, based on the maximum point.

15. The flexible tube insertion apparatus of claim 14, wherein the processor is configured to determine that the stiffness-to-be-enhanced portion is a portion of the flexible tube that includes the maximum point and corresponds to a range including at least a part of the buckling portion.

16. The flexible tube insertion apparatus of claim 9, wherein the processor is configured to calculate an inflection point between the buckling portion and a bend portion that is located on a distal side of the buckling portion and is closest to the buckling portion, and configured to determine the stiffness-to-be-enhanced portion, based on the inflection point.

17. The flexible tube insertion apparatus of claim 16, wherein the processor is configured to determine that the stiffness-to-be-enhanced portion is a portion of the flexible tube that includes the inflection point and corresponds to a range including at least a part of the buckling portion.

18. The flexible tube insertion apparatus of claim 6, wherein the processor is configured to calculate a velocity of each of various portions of the flexible tube, based on the shape information of each of various portions of the flexible tube acquired by the shape sensor, configured to calculate a velocity ratio of two mutually distanced portions of the flexible tube, and configured to detect the occurrence of the buckling, based on the velocity ratio.

19. The flexible tube insertion apparatus of claim 18, wherein the processor is configured to judge that the buckling occurs in the flexible tube, when the velocity ratio of any one of sets of two portions of the flexible tube is lower than the threshold for buckling occurrence detection.

20. The flexible tube insertion apparatus of claim 19, wherein the processor is configured to determine that the stiffness-to-be-enhanced portion is a portion of the flexible tube that corresponds to a portion with the velocity ratio lower than a threshold for stiffness-to-be-enhanced portion determination that is higher than the threshold for buckling occurrence detection.

21. The flexible tube insertion apparatus of claim 19, wherein the processor is configured to judge that the pulling operation is performed, when the velocity ratios of all sets of two portions of the flexible tube exceed a threshold for buckling elimination detection that is greater than the threshold for buckling occurrence detection.

22. The flexible tube insertion apparatus of claim 6, wherein the processor is configured to calculate a crossing angle between a tangent line at an inflection point of two successive bend portions formed in the flexible tube, and a straight line passing through an axis of the flexible tube in a predetermined position of the tract, and configured to detect the occurrence of the buckling, based on the crossing angle.

23. The flexible tube insertion apparatus of claim 22, wherein the processor is configured to judge that the buckling occurs in the flexible tube, when a variation with time of the crossing angle is positive.

24. The flexible tube insertion apparatus of claim 22, wherein the processor is configured to judge that the buckling occurs in the flexible tube, when the crossing angle is greater than a threshold for buckling occurrence detection.

25. The flexible tube insertion apparatus of claim 24, wherein the processor is configured to judge that the puling operation is performed, when the crossing angle is less than a threshold for buckling elimination detection that is lower than the threshold for buckling occurrence detection.

26. The flexible tube insertion apparatus of claim 6, wherein the processor is configured to calculate a radius of curvature of a proximal-side bend portion of two successive bend portions formed in the flexible tube, and configured to detect the occurrence of the buckling, based on the radius of curvature.

27. The flexible tube insertion apparatus of claim 26, wherein the processor is configured to judge that the buckling occurs in the flexible tube, when a variation with time of the radius of curvature is negative.

28. The flexible tube insertion apparatus of claim 1, wherein the processor is configured to measure an insertion amount of the flexible tube and to detect a position of a predetermined portion of the flexible tube, and configured to detect the occurrence of the buckling, based on the insertion amount and the position.

29. The flexible tube insertion apparatus of claim 1, wherein the processor is configured to measure an insertion amount of the flexible tube, and configured to judge that the pulling operation is performed, when the insertion amount decreases by an amount greater than a threshold.

30. The flexible tube insertion apparatus of claim 1, wherein the stiffness-to-be-enhanced portion further includes a portion of the flexible tube that corresponds to the buckling portion.

31. An insertion control apparatus comprising:
a processor comprising hardware, the processor being configured to:
control a stiffness of each of various portions of a flexible tube configured to be inserted into a tract of a target;
detect occurrence of a buckling in the flexible tube;
detect that a pulling operation of the flexible tube is performed, after detecting the occurrence of the buckling;
store position information of a stiffness-to-be-enhanced portion including a portion of the flexible tube adjacent to a buckling portion of the flexible tube and located on a distal side of the buckling portion, and
increase a stiffness of the stiffness-to-be-enhanced portion, based on the position information stored in the storage device, when the pulling operation is detected.

32. A flexible tube insertion method comprising:
controlling a stiffness of each of various portions of a flexible tube to be inserted into a tract of a target;
detecting occurrence of a buckling in the flexible tube;
detecting that a pulling operation of the flexible tube is performed, after detecting the occurrence of the buckling;
storing position information of a stiffness-to-be-enhanced portion including a portion of the flexible tube adjacent to a buckling portion of the flexible tube and located on a distal side of the buckling portion; and
increasing a stiffness of the stiffness-to-be-enhanced portion, based on the stored position information, when detecting the pulling operation.

33. A flexible tube insertion method comprising:
inserting a flexible tube into a tract of a target, the flexible tube including stiffness changing devices arranged along a longitudinal axis of the flexible tube;
performing a pulling operation of the flexible tube after a buckling occurs in the flexible tube; and
increasing a stiffness of a stiffness changing device that is located at a stiffness-to-be-enhanced portion including a portion of the flexible tube adjacent to a buckling portion of the flexible tube and located on a distal side of the buckling portion, after the pulling operation is performed.

* * * * *